US012656339B2

(12) United States Patent
Bae et al.

(10) Patent No.: US 12,656,339 B2
(45) Date of Patent: Jun. 16, 2026

(54) METHODS, REAGENTS, AND SUBSTRATES FOR DETECTING TARGET ANALYTES

(71) Applicant: Purdue Research Foundation, West Lafayette, IN (US)

(72) Inventors: Euiwon Bae, West Lafayette, IN (US); Carmen Gondhalekar, West Lafayette, IN (US); Bartlomiej Rajwa, West Lafayette, IN (US); J. Paul Robinson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1021 days.

(21) Appl. No.: 17/275,122

(22) PCT Filed: Sep. 13, 2019

(86) PCT No.: PCT/US2019/051017
§ 371 (c)(1),
(2) Date: Mar. 10, 2021

(87) PCT Pub. No.: WO2020/056257
PCT Pub. Date: Mar. 19, 2020

(65) Prior Publication Data
US 2022/0120738 A1      Apr. 21, 2022

Related U.S. Application Data

(60) Provisional application No. 62/731,732, filed on Sep. 14, 2018.

(51) Int. Cl.
| | |
|---|---|
| *G01N 33/543* | (2006.01) |
| *G01N 21/64* | (2006.01) |
| *G01N 33/548* | (2006.01) |

(52) U.S. Cl.
CPC ... *G01N 33/54306* (2013.01); *G01N 21/6402* (2013.01); *G01N 21/6428* (2013.01); *G01N 33/54346* (2013.01); *G01N 33/548* (2013.01); *G01N 2021/6439* (2013.01); *G01N 2201/06113* (2013.01)

(58) Field of Classification Search
None
See application file for complete search history.

(56) References Cited

U.S. PATENT DOCUMENTS

2016/0161415 A1* 6/2016 Robinson ......... G01N 33/56911
435/7.37

FOREIGN PATENT DOCUMENTS

| EP | 1918714 A1 * | 5/2008 | ......... G01N 33/6848 |
|---|---|---|---|
| WO | 2010/033452 A2 | 3/2010 | |
| WO | 2016/040924 A1 | 3/2016 | |

OTHER PUBLICATIONS

Sher, Mazhar, et al. "Paper-based analytical devices for clinical diagnosis: recent advances in the fabrication techniques and sensing mechanisms." Expert review of molecular diagnostics 17.4 (2017): 351-366. (Year: 2017).*

(Continued)

*Primary Examiner* — Rebecca M Giere
*Assistant Examiner* — Alexander Alexandrovic Volkov
(74) *Attorney, Agent, or Firm* — Brown Rudnick LLP; Adam M. Schoen

(57) ABSTRACT
The invention generally relates to methods, reagents, and substrates for detecting target analytes.

7 Claims, 53 Drawing Sheets

(56)                    References Cited

OTHER PUBLICATIONS

Oelmann et al. Depth-resolved sample composition analysis using laser-induced ablation-quadrupole mass spectrometry and laser-induced breakdown spectroscopy, Spectrochimica Acta Part B: Atomic Spectroscopy, vol. 144, 2018, p. 38-45. (Year: 2018).*

Haushalter KJ, Vetcha S, Haushalter RC. Multiplex Flow Assays. ACS Omega. Oct. 31, 2016; 1(4):586-599. (Year: 2016).*

Extended European Search Report issued in European Application No. 19860923.2, date of mailing: Apr. 29, 2022, 9 pages.

Markushin, 2009, LIBS-based multi-element coded assay for ovarian cancer application, Proceedings of the Spie, 7190.

Markushin, 2012, Sensitive Detection of Epithelial Ovarian Cancer Biomarkers Using Tag-Laser Induced Breakdown Spectroscopy, Ovarian Cancer—Basic Science Perspective, pp. 153-170.

Markushin, 2015, Tag-femtosecond laser-induced breakdown spectroscopy for the sensitive detection of cancer antigen 125 in blood plasma, Analytical and Bioanalytical Chemistry, Springer Berlin Heidelberg, Berlin/Heiderlberg, 407(7):1849-1855.

Aragon, 1997, Two-Dimensional Spatial Distribution of the Time-Integrated Emission from Laser-Produced Plasmas in Air at Atmospheric Pressure, Applied Spectroscopy 51(11):1632-1638.

Corneillie, 1974, Chelating agents for the binding of meta ions to macromolecules, Nature, 250:587-588.

Harada, 1993, Monoclonal antibody G6K12 specific for membrane-associated differentiation marker of human stratified squamous epithelia and squamous cell carcinoma, J. Oral Pathol. Med., 22(4):145-152.

Inai, 1993, Immunohistochemical detection of an enamel protein-related epitope in rat bone at an early stage of osteogenesis, Histochemistry, 99(5):335-362.

Love, 1993, How the anti-(metal chelate) antibody CHA255 is specific for the metal ion of its antigen: X-ray structures for two Fab'/hapten complexes with different metals in the chelate, Biochemistry, 32(41):10950-9.

Meares, 1986, Chelating agents for the binding of metal ions to antibodies, International Journal of Radiation Applications and Instrumentation, Part B. Nuclear Medicine and Biology, 13(4):311-318.

Mulder, 1993, Characterization of Two Human Monoclonal Antibodies Reactive with HLA-B12 and HLA-B60, Respectively, Raised by in vitro Secondary Immunization of Peripheral Blood Lymphocytes, Hum. Immunol. Methods, 161(2):157-168.

Rakovsky, 2014, A review of the development of portable laser induced breakdown spectroscopy and its applications, Spectrochimica Acta Part B: Atomic Spectroscopy, 101:267-287.

Stauber, 1993, Rapid generation of monoclonal antibody-secreting hybridomas against African horse sickness virus by in vitro immunization and the fusion/cloning technique, J. Immunol. Methods, 161(2):157-168.

Torchilin, 1991, The antibody-linked chelating polymers for nuclear therapy and diagnostics, Crit Rev Ther Drug Carrier Syst., 7(4):275-308.

Venkateswaran, 1992, Production of Anti-Fibroblast Growth Factor Receptor Monoclonal Antibodies by In Vitro Immunization, Hybridoma, 11(6):729-739.

* cited by examiner

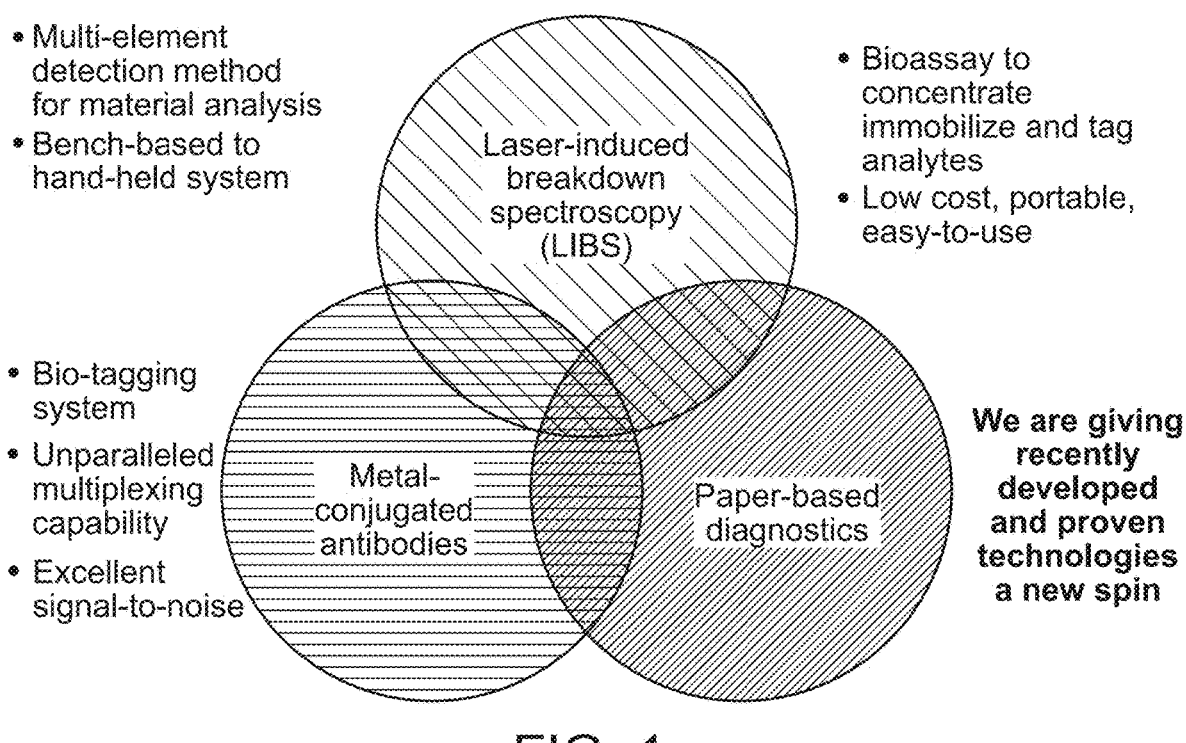

- Multi-element detection method for material analysis
- Bench-based to hand-held system

- Bio-tagging system
- Unparalleled multiplexing capability
- Excellent signal-to-noise

- Bioassay to concentrate immobilize and tag analytes
- Low cost, portable, easy-to-use

We are giving recently developed and proven technologies a new spin

Laser-induced breakdown spectroscopy (LIBS)

Metal-conjugated antibodies

Paper-based diagnostics

FIG. 1

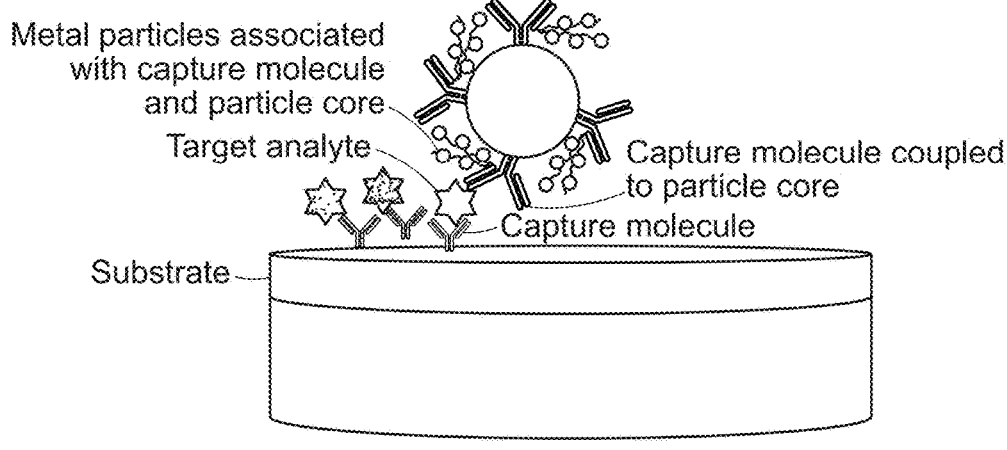

Metal particles associated with capture molecule and particle core

Target analyte

Capture molecule coupled to particle core

Capture molecule

Substrate

FIG. 2

Metal-chelated polymer (unique metal for each target analyte)

Anti-botulinum Ab

Anti-ricin Ab

Anti-shiga Ab

Botulinum toxin

Ricin toxin

Shiga toxin

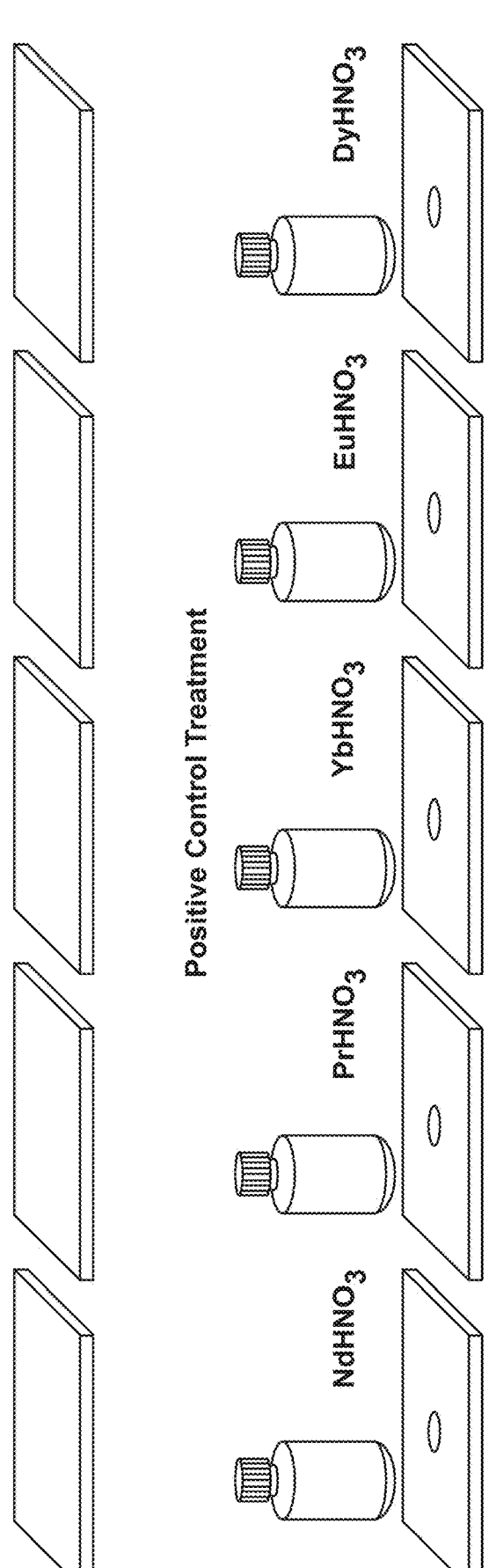
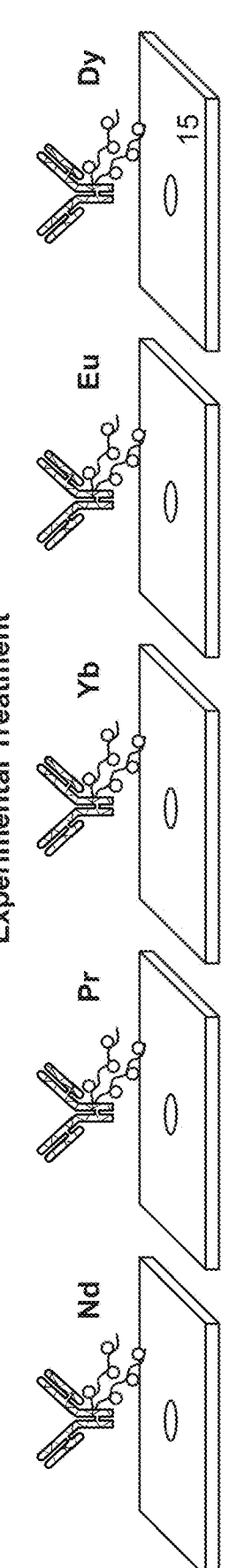
FIG. 7

Gold foil

Dry

Wet

Metal-chelated polymer

Anti-rabbit Ab

Rabbit Ab

LIBS beam

LIBS is used to sample nine locations along the pink line and nine locations along the area adjacent to the pink line Pink line Pregnancy test strip Wavelength (nm)

■ Dry pink line   □ Dry negative control

Wavelength (nm)

■ Au experimental   □ Au neg.control

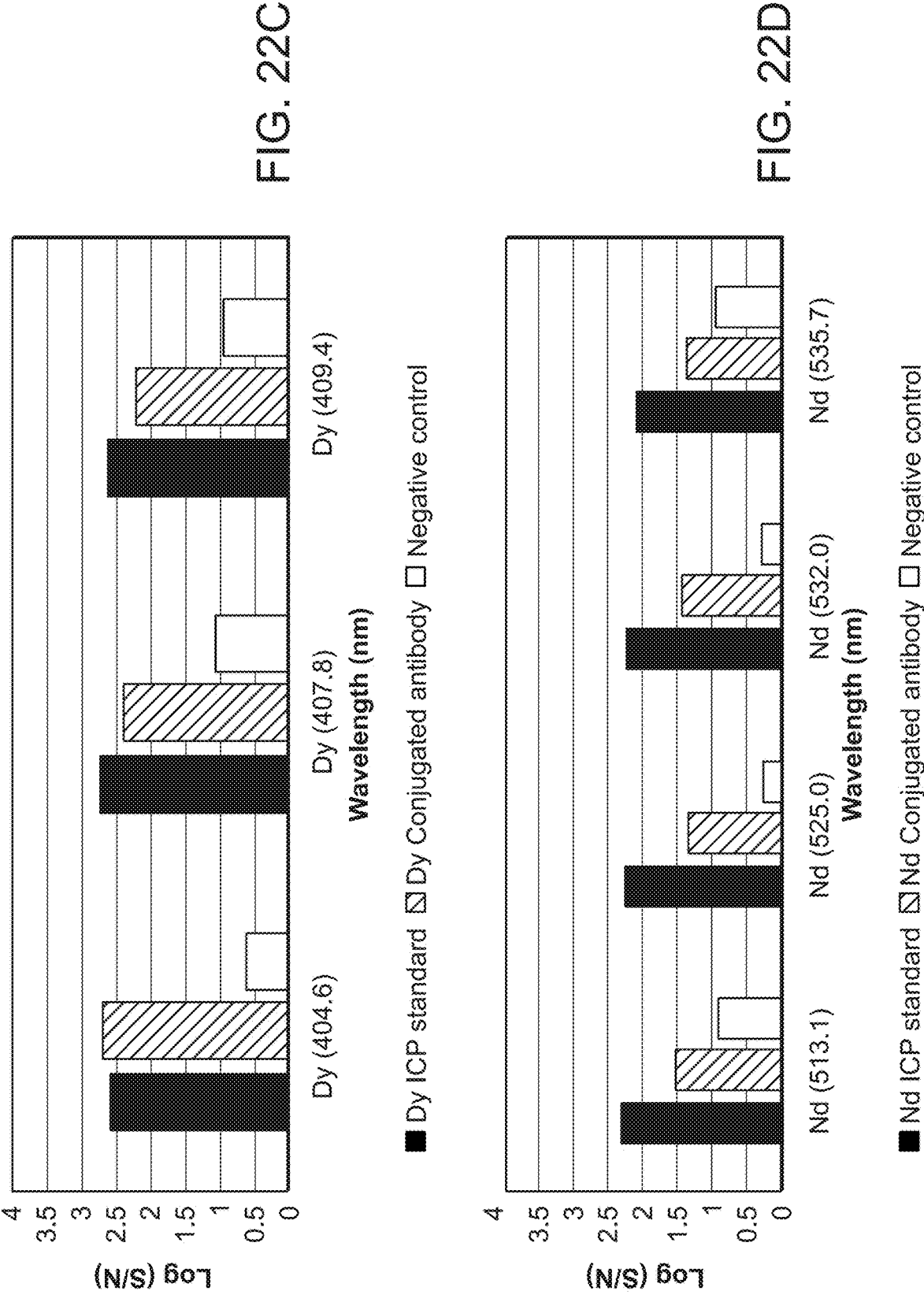

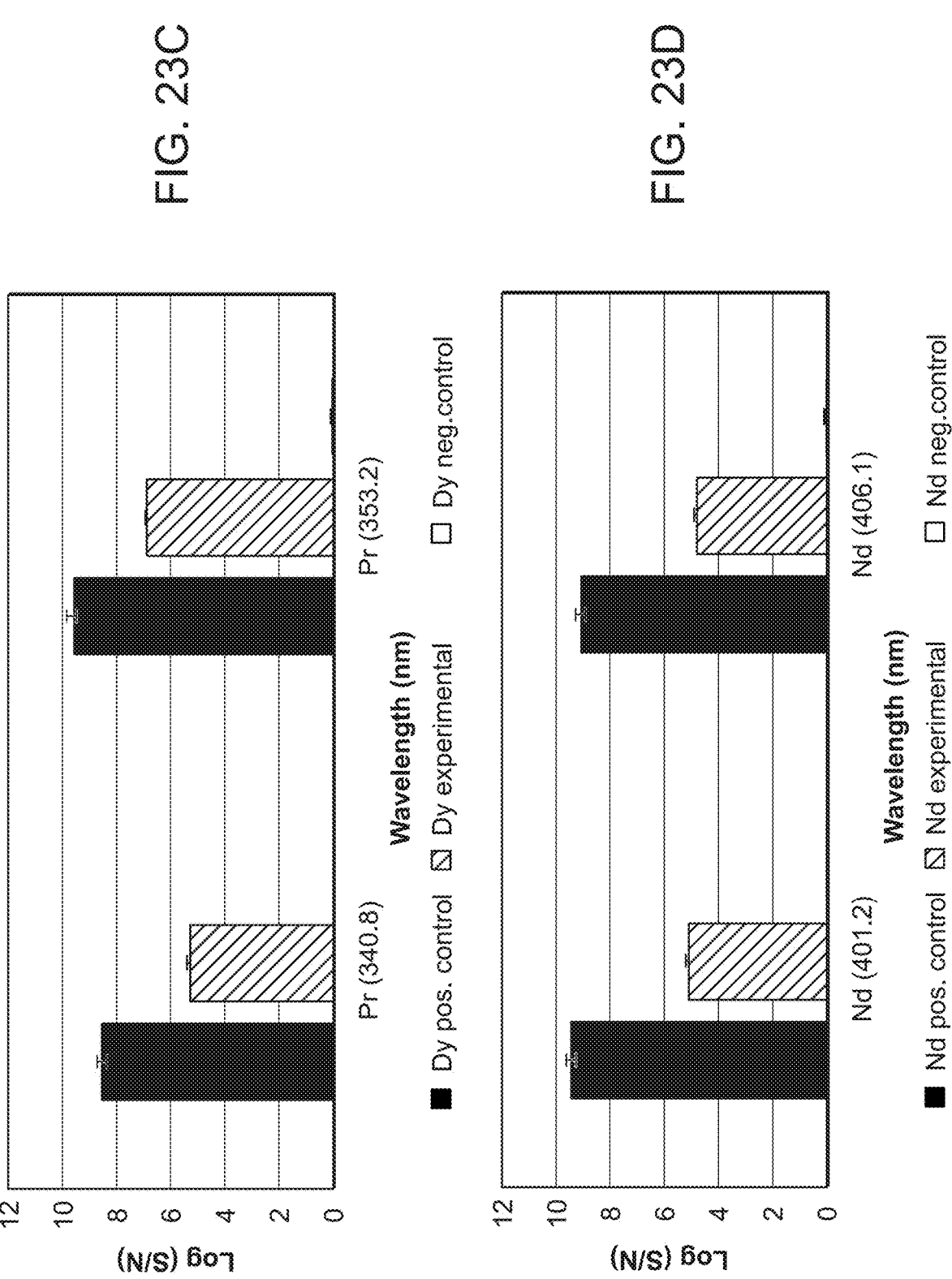

Nanoparticles optically visible to naked eye on a substrate

Cartridge

Layer 5 - absorbent pad

Layer 1 - targets toxin A and B

Layer 2 - targets toxin C and D

Layer 3 - targets toxin E and F

Layer 4 - targets toxin G and H

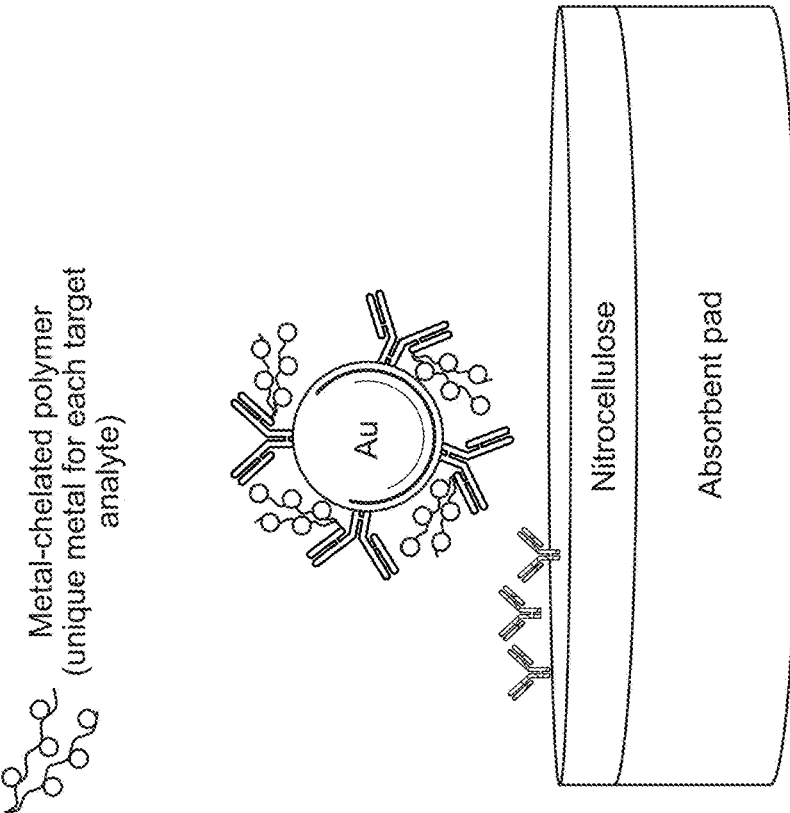
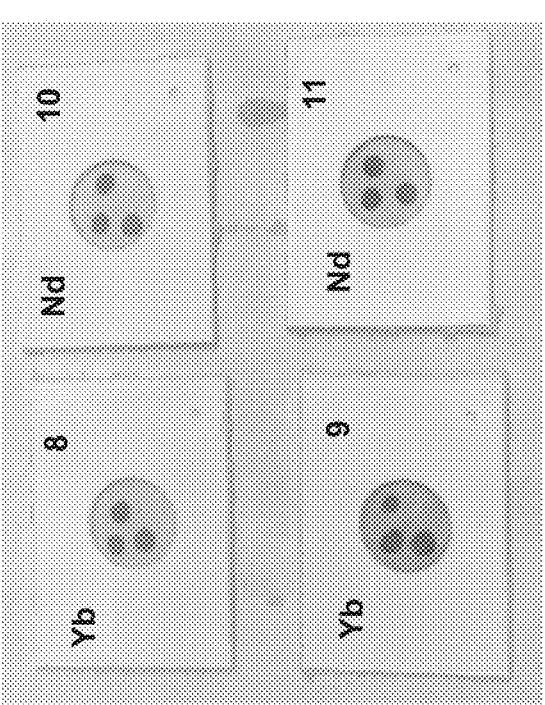
FIG. 35

METHODS, REAGENTS, AND SUBSTRATES FOR DETECTING TARGET ANALYTES

RELATED APPLICATION

The present application is a 35 U.S.C. § 371 national phase application of PCT/US19/51017, filed Sep. 13, 2019, which claims the benefit of and priority to U.S. provisional application Ser. No. 62/731,732, filed Sep. 14, 2018, the content of each of which is incorporated by reference herein in its entirety.

GOVERNMENT SUPPORT

This invention was made with government support under 59-1935-2-279 awarded by the U.S. Department of Agriculture, Agricultural Research Service and DGE-1333468 awarded by the National Science Foundation. The government has certain rights in the invention.

FIELD OF THE INVENTION

The invention generally relates to methods, reagents, and substrates for detecting target analytes.

BACKGROUND

Agencies interested in analyte detection technologies (e.g., bio-hazard detection) prioritize low cost, speed and field portability for application of the technology in, for example, emergency response, environmental health, military field work, and food inspection scenarios. Current tools for analyte detection do not satisfy the required needs, as current technologies are either low cost, rapid, multiplexed, or portable—but not all three.

SUMMARY

The invention provides improved analyte detection methods and technologies that combine the use of one or a combination of laser systems (such as laser-induced breakdown spectroscopy (LIBS)), metal conjugated capture molecules (e.g., metal conjugated antibodies), and porous substrate diagnostics (e.g., paper-based diagnostics). The invention recognizes that metals are a powerful bio-tag, each metal producing a unique atomic signal with little overlap, which creates opportunities to for highly multiplexed assays. Metals can be conjugated to capture molecules (e.g., antibodies) in a variety of different ways, which are discussed herein. At this time, up to 21 metals are known to have been conjugated (either covalently or non-covalently) to metals. This offers a large panel of labels.

Leveraging these different technologies, the invention provides a porous substrate based bioassay (e.g., a paper-based bioassay) to concentrate a target analyte, and label the target analyte with a metal bio-tag. In certain embodiments, one or more capture molecules (e.g., antibodies) targeting one or more analytes are functionalized to a region of porous material (e.g., nitrocellulose paper). When a sample is added, the target analyte will bind to the porous material. Capture molecules complexed to metals (a unique metal per capture molecule target) and conjugated to metal particles (e.g., gold nanoparticles) are then used to label the analyte on the porous material.

Analysis of the bioassay is performed using a laser based technology, such as Laser-Induced Breakdown Spectroscopy (LIBS), which is a technique to characterize the elemental composition of a material. Detection of a metal-complexed capture molecule indicates the presence of the associated analyte in the sample. The unique and narrow signal produced by every capture molecule permits LIBS to detect each analyte in a single sampling event.

The assays and technologies described herein can be utilized in a single-plex format or a multiplexed format (detection of n number of targets in a single assay).

In certain aspects, the invention provides methods for detecting a target analyte. The methods involve forming a first sandwich complex on a substrate comprising a first target analyte from a sample and one or more first metal particles; directing a laser emission from a laser source onto the first sandwich complex such that the laser emission causes the one or more first metal particles associated with the first sandwich complex to produce a first emission signal; and detecting the first emission signal from the first sandwich complex, the first emission signal being indicative of presence of the first target analyte. In certain embodiments, the directing and detecting steps are accomplished using Laser-Induced Breakdown Spectroscopy (LIBS) or Spark-Induced Breakdown Spectroscopy (SIBS), or combinations of such.

The first sandwich complex can be formed by introducing the sample comprising a first target analyte to the substrate comprising a first capture molecule that is specific to the first target analyte, wherein the first target analyte binds the first capture molecule; and introducing a first reagent to the substrate, the first reagent comprising (i) a core metal nanoparticle having a second capture molecule coupled thereto or (ii) a second capture molecule without a core metal nanoparticle; and one or more first metal particles (such as molecules or atoms) coupled to the second capture molecule, wherein the first reagent binds the first target analyte via the second capture molecule to thereby form the first sandwich complex on the substrate. In certain embodiments, the first and second capture molecules are the same. In other embodiments, the first and second capture molecules are different.

In certain embodiments, the sample comprises a second target analyte and the method further comprises forming a second sandwich complex on the substrate comprising the second target analyte and one or more second metal particles; directing a laser emission from the laser source onto the second sandwich complex such that the laser emission causes the one or more second metal particles associated with the second sandwich complex to produce a second emission signal; and detecting the second emission signal from the second sandwich complex, the second emission signal being indicative of presence of the second target analyte. In certain embodiments, the directing and detecting steps are accomplished using Laser-Induced Breakdown Spectroscopy (LIBS) or Spark-Induced Breakdown Spectroscopy (SIBS), or combinations of such.

The second sandwich complex can be formed by introducing a second target analyte in the sample to the substrate comprising a third capture molecule that is specific to the second target analyte and different from the first capture molecule, wherein the second target analyte binds the second capture molecule; and introducing a second reagent to the substrate, the second reagent comprising (i) a core metal nanoparticle having a third capture molecule coupled thereto or (ii) a third capture molecule without a core metal nanoparticle; and one or more second metal particles (such as molecules or atoms) coupled to the fourth capture molecule, wherein the one or more second metal particles are different from the one or more first metal particles and the second reagent binds the second target analyte via the fourth capture molecule to thereby form a second sandwich complex. In certain embodiments, the third and fourth capture molecules are the same. In other embodiments, the third and fourth capture molecules are different.

The first and second reagents may be introduced to the substrate in a single liquid or multiple liquids, with a single liquid being preferred. Numerous different capture molecules are known in the art and may be used with the methods of the invention, a number of which are described herein. In an exemplary embodiment, the first capture molecule is an antibody. Likewise, numerous different porous substrates are known in the art and may be used with the methods of the invention, a number of which are described herein. In certain embodiments, the substrate is a paper substrate, such as a nitrocellulose paper substrate. In certain embodiments, the one or more first metal particles are coupled to a polymer which is coupled to the second capture molecule.

The invention also provided a multiplexed assay format that allows for detection of n number of analytes. In such aspects, the invention provides methods for detecting a plurality of target analytes. Those methods involve providing a substrate comprising a first layer on top of a second layer, wherein the first layer comprises a first capture molecule that is specific to a first target analyte and the second layer comprises a second capture molecule that is specific to a second target analyte; forming a first sandwich complex on the first layer of the substrate comprising the first target analyte from the sample and one or more first metal particles; forming a second sandwich complex on the second layer of the substrate comprising the second target analyte from the sample and one or more second metal particles; directing a laser emission from a laser source onto the first sandwich complex on the first layer such that the laser emission causes the one or more first metal particles associated with the first sandwich complex to produce a first emission signal, wherein the laser emission also ablates through the first layer to the second layer and is directed onto the second sandwich complex on the second layer such that the laser emission causes the one or more second metal particles associated with the second sandwich complex to produce a second emission signal; and detecting the first emission signal from the first sandwich complex and the second emission signal from the second sandwich complex, the first emission signal being indicative of presence of the first target analyte on the first layer and the second emission signal being indicative of presence of the second target analyte on the second layer. In certain embodiments, the directing and detecting steps are accomplished using Laser-Induced Breakdown Spectroscopy (LIBS) or Spark-Induced Breakdown Spectroscopy (SIBS), or combinations of such.

The first and second sandwich complexes can be formed by introducing the sample comprising the first target analyte and the second target analyte to the substrate in a manner that the sample flows through the substrate, wherein the first target analyte binds the first capture molecule on the first layer and the second target analyte binds the second capture molecule on the second layer; introducing a first reagent to the substrate, the first reagent comprising (i) a core metal nanoparticle having a third capture molecule coupled thereto or (ii) a third capture molecule without a core metal nanoparticle; and one or more first metal particles coupled to the third capture molecule, wherein the first reagent binds the first target analyte on the first layer via the third capture molecule to thereby form the first sandwich complex; and introducing a second reagent to the substrate, the second reagent comprising (i) a core metal nanoparticle having a fourth capture molecule coupled thereto or (ii) a fourth capture molecule without a core metal nanoparticle; and one or more second metal particles coupled to the fourth capture molecule, wherein the second reagent flows through the first layer to the second layer and binds the second target analyte on the second layer via the fourth capture molecule to thereby form the second sandwich complex. In certain embodiments, the first and second capture molecules are the same. In other embodiments, the first and second capture molecules are different. In certain embodiments, the third and fourth capture molecules are the same. In other embodiments, the third and fourth capture molecules are different.

In certain embodiments the sample comprises a third target analyte, and the multiplexed methods may further involve forming a third sandwich complex on the first layer of the substrate comprising the third target analyte and one or more third metal particles; directing a laser emission from the laser source onto the third sandwich complex such that the laser emission causes the one or more third metal particles associated with the third sandwich complex on the first layer to produce a third emission signal; and detecting the third emission signal from the third sandwich complex, the third emission signal being indicative of presence of the third target analyte. In certain embodiments, the directing and detecting steps are accomplished using Laser-Induced Breakdown Spectroscopy (LIBS) or Spark-Induced Breakdown Spectroscopy (SIBS), or combinations of such.

The third sandwich complex may be formed by introducing the third target analyte in the sample to the first layer of the substrate comprising a fifth capture molecule that is specific to the third target analyte and different from the first and second capture molecules, wherein the third target analyte binds the third capture molecule on the first layer; and introducing a third reagent to the substrate, the third reagent comprising (i) a core metal nanoparticle having a sixth capture molecule coupled thereto or (ii) a sixth capture molecule without a core metal nanoparticle; and one or more third metal particles coupled to the sixth capture molecule, wherein the one or more third metal particles are different from the one or more first and second metal particles and the third reagent binds the third target analyte on the first layer via the sixth capture molecule to thereby form the third sandwich complex. In certain embodiments, the fifth and sixth capture molecules are the same. In other embodiments, the fifth and sixth capture molecules are different.

The first, second, and/or third reagents may be introduced to the substrate in a single liquid or multiple liquids, with a single liquid being preferred. Numerous different capture molecules are known in the art and may be used with the methods of the invention, a number of which are described herein. In an exemplary embodiment, the first and second capture molecules are antibodies. Likewise, numerous different porous substrates are known in the art and may be used with the methods of the invention, a number of which are described herein. In certain embodiments, the substrate is a paper substrate, such as a nitrocellulose paper substrate. In certain embodiments, the one or more first metal particles are coupled to a polymer which is coupled to the first capture molecule and the one or more second metal particles are coupled to a polymer which is coupled to the second capture molecule.

The assays (single-plex and multiplex) described herein leverage certain inventive technologies. Accordingly, another aspect of the invention provides a substrate comprising a plurality of porous layers arranged on top of each other, each layer of the plurality of layers comprising at least one capture molecule, wherein capture molecules on a first layer of the plurality of layers are of a different type from capture molecules on a second layer of the plurality of layers.

In certain embodiments, each layer comprises two or more different types of capture molecules and the none of the capture molecules on any of the layers are of a same type. Numerous different capture molecules are known in the art and may be used with the substrates of the invention, a number of which are described herein. In an exemplary embodiment, the first and second capture molecules are antibodies. Likewise, numerous different porous substrates are known in the art and may be used as the substrate of the invention, a number of which are described herein. In certain embodiments, the substrate is a paper substrate, such as a nitrocellulose paper substrate. In certain embodiments, the substrate additionally comprising an absorbent layer arranged below the plurality of porous layers.

Each porous layer may comprise one or more characteristics selected from the group consisting of: material type, porosity, thickness, and a combination thereof. In certain embodiments, each porous layer comprises the same characteristics. In other embodiments, each porous layer comprises different characteristics. In certain embodiments, the plurality of porous layers are compatible for Laser-Induced Breakdown Spectroscopy (LIBS) or Spark-Induced Breakdown Spectroscopy (SIBS). Other possible detection technologies include laser-ablation mass spectroscopy or laser-ablation inductively coupled optical emission spectroscopy. In certain embodiments, combinations of different laser based systems are contemplated.

Another aspect of the invention provides a reagent comprising a particle core; one or more capture molecules coupled to the particle core; and one or more metal particles coupled to each of the one or more capture molecules.

In certain embodiments the particle core may be a metal particle core. For example, the metal particle core may be a metal nanoparticle core. Preferably, the metal particle core comprises a visually detectable metal, such as gold.

Numerous different capture molecules are known in the art and may be used with the reagents of the invention, a number of which are described herein. In an exemplary embodiment, the capture molecule is an antibody. In certain embodiments, the one or more metal particles are coupled to a polymer which is coupled to the one or more capture molecules.

The invention also provides kits, which may include the reagent(s) described herein, or the substrate(s) described herein, or both the reagents and substrates described herein. The kits may also include instructions for use.

BRIEF DESCRIPTION OF THE DRAWINGS

FIG. 1 is a diagram illustrating exemplary technologies used in the methods of the invention.

FIG. 2 is a diagram illustrating an exemplary sandwich complex.

FIG. 7 is an illustration showing that metals (Pr, Nd, Yb, Eu, and Pr) were conjugated to antibodies and sampled using LIBS and LA-ICP-OES. Each metal conjugate was compared to a positive and negative control.

FIGS. 22A-E show that LIBS was performed on paper samples bearing Pr (FIG. 22A), Eu (FIG. 22B), Dy (FIG. 22C) and Nd (FIG. 22D), and Yb (FIG. 22E). For each lanthanide, 3 treatments were tested: ICP standard on paper, lanthanide-conjugated antibody on paper, and untreated paper. All samples were ablated 15 times in different locations. The 15 sampling events were aggregated, converted to S/N in log scale, and plotted. The plots show that for each lanthanide (except the 404.6 nm line of Dy (FIG. 22E)), the ICP standard produced the strongest signal, followed by the lanthanide conjugated antibody, and then the untreated nitrocellulose.

FIGS. 23A-D show that LA-ICP-OES was performed on paper samples bearing Pr (FIG. 23A), Eu (FIG. 23B), Dy (FIG. 23C) and Nd (FIG. 23D). For each lanthanide, 3 treatments were tested: ICP standard on paper, lanthanide-conjugated antibody on paper, and untreated paper. For each lanthanide, the ICP standard produced the strongest signal, followed by the lanthanide conjugated antibody, and then the untreated nitrocellulose.

FIG. 27A shows crater formed by XLP-1064-1 laser (Laser "A") (used to acquire data on gold nanoparticles on the surface of a silicon wafer). FIG. 27B shows crater formed by COBOLT TOR XS laser (high performance Q-switched lasers).

FIG. 35 is another example for a single layer assay showing metal-bearing polymers complexed to antibodies, which were conjugated to the surface of nanoparticles.

DETAILED DESCRIPTION

Figures 3, 4:
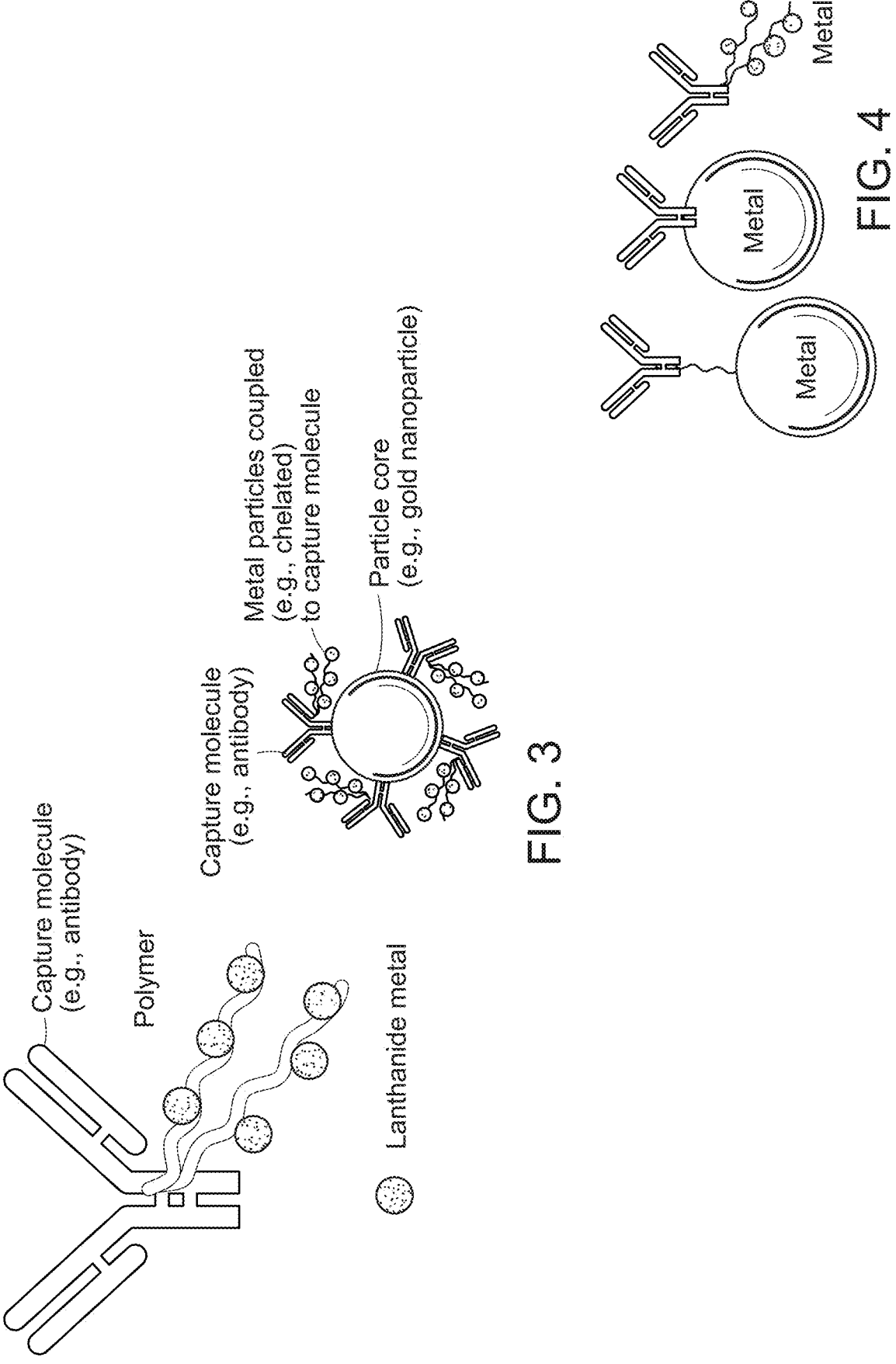
FIG. 3 illustrates an exemplary reagent of the invention.
FIG. 4 displays covalent methods of conjugating antibodies to metals (far left and right), as well as non-covalent conjugation (middle).

The invention generally relates to methods, reagents, and substrates for detecting target analytes. As shown in FIG. 1, in certain aspects and embodiments, the invention leverages three core technologies: laser based detection systems (illustrated in FIG. 1 by example as laser-induced breakdown spectroscopy (LIBS)), metal conjugated capture molecules (e.g., illustrated in FIG. 1 by example as metal conjugated antibodies), and porous substrate diagnostics (e.g., illustrated in FIG. 1 by example as paper-based diagnostics). In that manner, the invention provides single-plex and multiplexed assays for detection of one or more target analytes, such as biological target analytes.

In certain aspects, the invention in conducted in a single-plex format (detection of a single analyte). In such embodiments, the invention involves forming a first sandwich complex on a substrate comprising a first target analyte from a sample and one or more first metal particles; directing a laser emission from a laser source onto the first sandwich complex such that the laser emission causes the one or more first metal particles associated with the first sandwich complex to produce a first emission signal; and detecting the first emission signal from the first sandwich complex, the first emission signal being indicative of presence of the first target analyte.

In other embodiments, the invention in conducted in a multiplexed format (detection of a n number of analytes). In such embodiments, the invention involves providing a substrate comprising a first layer on top of a second layer, wherein the first layer comprises a first capture molecule that is specific to a first target analyte and the second layer comprises a second capture molecule that is specific to a second target analyte; forming a first sandwich complex on the first layer of the substrate comprising the first target analyte from the sample and one or more first metal particles; forming a second sandwich complex on the second layer of the substrate comprising the second target analyte from the sample and one or more second metal particles; directing a laser emission from a laser source onto the first sandwich complex on the first layer such that the laser emission causes the one or more first metal particles associated with the first sandwich complex to produce a first emission signal, wherein the laser emission also ablates through the first layer to the second layer and is directed onto the second sandwich complex on the second layer such that the laser emission causes the one or more second metal particles associated with the second sandwich complex to produce a second emission signal; and detecting the first emission signal from the first sandwich complex and the second emission signal from the second complex, the first emission signal being indicative of presence of the first target analyte on the first layer and the second emission signal being indicative of presence of the second target analyte on the second layer.

Figure 34:
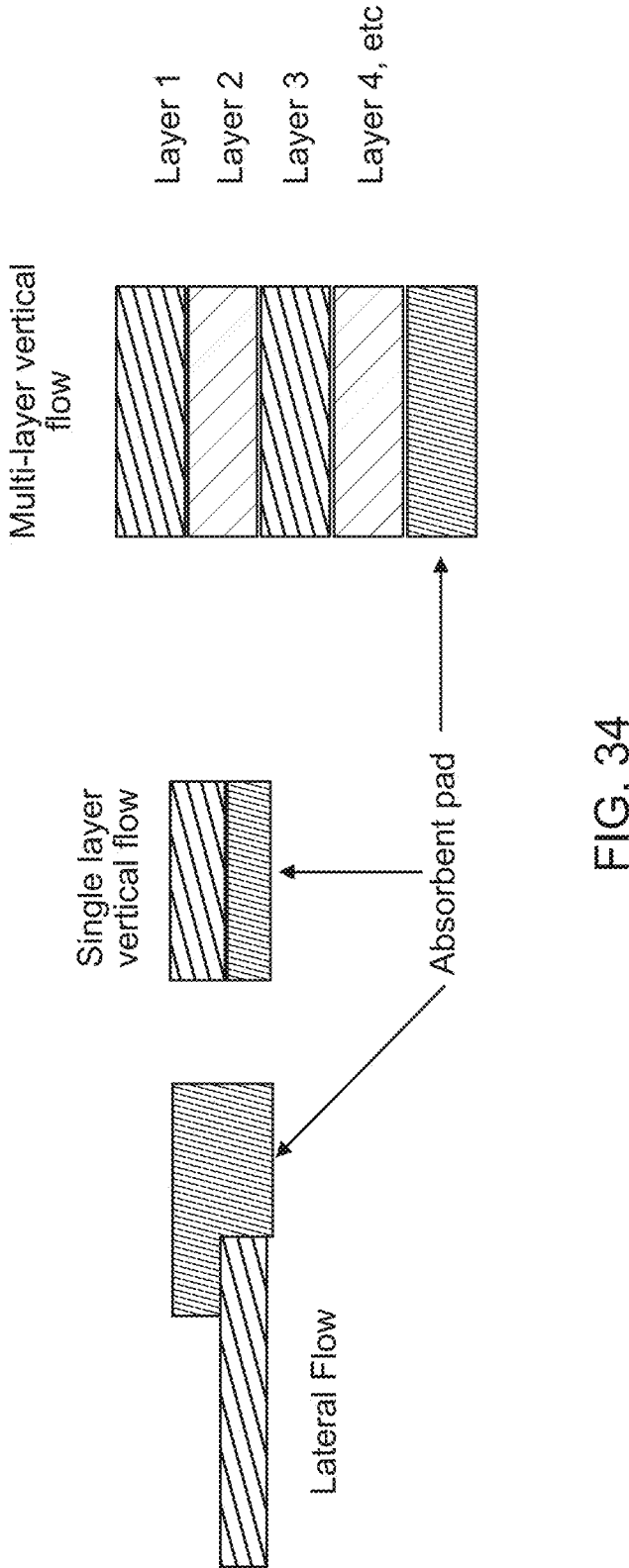
FIG. 34 is an illustration showing lateral flow and vertical flow approaches.

In certain embodiments of the single-plex and multiplex assays, the assays are conducted as vertical flow assays (as opposed to horizontal flow assays). That means that liquid flows vertically down through one or more layers on a substrate. The vertical flow format is particularly utilized in certain embodiments of the multiplex assays. Vertical flow is exemplified in at least FIG. 32. Vertical flow is distinguished from lateral (horizontal) flow, as shown in FIG. 34.

A substrate refers to a porous surface that may be composed of one or more layers. In certain embodiments, the porous surface is any cellulose-based material. An exemplary porous material is paper. In particular embodiments, the porous material is filter paper. Exemplary filter papers include cellulose filter paper, ashless filter paper, nitrocellulose paper, glass microfiber filter paper, and polyethylene paper. Filter paper having any pore size may be used. Exemplary pore sizes include Grade 1 (11 μm), Grade 2 (8 μm), Grade 595 (4-7 μm), and Grade 6 (3 μm).

In certain embodiments, the substrate is a single layer of porous material, e.g., a single layer of paper (such as nitrocellulose paper). That single layer may be functionalized with a single type of capture molecule (in multiple copies) or multiple different types of capture molecules (each type of capture molecule optionally being present in multiple copies). The substrate may also include an absorbent pad arranged beneath the single layer of porous material.

In other embodiments, the substrate includes multiple layers of porous material, e.g., multiple layers of paper (such as nitrocellulose paper). This arrangement is an exemplary substrate for the multiplexed methods. Each layer is functionalized with a different type of capture molecule (in multiple copies), meaning that the capture molecule on the first layer is of a different type than the capture molecule on the second layer. For example, layer one may include an antibody that specifically binds a first target analyte and layer two may include a second antibody that specifically binds a second target analyte. Different may also mean that the capture molecules are different classes of molecules. For example, the first layer may include an antibody that binds a first target analyte and the second layer may include an aptamer that binds a second target analyte.

Additionally, each layer may include multiple different types of capture molecules and different classes of molecules. For example, the first layer may include two different antibodies (antibodies 1 and 2) and the second layer may include two other antibodies (antibodies 3 and 4). Each of the four antibodies specifically binds a different target analyte, such that four target analytes can be captured in a single assay. In another example, the first layer may include an antibody and an aptamer (antibody 1 and aptamer 1) and the second layer may include a second antibody and a nucleic acid (antibody 2 and nucleic acid 1). Each of the four capture molecules specifically binds a different target analyte, such that four target analytes can be captured in a single assay.

FIG. 3 illustrates an exemplary reagent of the invention. As shown in FIG. 3, a reagent of the invention may include a particle core; one or more capture molecules coupled to the particle core; and one or more metal particles coupled to the each of the one or more capture molecules. In certain embodiments the particle core may be a metal particle core.

For example, the metal particle core may be a metal nanoparticle core. Preferably the metal particle core comprises a visually detectable metal, such as gold or silver. Numerous different capture molecules are known in the art and may be used with the reagents of the invention, a number of which are described herein. In an exemplary embodiment, the capture molecule is an antibody. In certain embodiments, the one or more metal particles are coupled to a polymer which is coupled to the one or more capture molecules.

Metals can be conjugated to capture molecules (such as antibodies as shown in FIG. 3) in a variety of different ways. FIG. 4 displays covalent methods of conjugating antibodies to metals (far left and right), as well as non-covalent conjugation (middle). Up to 21 metals are known to have been conjugated (either covalently or non-covalently) to metals. This offers a large panel of antibody labels. An exemplary approach of coupling a metal to a capture molecule is described for example in Love et al. (Biochemistry. 1993 Oct. 19; 32(41):10950-9), Meares et al. (International Journal of Radiation Applications and Instrumentation. Part B. Nuclear Medicine and Biology, Volume 13, Issue 4, 1986, Pages 311-318); Corneillie et al. (Journal of Inorganic Biochemistry, Volume 100, Issues 5-6, May 2006, Pages 882-890), and Torchilin et al. (Crit Rev Ther Drug Carrier Syst. 1991; 7(4):275-308), the content of each of which is incorporated by reference herein in its entirety.

Aspect of the methods herein leverage the different materials that make-up the reagents described herein. Bio-tags (such as gold, silver and latex particles) are used in association with bio-detection molecules (such as antibodies) to detect analytes because they have distinct physical properties. In an example, gold nanoparticles conjugated to antibodies are used because the gold nanoparticles can be visually detected (i.e., seen by the naked eye on a surface). That allows a user to identify where to direct the laser.

The reagent then further includes a capture molecule (e.g., antibody) complexed to a metal-bearing polymer. Capture molecules complexed to metal-bearing polymers can't be detected visually (e.g., by the naked eye) like gold or silver nanoparticles (FIG. 3). These types of bio-tags require a different type of detection technique, such as described herein.

Metals complexed to antibodies offer a broad diversity of labels because each metal produces a very unique and narrow signal when analyzed with mass or atomic spectroscopy. Since mass spectroscopy is a very bulky mode of detection, the invention preferably uses atomic spectroscopy to detect metal-conjugated antibodies.

In certain embodiments, the metal particle conjugated to the capture molecule is a lanthanide. Exemplary metal particles may be composed of one or a combination of any of silicon, iron, zinc, silver, cadmium, indium, platinum, gold, lanthanum, praseodymium, neodymium, samarium, europium, gadolinium, terbium, dysprosium, holmium, erbium, thulium, ytterbium, and/or lutetium.

A wide range of samples (e.g., heterogeneous or homogeneous samples) can be analyzed, such as biological samples, environmental samples (including, e.g., industrial samples and agricultural samples), and food/beverage product samples, etc.

Exemplary biological samples include a human tissue or bodily fluid, which may be collected in any clinically acceptable manner. A tissue is a mass of connected cells and/or extracellular matrix material, e.g. skin tissue, hair, nails, nasal passage tissue, CNS tissue, neural tissue, eye tissue, liver tissue, kidney tissue, placental tissue, mammary gland tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sputum, sweat, amniotic fluid, menstrual fluid, mammary fluid, peritoneal fluid, urine, semen, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed.

In one embodiment, the biological sample can be a blood sample, from which plasma or serum can be extracted. The blood can be obtained by standard phlebotomy procedures and then separated. Typical separation methods for preparing a plasma sample include centrifugation of the blood sample. For example, immediately following blood draw, protease inhibitors and/or anticoagulants can be added to the blood sample. The tube is then cooled and centrifuged, and can subsequently be placed on ice. The resultant sample is separated into the following components: a clear solution of blood plasma in the upper phase; the buffy coat, which is a thin layer of leukocytes mixed with platelets; and erythrocytes (red blood cells). Typically, 8.5 mL of whole blood will yield about 2.5-3.0 mL of plasma.

Blood serum is prepared in a very similar fashion. Venous blood is collected, followed by mixing of protease inhibitors and coagulant with the blood by inversion. The blood is allowed to clot by standing tubes vertically at room temperature. The blood is then centrifuged, wherein the resultant supernatant is the designated serum. The serum sample should subsequently be placed on ice.

Prior to analyzing a sample, the sample may be purified, for example, using filtration or centrifugation. These techniques can be used, for example, to remove particulates and chemical interference. Various filtration media for removal of particles includes filer paper, such as cellulose and membrane filters, such as regenerated cellulose, cellulose acetate, nylon, PTFE, polypropylene, polyester, polyethersulfone, polycarbonate, and polyvinylpyrolidone. Various filtration media for removal of particulates and matrix interferences includes functionalized membranes, such as ion exchange membranes and affinity membranes; SPE cartridges such as silica- and polymer-based cartridges; and SPE (solid phase extraction) disks, such as PTFE- and fiberglass-based. Some of these filters can be provided in a disk format for loosely placing in filter holdings/housings, others are provided within a disposable tip that can be placed on, for example, standard blood collection tubes, and still others are provided in the form of an array with wells for receiving pipetted samples. Another type of filter includes spin filters. Spin filters consist of polypropylene centrifuge tubes with cellulose acetate filter membranes and are used in conjunction with centrifugation to remove particulates from samples, such as serum and plasma samples, typically diluted in aqueous buffers.

Filtration is affected in part, by porosity values, such that larger porosities filter out only the larger particulates and smaller porosities filtering out both smaller and larger porosities. Typical porosity values for sample filtration are the 0.20 and 0.45 μm porosities. Samples containing colloidal material or a large amount of fine particulates, considerable pressure may be required to force the liquid sample through the filter. Accordingly, for samples such as soil extracts or wastewater, a pre-filter or depth filter bed (e.g. "2-in-1" filter) can be used and which is placed on top of the membrane to prevent plugging with samples containing these types of particulates.

In some cases, centrifugation without filters can be used to remove particulates, as is often done with urine samples. For example, the samples are centrifuged. The resultant supernatant is then removed and frozen.

After a sample has been obtained and purified, the sample can be analyzed to determine the concentration of one or more target analytes, such as elements within a blood plasma sample. With respect to the analysis of a blood plasma sample, there are many elements present in the plasma, such as proteins (e.g., Albumin), nucleic acids, vitamins, hormones, and other elements (e.g., bilirubin and uric acid). Any of these elements may be detected using methods of the invention. More particularly, methods of the invention can be used to detect molecules in a biological sample that are indicative of a disease state. The target analyte(s) may then be quantified and correlated to a particular disease state, such as a cancer or other disorder.

Exemplary environmental samples include, but are not limited to, groundwater, surface water, saturated soil water, unsaturated soil water; industrialized processes such as waste water, cooling water; chemicals used in a process, chemical reactions in an industrial processes, and other systems that would involve leachate from waste sites; waste and water injection processes; liquids in or leak detection around storage tanks; discharge water from industrial facilities, water treatment plants or facilities; drainage and leachates from agricultural lands, drainage from urban land uses such as surface, subsurface, and sewer systems; waters from waste treatment technologies; and drainage from mineral extraction or other processes that extract natural resources such as oil production and in situ energy production.

Additionally exemplary environmental samples include, but certainly are not limited to, agricultural samples such as crop samples, such as grain and forage products, such as soybeans, wheat, and corn. Often, data on the constituents of the products, such as moisture, protein, oil, starch, amino acids, extractable starch, density, test weight, digestibility, cell wall content, and any other constituents or properties that are of commercial value is desired.

A target analyte is the molecule in the sample to be captured, detected, and optionally quantified and correlated with an outcome or disease state. In certain embodiments, the sample in a biological sample. In such embodiments, the target analyte may be a target biological molecule in the sample (although the invention includes capturing non-biological molecules from a biological sample, such as a drug or a chemical substance). Examples of biological target analyte includes include proteins, nucleic acids (DNA and/or RNA), hormones, vitamins, bacteria, fungi, viruses, a cell (such as a cancer cell, a white blood cell a virally infected cell, or a fetal cell circulating in maternal circulation), and any biological molecules known in the art and typically found in a biological sample.

A capture molecule refers to a molecule that specifically binds a target analyte from the sample. The capture molecule chosen will depend on the target analyte to be captured and one of skill in the art will readily be able to select the capture molecule to use based on the desired target analyte to be captured and analyzed. Exemplary capture molecules include antibodies, nucleic acids (DNA or RNA), peptides, proteins, aptamers, receptors, ligands, etc.

In particular embodiments, the capture molecule is an antibody. The term antibody includes complete antibodies and any functional fragment of an antibody that can specifically bind a target analyte. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such the target bacteria, effective to produce an immune response. An exemplary protocol is as follows. The animal is subcutaneously injected in the back with 100 micrograms to 100 milligrams of antigen, dependent on the size of the animal, followed three weeks later with an intraperitoneal injection of 100 micrograms to 100 milligrams of immunogen with adjuvant dependent on the size of the animal, for example Freund's complete adjuvant. Additional intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing hepatic cells.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Methods for attaching the capture molecule, such as an antibody, to a particle core are known in the art. Coating magnetic particles with antibodies is well known in the art, see for example Harlow et al. (Antibodies, Cold Spring Harbor Laboratory, 1988), Hunter et al. (Immunoassays for Clinical Chemistry, pp. 147-162, eds., Churchill Livingston, Edinborough, 1983), and Stanley (Essentials in Immunology and serology, Delmar, pp. 152-153, 2002). Such methodology can easily be modified by one of skill in the art to bind other types of capture moieties to particles. Certain types of particles coated with a capture molecule are commercially available from Sigma-Aldrich (St. Louis, MO).

Reference to binding of a target analyte to a capture molecule refers to members of a specific binding pair (or binding partners), which are moieties that specifically recognize and bind each other. Specific binding pairs are exemplified by a receptor and its ligand, enzyme and its substrate, cofactor or coenzyme, an antibody or Fab fragment and its antigen or ligand, a sugar and lectin, biotin and streptavidin or avidin, a ligand and chelating agent, a protein or amino acid and its specific binding metal such as histidine and nickel, substantially complementary polynucleotide sequences, which include completely or partially complementary sequences, and complementary homopolymeric sequences. Specific binding pairs may be naturally occurring (e.g., enzyme and substrate), synthetic (e.g., synthetic receptor and synthetic ligand), or a combination of a naturally occurring BPM and a synthetic BPM.

Target capture refers to selectively separating a target analyte from other components of a sample mixture, such as cellular fragments, organelles, proteins, lipids, carbohydrates, or other nucleic acids. Target capture as described herein means to specifically and selectively separate a predetermined target analyte from other sample components, e.g., by using a target specific molecule.

The term sandwich complex as used herein refers to a complex comprising a target analyte immobilized between a capture molecule on a substrate and a capture molecule coupled to a core particle that is associated with one or more metal ions. An exemplary sandwich complex is shown in FIG. 2. The sandwich complexes can be formed in competitive and non-competitive manners.

In a sandwich type non-competitive assay, the sample solution includes one or more target analytes (optionally in a purified form) and one or more of the reactants as described herein. The sample with the target analyte(s) may be mixed with the reactant(s) prior to introduction to the substrate or may be first introduced to the substrate before mixing with the reactant(s). That is, the sample and the reactant(s) may be applied sequentially or simultaneously to the substrate.

In a sandwich type competitive assay, the sample solution includes one or more target analytes (optionally in a purified form) and one or more of the reactants as described herein. The sample with the target analyte(s) may be mixed with the reactant(s) prior to introduction to the substrate or may be first introduced to the substrate before mixing with the reactant(s). That is, the sample and the reactant(s) may be applied sequentially or simultaneously to the substrate. However, in this format, the capture molecule(s) on the substrate are already bound to a molecule that must be displaced by the target analyte(s).

In the single-plex format, the first sandwich complex can be formed by introducing the sample comprising a first target analyte to the substrate comprising a first capture molecule that is specific to the first target analyte, wherein the first target analyte binds the first capture molecule; and introducing a first reagent to the substrate, the first reagent comprising (i) a core metal nanoparticle having a second capture molecule coupled thereto or (ii) a second capture molecule without a core metal nanoparticle; and one or more first metal particles coupled to the second capture molecule, wherein the first reagent binds the first target analyte via the second capture molecule to thereby form the first sandwich complex on the substrate. This can be done in a competitive or non-competitive manner. In certain embodiments, the first and second capture molecules are the same. In other embodiments, the first and second capture molecules are different.

In one multiplexed format, multiple different capture molecules are bound to a single layer of a substrate. In such an embodiment, the first sandwich complex is formed as described above. The second sandwich complex can be formed by introducing a second target analyte in the sample to the substrate comprising a third capture molecule that is specific to the second target analyte and different from the first capture molecule, wherein the third target analyte binds the second capture molecule; and introducing a second reagent to the substrate, the second reagent comprising (i) a core metal nanoparticle having a fourth capture molecule coupled thereto or (ii) a fourth capture molecule without a core metal nanoparticle; and one or more second metal particles coupled to the fourth capture molecule, wherein the one or more second metal particles are different from the one or more first metal particles and the second reagent binds the second target analyte via the fourth capture molecule to thereby form a second sandwich complex. In certain embodiments, the third and fourth capture molecules are the same. In other embodiments, the third and fourth capture molecules are different.

The first and second reagents may be introduced to the substrate in a single liquid or multiple liquids, with a single liquid being preferred.

In another multiplex format, the first and second sandwich complexes can be formed by introducing the sample comprising the first target analyte and the second target analyte to the substrate in a manner that the sample flows through the substrate, wherein the first target analyte binds the first capture molecule on the first layer and the second target analyte binds the second capture molecule on the second layer; introducing a first reagent to the substrate, the first reagent comprising (i) a core metal nanoparticle having a third capture molecule coupled thereto or (ii) a third capture molecule without a core metal nanoparticle; and one or more first metal particles coupled to the third capture molecule, wherein the first reagent binds the first target analyte on the first layer via the third capture molecule to thereby form the first sandwich complex; and introducing a second reagent to the substrate, the second reagent comprising (i) a core metal nanoparticle having a fourth capture molecule coupled thereto or (ii) a fourth capture molecule without a core metal nanoparticle; and one or more second metal particles coupled to the fourth capture molecule, wherein the second reagent flows through the first layer to the second layer and binds the second target analyte on the second layer via the fourth capture molecule to thereby form the second sandwich complex. This can be done in a competitive or non-competitive manner. In certain embodiments, the first and second capture molecules are the same. In other embodiments, the first and second capture molecules are different. In certain embodiments, the third and fourth capture molecules are the same. In other embodiments, the third and fourth capture molecules are different.

In still another multiplex format, each layer includes multiple different types and/or classes of capture molecules. In such an embodiment, the first and second sandwich complexes are formed as described above. The third sandwich complex may be formed by introducing the third target analyte in the sample to the first layer of the substrate comprising a fifth capture molecule that is specific to the third target analyte and different from the first and second capture molecules, wherein the third target analyte binds the third capture molecule on the first layer; and introducing a third reagent to the substrate, the third reagent comprising (i) a core metal nanoparticle having a sixth capture molecule coupled thereto or (ii) a sixth capture molecule without a core metal nanoparticle; and one or more third metal particles coupled to the sixth capture molecule, wherein the one or more third metal particles are different from the one or more first and second metal particles and the third reagent binds the third target analyte on the first layer via the sixth capture molecule to thereby form the third sandwich complex. In certain embodiments, the fifth and sixth capture molecules are the same. In other embodiments, the fifth and sixth capture molecules are different.

The first, second, and/or third reagents may be introduced to the substrate in a single liquid or multiple liquids, with a single liquid being preferred.

In certain embodiments, the directing and detecting steps of the methods of the invention described herein are accomplished one or more laser based systems, such as using Laser-Induced Breakdown Spectroscopy (LIBS) or Spark-Induced Breakdown Spectroscopy (SIBS). In certain embodiments, a single laser based system is employed. In certain embodiments, combinations of different laser based systems are contemplated. Laser-induced breakdown spectroscopy (LIBS) is a type of atomic emission spectroscopy which uses a highly energetic laser pulse as the excitation source. The laser is focused to form a plasma, which atomizes and excites samples. Spark-induced breakdown spectroscopy (SIBS) is a plasma-based atomic emission analytical technique that draws from both traditional spark spectroscopy and laser-induced breakdown spectroscopy (LIBS).

Figure 5:
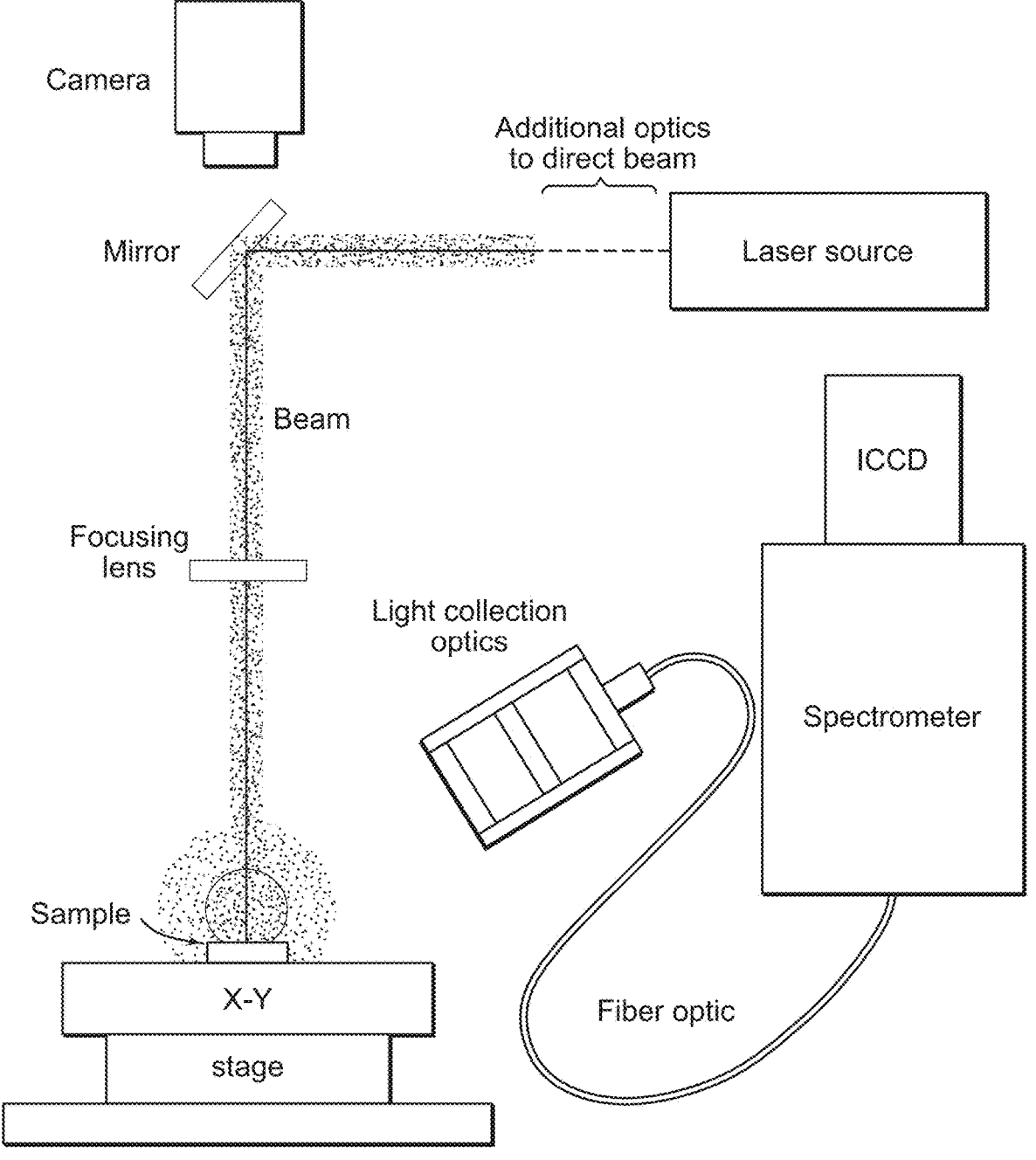
FIG. 5 is a diagram of LIBS system. An 18 mJ beam produced by NEWWAVE RESEARCH TEMPEST 1064 nm Q-switched laser (laser from NewWave Research) was directed to a sample using a series of optics. Sample position was adjusted using and X-Y stage. Plasma emissions were directed to a fiber optic connected to a spectrometer and ICCD detector. A camera was used for basic sample observation.

In certain embodiments, LIBS is employed for the directing and detecting steps. An exemplary LIBS system is shown in FIG. 5. Typically, LIBS systems are composed of 3 base components: a pulsed laser (such as a 100 uJ cobalt laser), laser focusing optics, point-source collection optics, and a spectrometer (with a CCD or ICCD detector). In certain embodiments, LIBS is performed in air, argon and helium environments to optimize plasma production.

Laser- and spark-induced breakdown spectroscopy (LIBS and SIBS) are sample characterization techniques based on the production and analysis of the fourth state of matter—ionic plasma. Plasmas produced during LIBS and SIBS emit complex optical emissions consisting of a continuous background spectrum and discrete line emissions representative of the elemental components of the sample.

When an energy pulse is applied to a solid substrate, the atoms in or near the path of the energy pulse are heated. If the heating is sufficient, the energy pulse is followed by a visible flash and popping sound generated by the rapid expansion of hot material and air. The expanding ionized gas is plasma, the fourth state of matter. The fraction of material that reaches the plasma-electron temperature threshold (~10 eV) forms a plume along the energy pulse path. Based on the spectral emission properties of the plume, one can characterize the composition of the source material. The nature of plasma formation and emission detection is highly dependent on certain parameters: (i) mode of induction, (ii) pulse duration, (iii) repetition rate, (iv) laser wavelength (if a laser is used), (v) time of analysis, (vi) environmental temperature, pressure, and atomic composition, (vii) physical properties of the substrate, and (viii) spatial distribution of the plasma. The effects of these parameters on plasmas can be explained by the physical principles of thermal and non-thermal energy absorption and dissipation over time.

LIBS is further described for example in Anabitarte et al. (ISRN Spectroscopy 2012:12, 2012); and Aragon et al. (Applied Spectroscopy 51(11):1632-1638, 1997), the content of each of which is incorporated by reference herein in its entirety.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes. The content of U.S. Ser. No. 15/510,319 is also expressly incorporated by reference herein in its entirety.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1: Ability of LIBS to Detect Anti-Toxin Heavy-Metal Conjugated Antibodies on a Substrate This example relates to determining LIBS parameters for detecting metal-conjugated antibodies on paper, detection of metal-conjugated antibodies using LIBS LA-ICP-OES, and bioassay design (materials and reagents).
LIBS System Parameters for Detecting Metal-Conjugated Antibodies on Paper The LIBS system as shown in FIG. 5 was employed in this work. As described herein, four LIBS systems were tested for detection of metal-conjugated antibodies on paper. System 1: 1064 nm laser, ~70 mJ, nanosecond pulse, 1 mm spot size, CCD detector air environment; System 2: 1064 nm laser, 50 µJ, nanosecond pulse, 30 µm spot size, CCD detector, air environment; System 3: 213 nm laser, 4 mJ, nanosecond pulse, 125 µm spot size, CCD and ICCD detector air environment; System 4: 1064 nm laser, 18 mJ, nanosecond pulse, 100 µm spot size, ICCD detector, air environment. System 4 was successful in detecting metal-conjugated antibodies on paper (FIG. 5).
Detection of Lanthanide-Complexed Antibodies Using LIBS Anti-*E. coli* antibodies were complexed to 5 types of lanthanides (Pr, Nd, Yb, Eu and Pr) using kits from Fluidigm. Metal-complexed antibodies were then loaded onto nitrocellulose paper (FF120HP, GE Lifesciences). LIBS was used to ablate the paper 15 times. Signal was accumulated across all ablation. Process was repeated for negative (blank paper) and positive (paper loaded with metal standards) controls. Metal was qualitatively detected by analyzing spectral lines reported by NIST and LA-ICP-OES. FIG. 7 illustrates treatments.

LIBS and LA-ICP-OES was performed on pregnancy tests to determine if gold nanoparticles that form the pink line of the test could be detected. As displayed in FIG. 8, two regions were sampled on each pregnancy test: the pink line, and the area adjacent to the pink line (negative control). The process was performed for wet and dry pregnancy tests. As a positive control, gold foil was used.
Bioassay Design—Materials and Reagents Cytodiagnostics bioassay cartridges were prepared by adding 1 µl of 1 mg/ml anti-mouse antibodies to 3 locations on the surface of nitrocellulose paper. The paper was then blocked using Universal Buffer (Cytodiagnostics).

Figure 6:
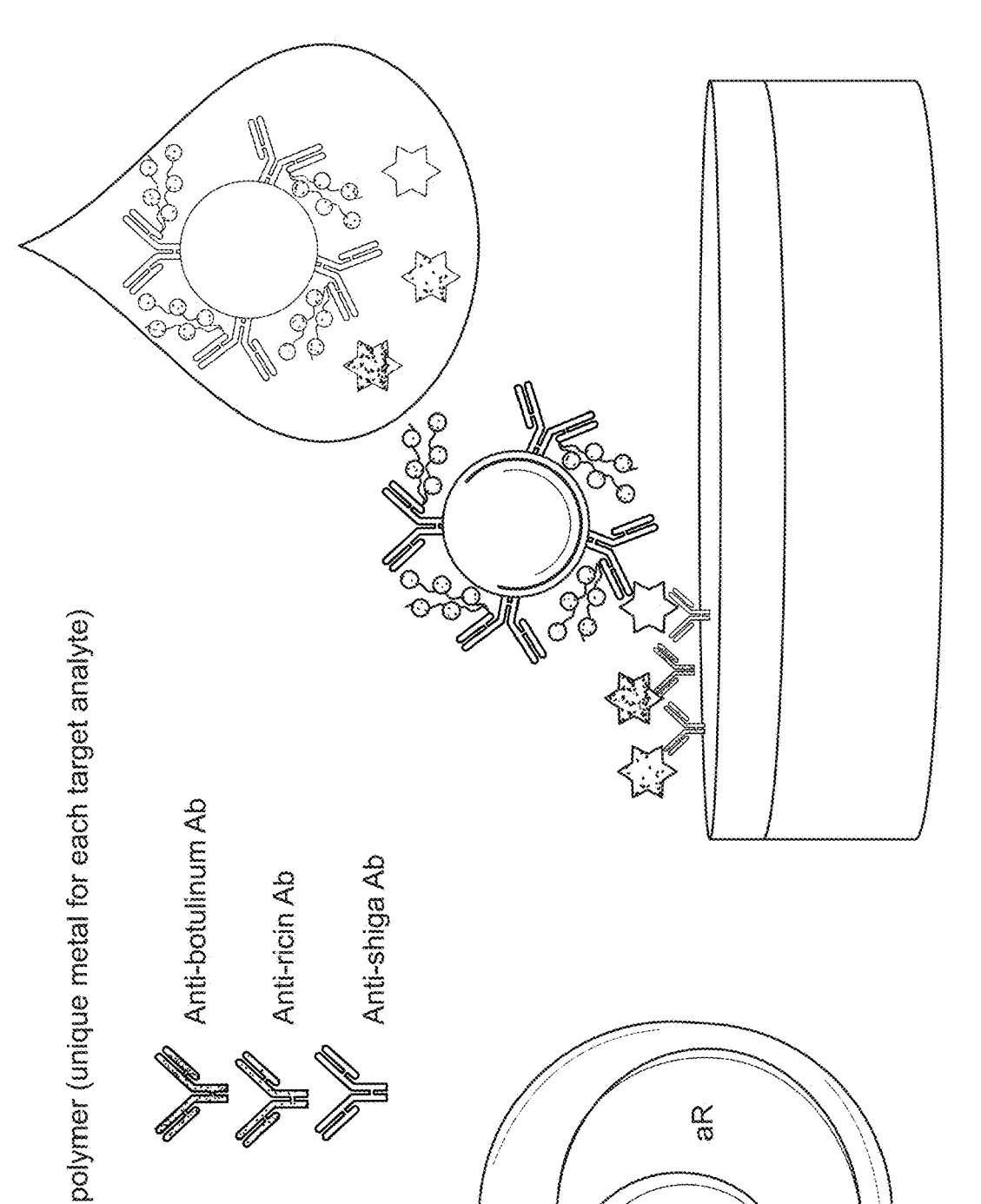
FIG. 6 shows a paper- and LIBS-based detection of metal-labeled analytes. A pink spot indicates the successful binding of analytes to the paper substrate.
Figures 8, 9:
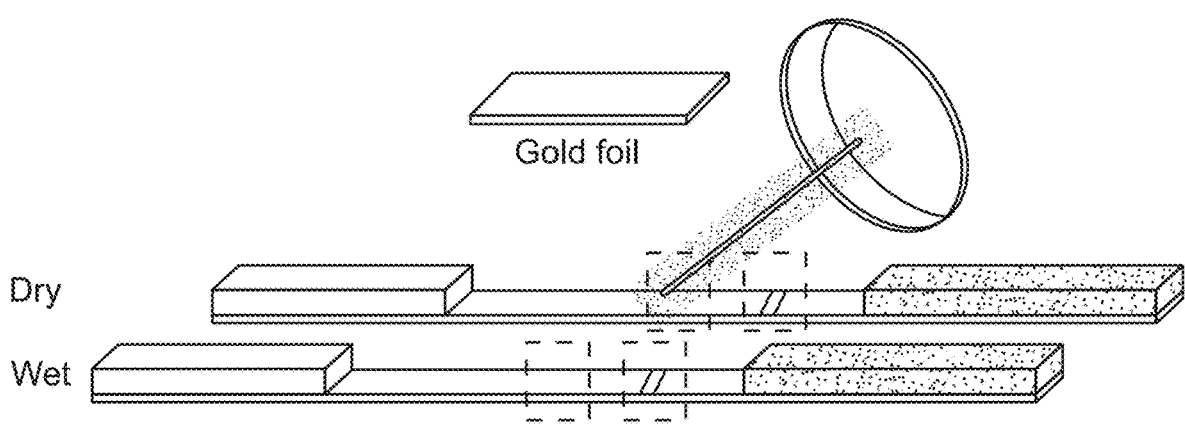
FIG. 8 is an illustration showing sampling of a pregnancy test.
FIG. 9 is an illustration showing anti-rabbit antibodies complexed to lanthanides that were conjugated to the surface of 20 nm particles using Cytodiagostics conjugation kit. 200 μl (0.4 OD) was then added to the cartridge.
Figure 10A:
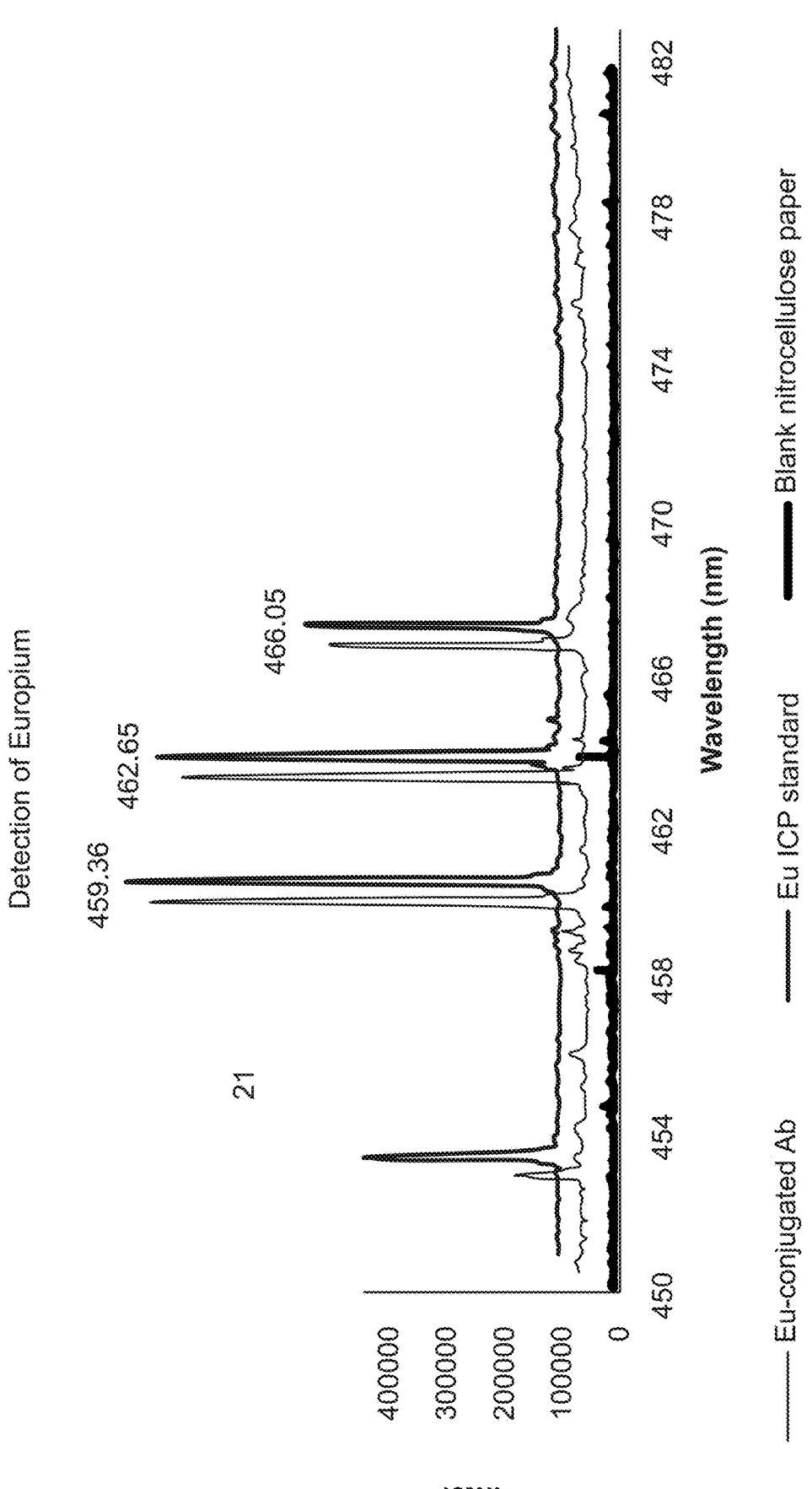
FIG. 10A shows the raw spectrum for Eu treatments as an example of the output.
Figures 10B, 10C:
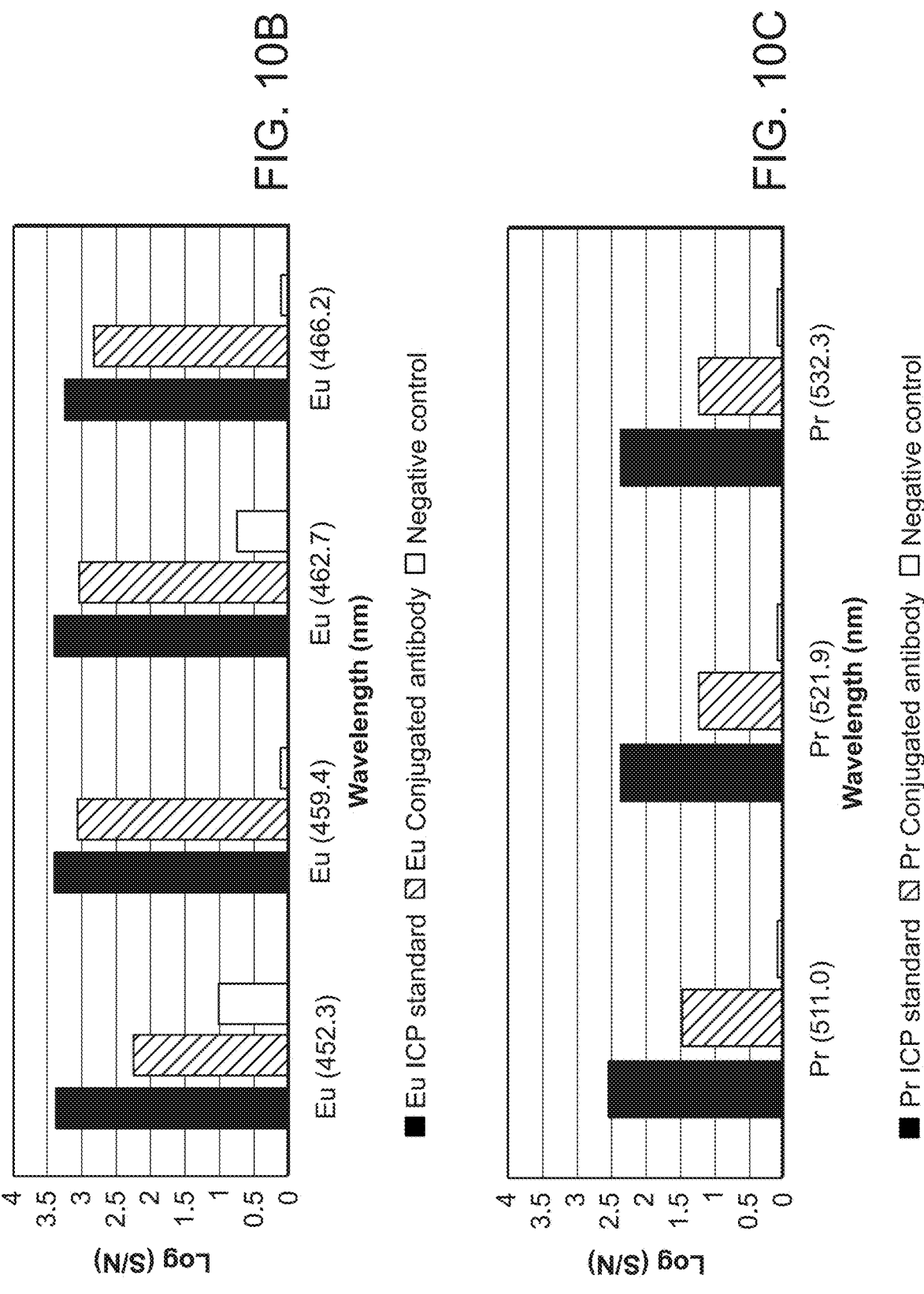
FIGS. 10B-F show results of LIBS that was performed on paper samples bearing Eu, Pr, Nd, Dy, and Yb. For each lanthanide, 3 treatments were tested: metal standards on paper, lanthanide-conjugated antibody on paper, and untreated paper.
Figures 10D, 10E:
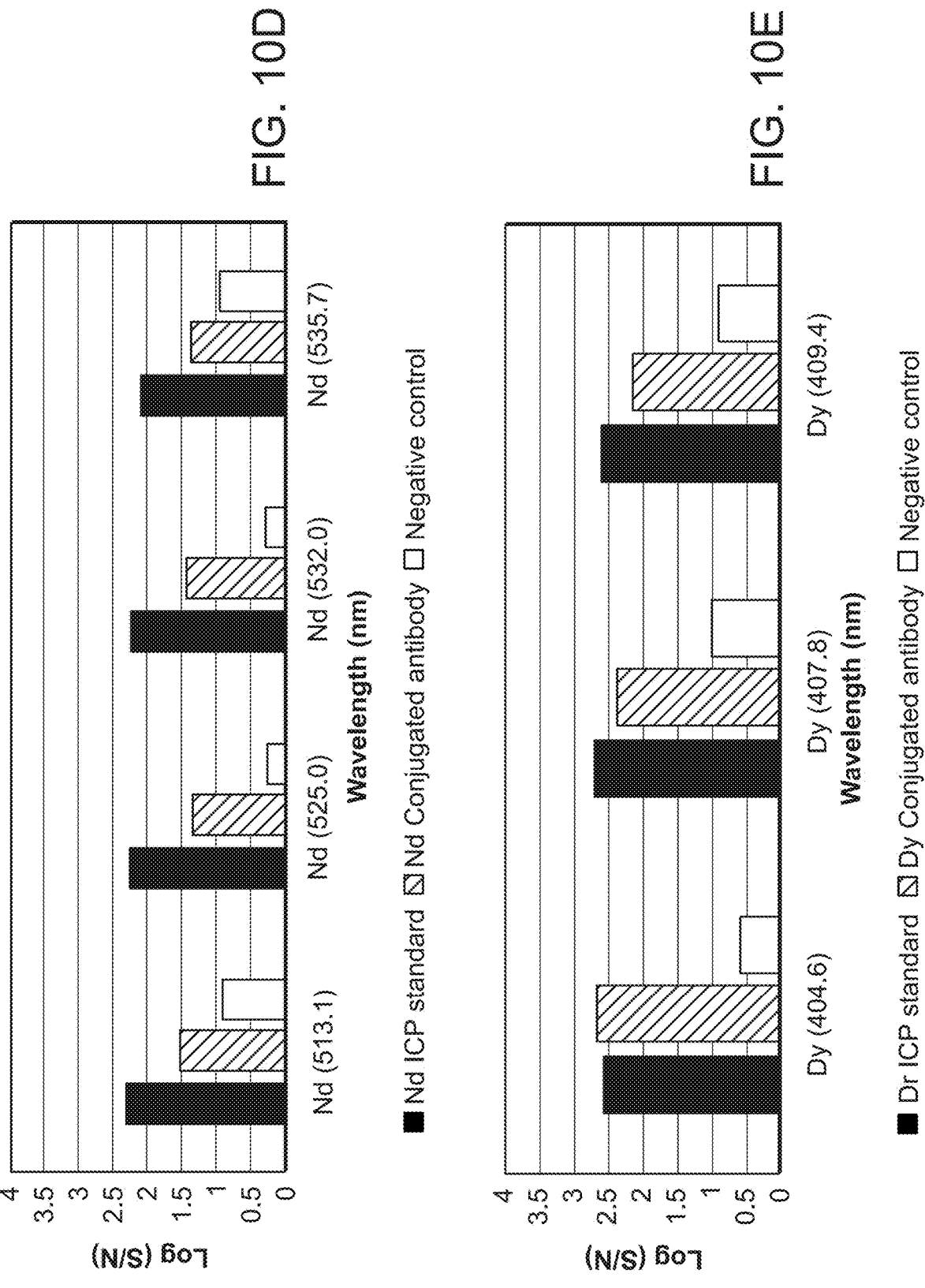
Figure 10F:
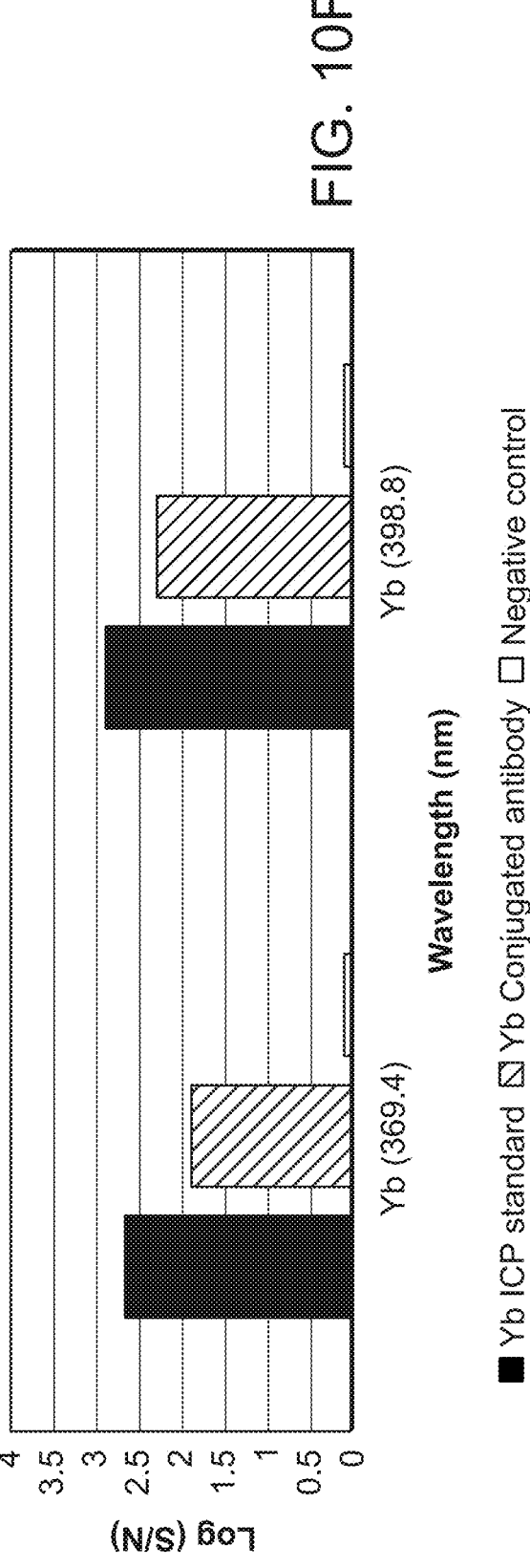

Anti-*E. coli* antibodies complexed to lanthanides were conjugated to the surface of 20 nm particles using Cytodiagostics conjugation kit. 200 µl (0.4 OD) was then added to the cartridge (FIG. 9). Cartridges were then rinsed with a wash buffer. Successful conjugation of the metal-complexed antibody to the gold nanoparticle was evaluated based on visual observation on a pink spot on the paper (FIG. 6).
Detection of Lanthanide-Complexed Antibodies Using LIBS LIBS was performed on paper samples bearing Eu, Pr, Nd, Dy, and Yb (FIGS. 10B-F). For each lanthanide, 3 treatments were tested: metal standards on paper, lanthanide-conjugated antibody on paper, and untreated paper. The raw spectrum for Eu treatments is displayed (FIG. 10A) as an example of the output. All samples were ablated 15 times in different locations. The 15 sampling events were aggregated, converted to S/N in log scale, and plotted. The plots show that for each lanthanide (except the 404.6 nm line of Dy (e)), the ICP standard produced the strongest signal, followed by the lanthanide conjugated antibody, and then the untreated nitrocellulose. The results show that LIBS can successfully detect lanthanide-conjugated antibodies on paper.

Figure 11A:
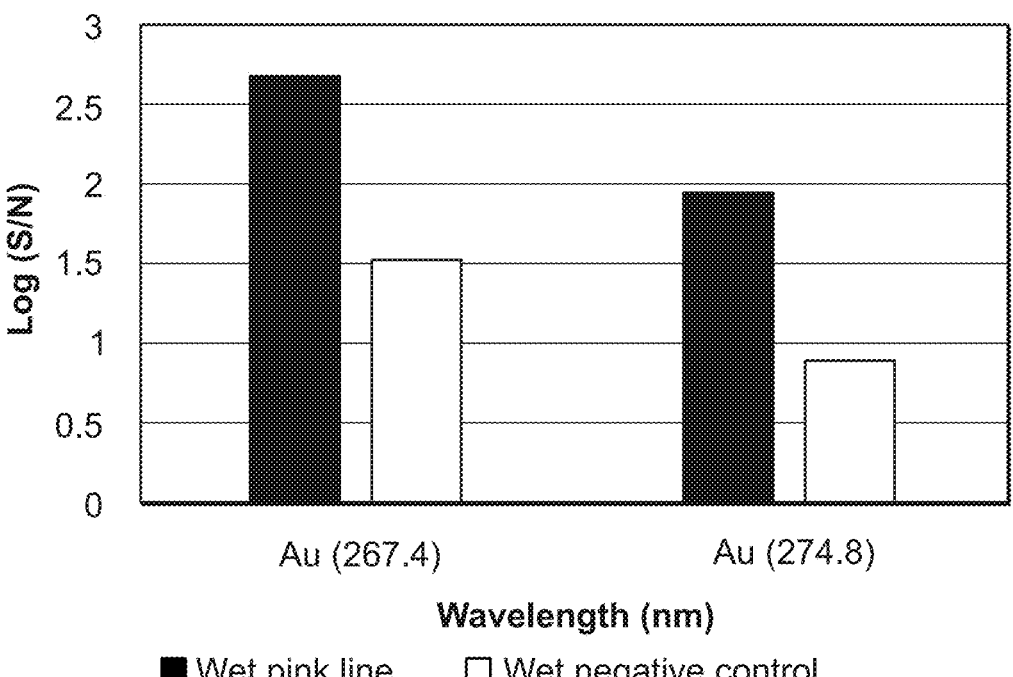
FIGS. 11A-B show results of LIBS that was performed on wet and dry pregnancy tests.
Figure 11B:
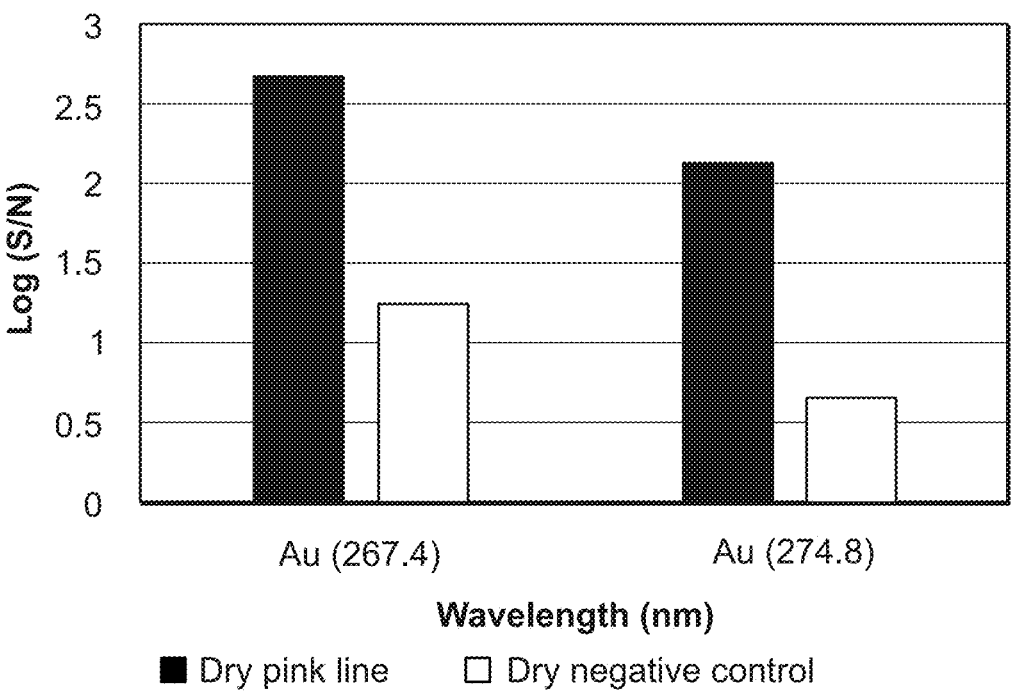
Figures 12A, 12B:
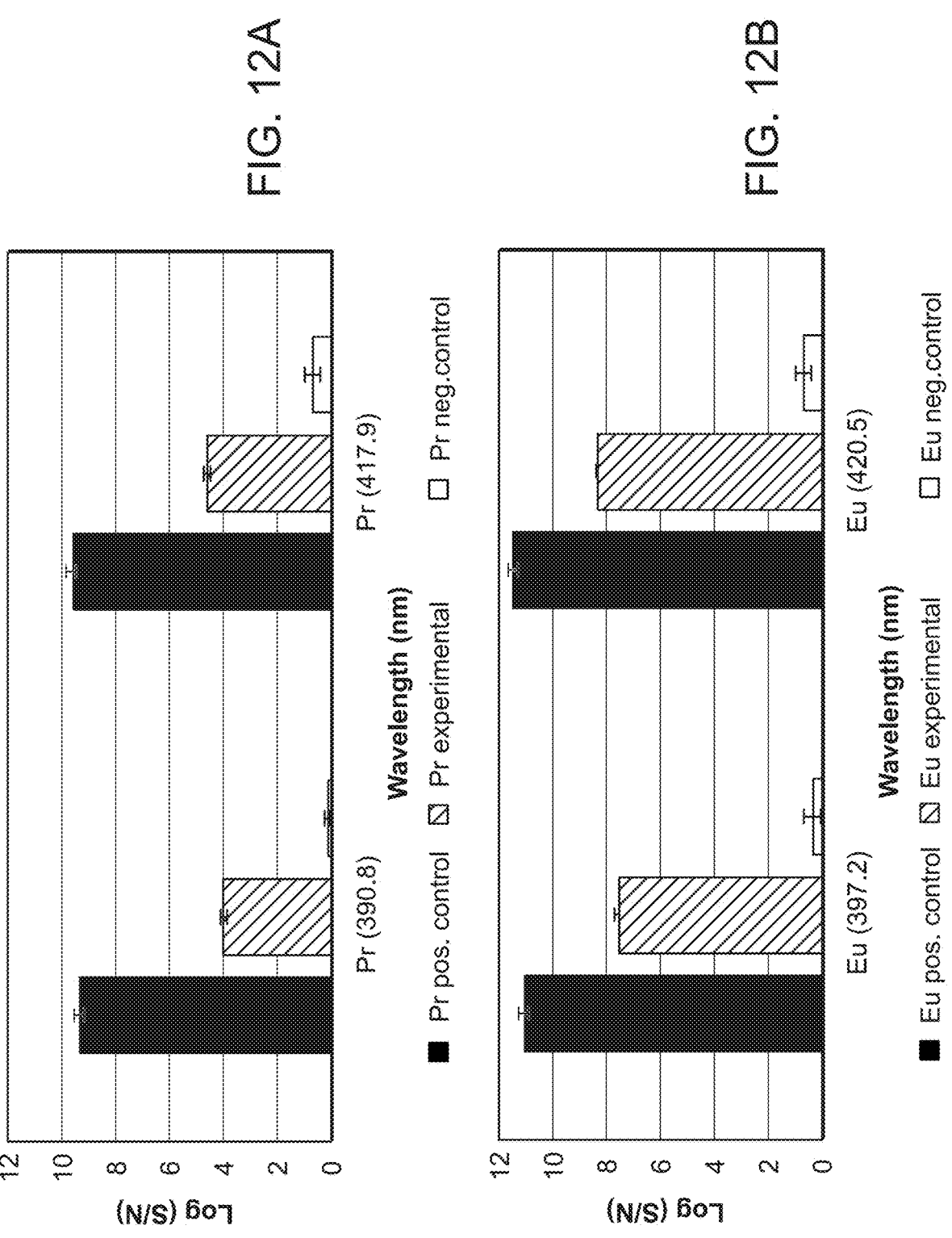
FIGS. 12A-D show results of tests using LA-ICP-OES as a supporting analytical method. The trends observed in LA-ICP-OES analysis were similar to those obtained by LIBS.
Figures 12C, 12D:
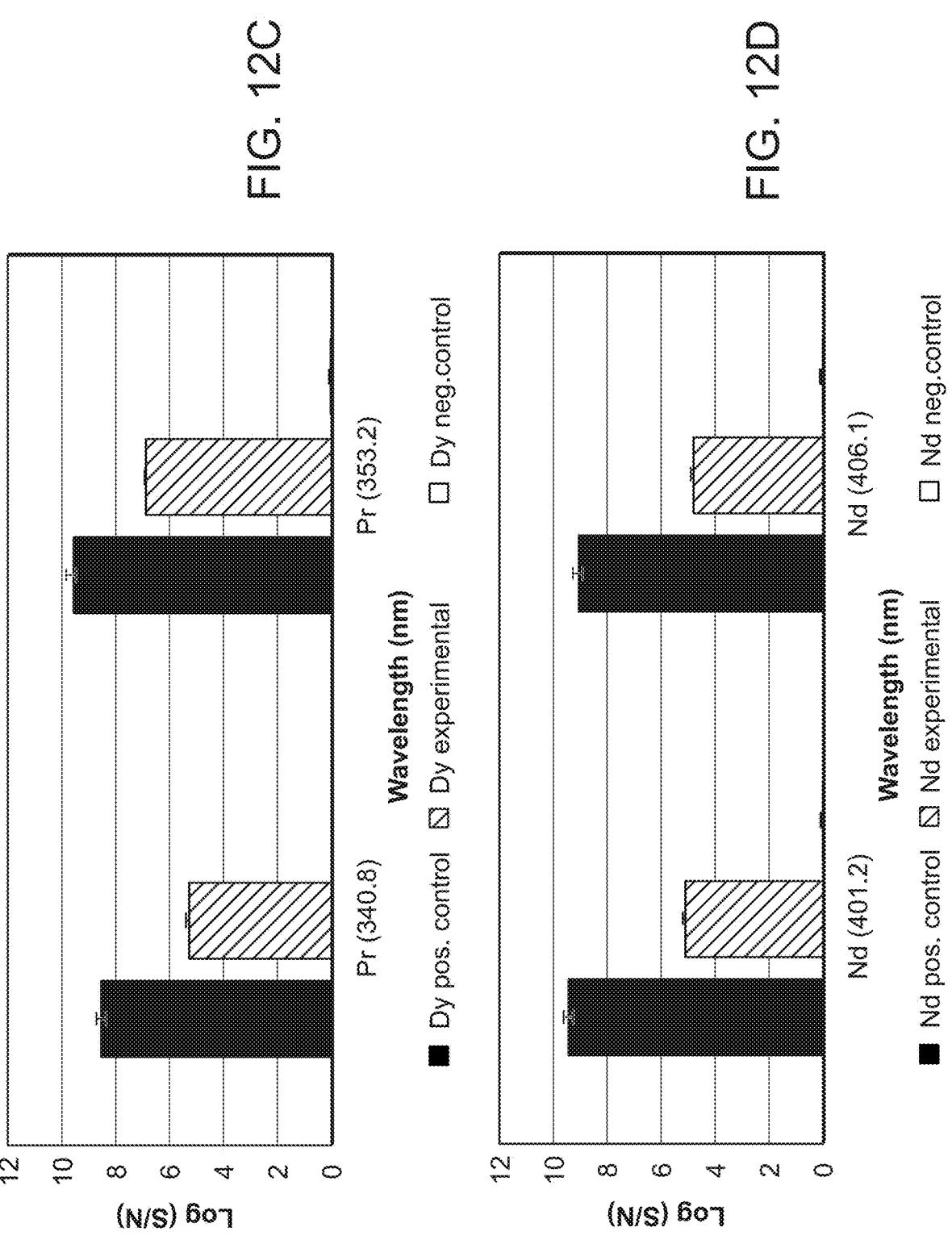

LIBS was also performed on wet and dry pregnancy tests. Each pregnancy test was sampled in 2 locations: the area of high nanoparticle aggregation (pink line), and the area adjacent to the pink line. Gold emissions from the pink line are stronger than those adjacent to the pink line (FIGS. 11A-B). The results show that LIBS can detect gold nanoparticles conjugated to antibodies on nitrocellulose.

Figure 13:
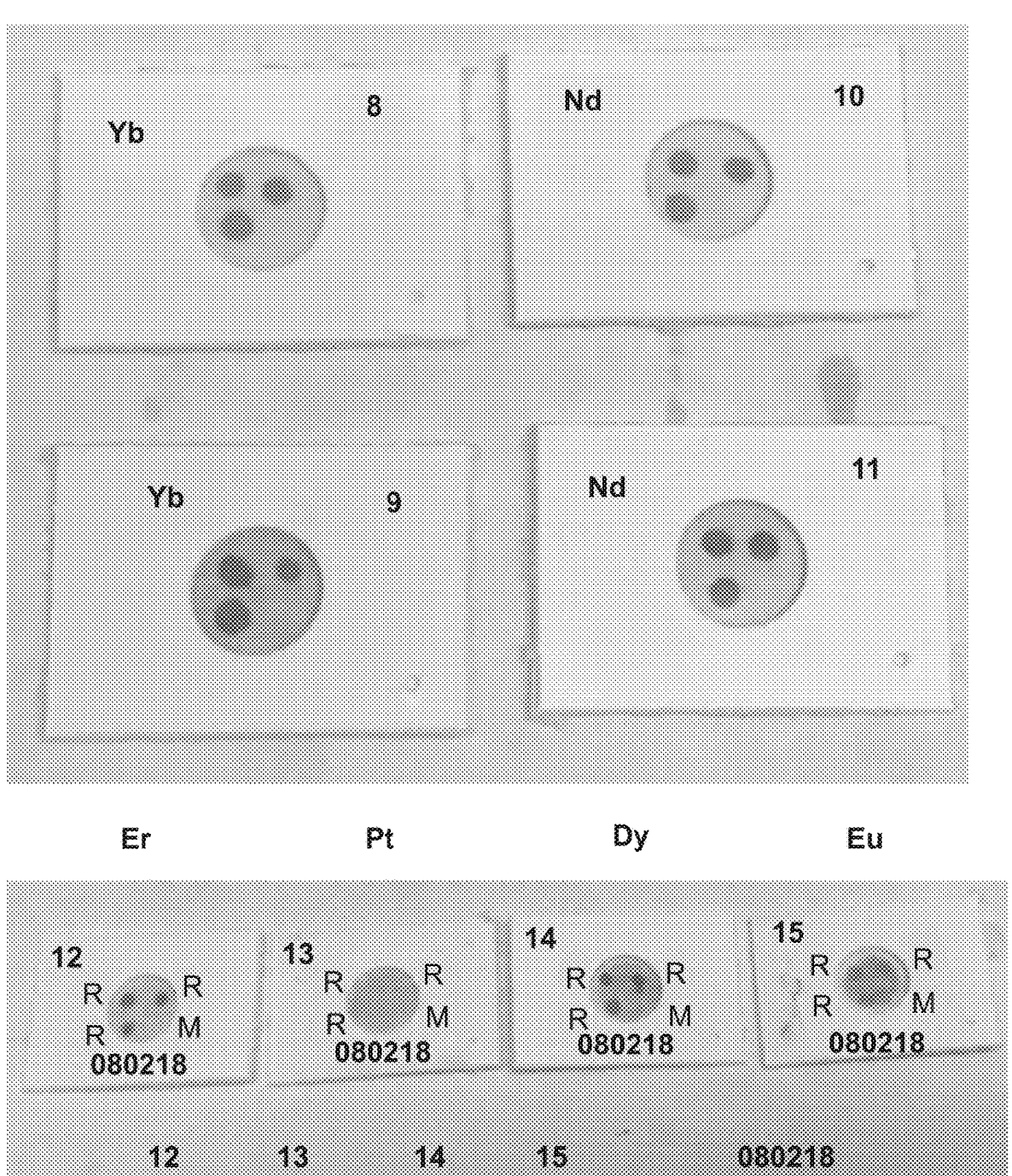
FIG. 13 shows vertical flow-assay cartridges that were used to determine if antibodies complexed to lanthanides could be conjugated to 20 nm gold nanoparticles. The pink spots displayed show successful conjugation for Yb, Nd, Er, Pt, Dy and Eu complexed antibodies.

Samples that were tested with LIBS were also tested using LA-ICP-OES as a supporting analytical method. The trends observed in LA-ICP-OES analysis were similar to those obtained by LIBS (FIGS. 12A-D). The positive control produced the strongest signal for each metal, followed by the experimental treatment and negative control. Only data for Pr, Eu, Dy and Nd are displayed. Au detection displayed a similar trend (data not shown). For technical reasons, Yb treatments were not tested. Results obtained with LA-ICP-OES support those obtained with LIBS.
Bioassay Design—Materials and Reagents Vertical flow-assay cartridges were used to determine if antibodies complexed to lanthanides could be conjugated to 20 nm gold nanoparticles. The pink spots displayed in FIG. 13 displays successful conjugation for Yb, Nd, Er, Pt, Dy and Eu complexed antibodies. The results show that lanthanide-complexed antibodies can be conjugated to gold nanoparticles.
Conclusion The results herein show successful development of a biosensor consisting of two major components: a bioassay that uses paper and metal-conjugated antibodies to concentrate and label an analyte, and LIBS as the bioassay analysis tool. This study determined that a 1064 nm laser with an 18 mJ pulse focused to a spot of 100 µm was appropriate for detecting metal-conjugated antibodies on paper. The results were supported using LA-ICP-OES. To advance the bioassay, lanthanide-complexed antibodies were conjugated to gold nanoparticles. Conjugation was validated using an immuno-dot-blot test.

Example 2: Detection of Metal-Conjugated Antibodies Using Laser-Induced Breakdown Spectroscopy and Laser-Ablation Optical Emission Spectroscopy This example shows the use of applying laser-induced breakdown spectroscopy (LIBS) for the analysis of paper-based biological assays (PBBs) that utilize metals to label biomolecules of interest. LIBS and PBBs are proven field-deployable rapid-detection technologies. Gold, silver and latex nanoparticles conjugated to probes such as antibodies are a common method for detecting biomolecules of interest using PBBs, in part due to optical properties that are easily discernable with the naked eye. However, this limited panel of biomolecular labels places limitations on the diversity of biomolecules that can be detected simultaneously in a single PBB. Simultaneous field-deployable detection of a diversity of biomolecules in a single test is of interest in scenarios concerning biohazard outbreaks in areas without fast access to proper lab facilities. Examples would be food production and distribution facilities, or remote locations/individuals subjected to a bioterrorism attack. For such applications, this example shows expansion of the panel of biomolecular labels used for field-deployable PBBs by implementing LIBS as the analytical tool. A wide diversity of metal bio-tags exist, and a few have been applied to PBBs. However, the detection schemes vary depending on the form or element—some are detected via luminescence, others through absorbance. Detection of these metal labels can also be achieved through mass analysis, however the instrumentation requirements do not make the technology amenable for rapid field-deployable analysis. This example shows use LIBS as a single measurement technique to detect the many elements used for bio-tagging. In this preliminary work, antibodies conjugated to Yb, Nd, Pr, Eu, Dy and Au are absorbed onto nitrocellulose paper (a common material for PBBs) and detected using LIBS. Laser-ablation inductively coupled plasma optical emission spectroscopy is also used, and aids in supporting the results obtained with LIBS. This study pioneers the combination of LIBS, PBBs and metal-conjugated antibodies as a future field-deployable, highly multiplexed and rapid bio-detection tool.

Introduction

This example presents a study exploring the application of laser-induced breakdown spectroscopy (LIBS) for detection of metal-conjugated antibodies on paper bioassay platforms. Central to the study is the combination of three technologies: paper-based bioassays, metal-conjugated antibodies, and LIBS.

Figure 14:
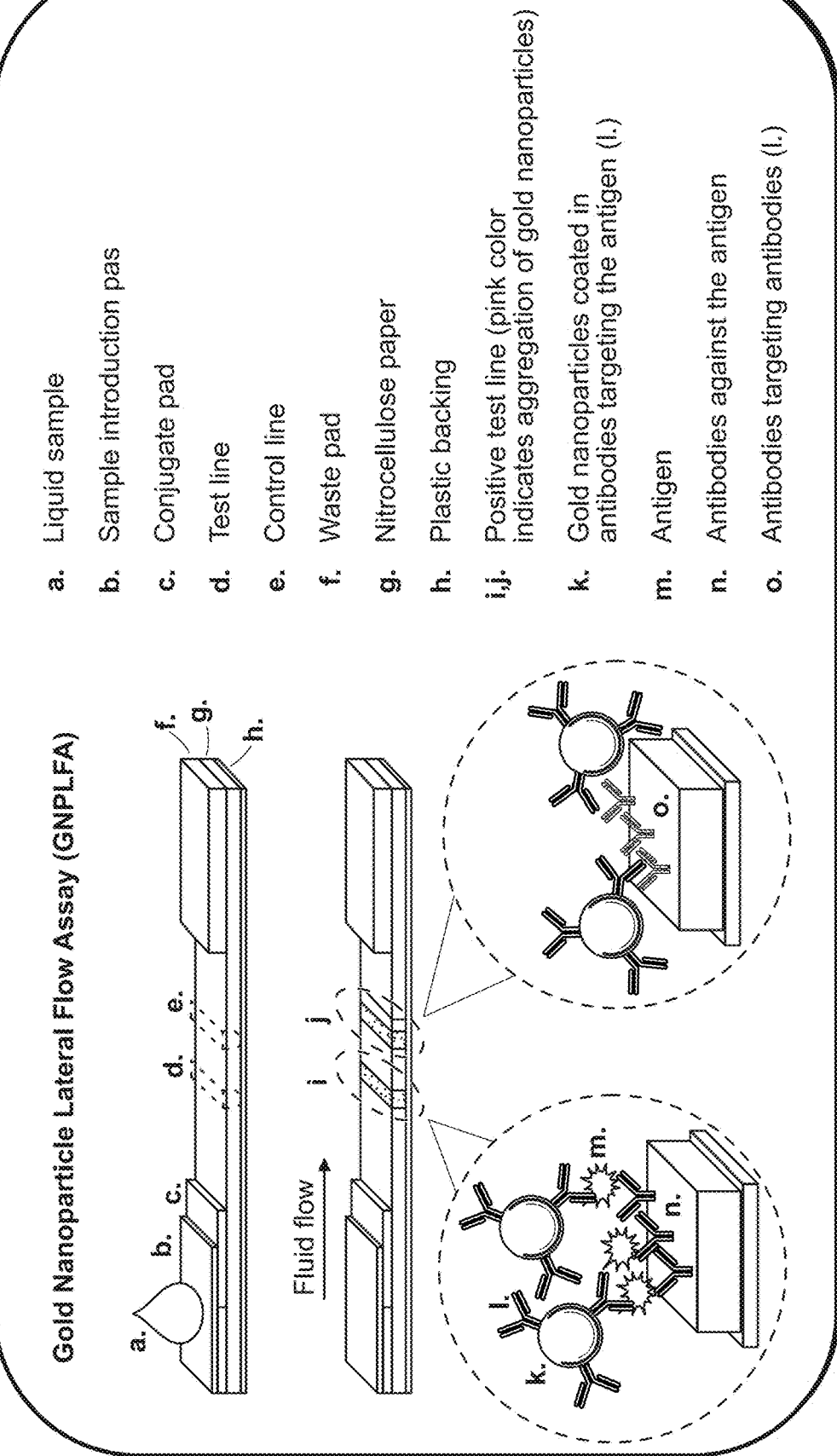
FIG. 14 is an illustration showing 1. Sample (a.) is introduced to the strip (b.) and mixes with gold nanoparticles coated in detection antibodies (1.). The sample then wicks along the nitrocellulose paper (g). When the sample interacts with the test line (d.), if the antigen is present, gold nanoparticles that have bound to the antigen aggregate at the test line (i.). When sample interacts with the control line (e.) nanoparticles that are not bound to the antigen aggregate at the control line (j.). Excess sample and unused reagents are absorbed by the waste pad (f).

Paper-based bioassays (PBB) have become popular as field-deployed diagnostic tools because they are simple, portable and low-cost. A common example is the pregnancy test which utilizes gold nanoparticles (GNPs) coated in anti-pregnancy hormone antibodies for colorimetric detection. FIG. 14 illustrates the design of a general pregnancy test. The lateral-flow assay design is common among PBBs across a variety of applications. Many PBBs are designed to allow untrained users to acquire the test at a low cost and perform the test independently. PBBs often utilize GNPs coated in detection antibodies targeting an analyte of interest. As displayed in FIG. 14, when a liquid sample is applied to the PBB, GNPs interact with the sample, flow through the paper, and aggregate in certain regions, producing a visible pink line. These regions are often termed the test line and control line. Aggregation of GNPs on the test line indicates to the user that the analyte is present, and aggregation of GNPs on the control line indicates that the test is functioning properly. Similar PBBs have been applied to the detection of influenza, phenylketonuria, toxins and other biomolecules.

It was previously believed that multiplexed PBBs are less common than single-plexed PBBs because of limitations in the number of antibody labels available, sample volume required, reagent chemistry, and the complexity of portable detection instrumentation. The examples herein illustrate otherwise. Antibodies are typically used in biosciences to tag or immobilize specific biomolecules. Often, antibodies are conjugated to labels that give them contrast against the background biological matrix. Common labels among PBBs are latex, silver and gold nanoparticles which can be detected visually based on color. Other common labels are fluorophores which can be detected through a process of excitation and emission. Fluorescent antibodies have been widely used for biomolecular detection because of their specificity and excellent signal to noise capacity, and have been applied to paper-based bioassays. However, when multiple probes are used, they suffer from overlapping emission profiles, short life-times, background effects, and require multiple excitation sources and detectors for sensitive multiplexed detection. These features make it challenging to develop fluorescence detection instrumentation that is sensitive, portable, low cost, and multiplexed.

This study expands the panel antibody labels for paper-based bioassays, creating opportunities for highly multiplexed and portable assay development. This study shows polymer-complexed metal isotopes (primarily lanthanides) that are conjugated to antibodies, creating a new type of antibody label. An example of detection instrumentation used in biosciences to detect metal labels is mass spectrometry, inductively coupled plasma mass spectrometry, and mass cytometry—typically used for highly multiplexed analysis of immune cells. The size, cost and sample preparation requirements of mass spectrometry instruments precludes their transition into the field of low-cost or portable bio-assay analysis technologies. An alternative to mass spectrometry is luminescence detection of lanthanide antibody labels. This method has been applied to detecting biomolecules conjugated to lanthanide nanoparticles in paper assays. However, some of the limitations that apply to fluorescent antibody detection (portability of instrumentation and multiplexing capability) can be extended to detection of luminescent lanthanide labels.

This example shows use LIBS as a method to detect lanthanide-conjugated bio-labels on paper. LIBS offers the potential of greater multiplexing than luminescent means, and may be a more portable and cost effective alternative than mass spectroscopy. LIBS is a technique for element identification and relies on the generation and spectral analysis of an ionic plasma. While it originated as a bench-based instrument, it has recently been developed into a hand-held product, predominantly applied to characterization of soils and sheet-metals. See Rakovský et al., Spectrochimica Acta Part B: Atomic Spectroscopy 2014, 101, 269-287), the content of which is incorporated by reference herein in its entirety.

The application of LIBS for detecting metal-conjugated antibodies in paper is novel and relevant because it opens opportunities for portable and multiplexed detection of biological analytes. In this example we show the use of a bench-based LIBS instrument to detect metal-conjugated antibodies on nitrocellulose paper.

Instrumentation

Figure 15:
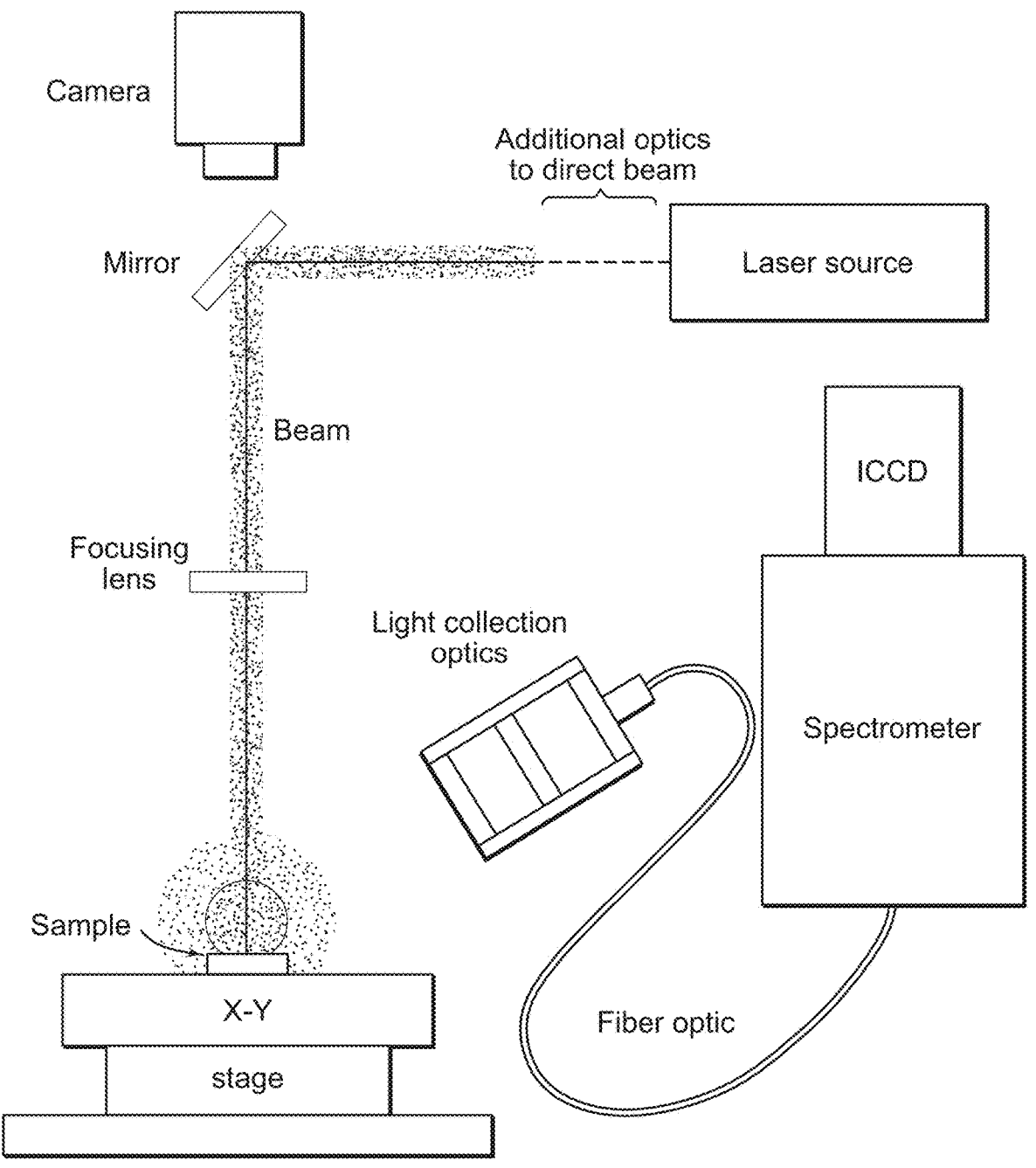
FIG. 15 shows a diagram of LIBS system. An 18 mJ beam produced by NEWWAVE RESEARCH TEMPEST 1064 nm Q-switched laser (laser from NewWave Research) was directed to a sample using a series of optics. Sample position was adjusted using and X-Y stage. Plasma emissions were directed to a fiber optic connected to a spectrometer and ICCD detector. A camera was used for basic sample observation.

FIG. 15 illustrates the design of the LIBS system. LIBS instrumentation consisted of a NEWWAVE RESEARCH TEMPEST 1064 nm Q-switched laser (laser from NewWave Research). Pulse energy was 18 mJ, with a pulse duration of 3-5 ns. The beam was focused to a spot size of ~100 μm on the sample. The sample was observed using a camera whose focal plane was the same as that of the 100 μm laser spot. A collimating lens and fiber optic directed the LIBS spectral emission to a Princeton Instrument 320-mm ISOPLANE SCT spectrograph (imaging spectrometer from Teledyne Princeton Instruments fitted with a Princeton Instruments PI-MAX (Intensified CCD camera) ICCD detector (Princeton Instruments, Acton, MA, U.S.A). The spectra were acquired for 20 μs, 1 μs after the laser pulse. The sample was positioned near the focal point of the beam using an x,y,z stage. Controls and experimental samples, described in more detail below, consisted of gold nanoparticle lateral flow assays, untreated nitrocellulose paper, and nitrocellulose paper treated with either ICP standards or lanthanide-conjugated antibodies.

As a secondary method of analysis, laser ablation inductively coupled plasma optical emission spectroscopy (LA-ICP-OES) was performed using Applied Spectra J200 (Applied Spectra, Fremont, CA, U.S.A) coupled to an Agilent 5100 ICP-OES (Agilent, Santa Clara, CA, U.S.A) system.

Samples were ablated with a 213 nm 4 mJ beam focused to a spot size of 125 μm. Ablated particulates were carried to the ICP-OES system using argon or helium gas at a flow rate of 0.5 L/min. In the process of ablation, measurements were continuously being made, creating signal intensity vs. time data for each element being measured. Using the Agilent ICP-OES software, emission lines of metals used for antibody conjugation (Au, Dy, Pr, Eu and Nd) were selected for measurement.

For both LIBS and LA-ICP-OES analysis, the general experimental approach was to 1) use a positive control (either a liquid or solid standard) to identify atomic emission lines of elements of interest. Emission lines were cross-validated with the National Institute of Standard and Technology atomic database; 2) determine background emissions produced by the paper sample carrier; and 3) evaluate whether the experimental sample produced atomic emission lines for elements of interest above background levels. LA-ICP-OES was used to support results obtained by LIBS.

Gold-Nanoparticle Paper-Based Assay Preparation and Testing

As a proof of concept, off-the-shelf pregnancy tests (Wondfo Pregnancy Test strips, Wondfo W1-S, Guangzhou, China) were used to determine whether LIBS and ICP-OES showed promise as method for detecting metal-conjugated antibodies on paper.

The positive control consisted of 99.95% gold foil (Alfa Aesar 7440-57-5, Tewksbury, MA, U.S.A). LIBS was performed on the foil to identify prominent atomic emission lines which correspond to those reported by NIST.

To prepare the experimental sample and negative control, water was added to one end of the pregnancy test strip for three seconds according to the manufacturer's instructions. The process was repeated for multiple strips. A single pink line was observed to form on each strip, approximately 41 mm from the submerged end of the strip. The pink line served as the experimental sample, since the color is attributed to the aggregation of gold nanoparticles. The negative control consisted of the white area of paper adjacent to the pink line, 39-40 mm from the end of the strip.

Figure 16:
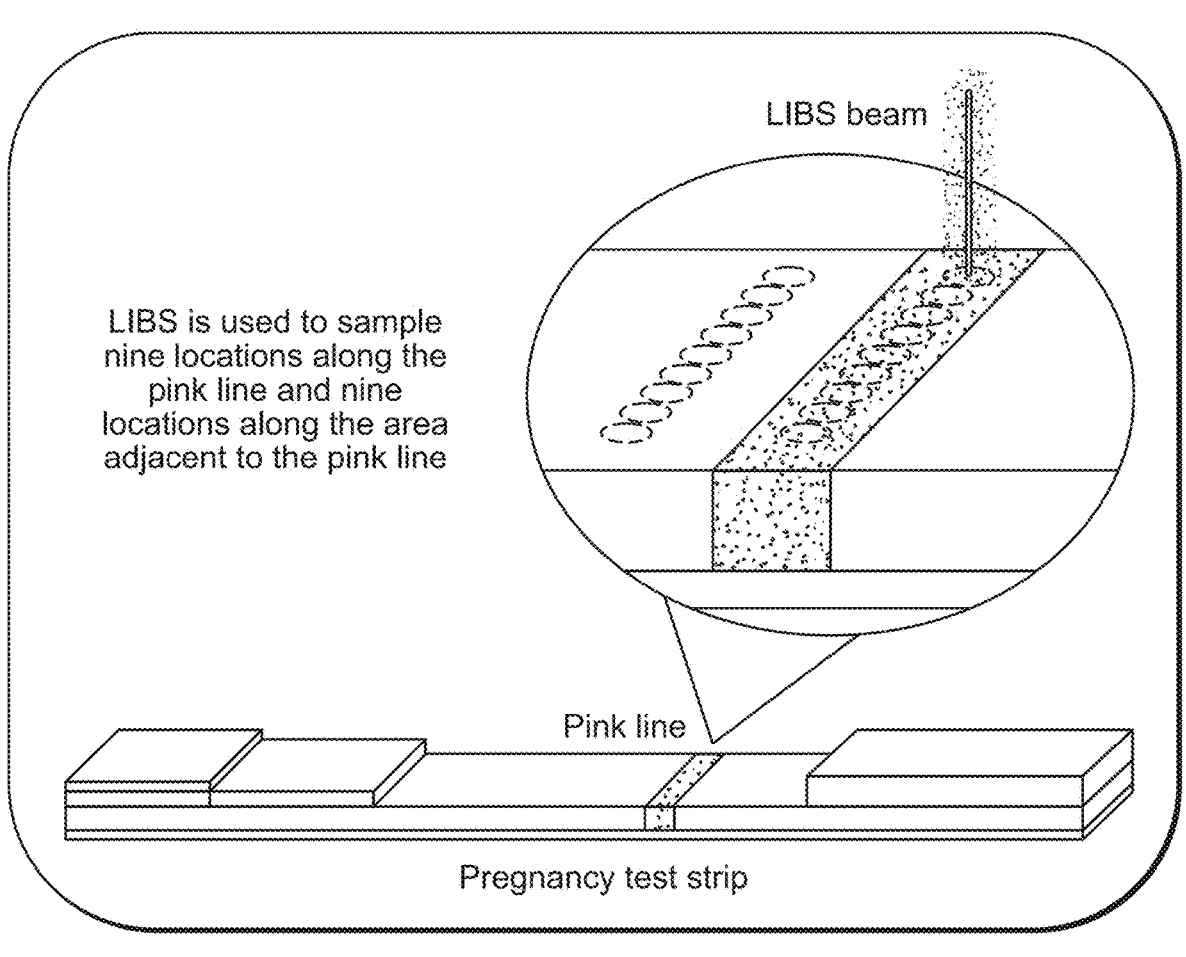
FIG. 16 is an illustration of the LIBS sampling approach for pregnancy test strips.

LIBS was performed on the pink line to determine the number of laser pulses that yielded a detectable gold signal. Three locations were sampled, each location experiencing ten pulses. The results suggested that a single pulse per location was sufficient, therefore a single pulse per location was used for all the following samples presented in this paper. Three strips were prepared as described above and allowed to dry overnight. For each strip, nine locations along the pink line were sampled. This sampling method was also used for the area adjacent to the pink line (FIG. 16). To determine whether wet strips would produce a comparable gold signal to dry strips, LIBS was performed on three strips immediately after they were immersed in water. Dry strips and wet strips were sampled similarly.

As a secondary method to determine the presence of gold on paper, LA-ICP-OES was performed on four dried pregnancy strips. The pink line was ablated in 4 rounds—each round consisting of 65 ablation pulses, one per location. The same sampling method was used for areas adjacent to the pink line. Argon gas was used as the carrier for the particulates. Au emission lines recommended by Agilent's ICP-OES software database were analyzed (208.2, 242.8 and 267.6 nm).

Lanthanide-Conjugated Antibody Preparation and Testing

After testing for gold-conjugated antibodies on paper using LIBS and LA-ICP-OES, a similar experiment was performed on lanthanide-conjugated antibodies.

Anti-*E. coli* antibodies (Abcam ab137967, Cambridge, MA, U.S.A) were conjugated to Eu, Nd, Dy, Yb and Pr using the Fluidigm MAXPAR metal labeling kit (Fluidigm, San Francisco, CA, U.S.A; antibody binding kit). Final antibody concentration was 0.4 mg/ml for Eu, Nd, Dy, Yb and Pr conjugated antibodies respectively. Based on previous studies, each antibody was anticipated to be conjugated to 2-3 polymers, each polymer bearing ~30 metal atoms. Experimental samples were prepared by adding 2 μl of each antibody stock solution to five 6 mm×3 mm cutouts of FF120HP plastic-backed nitrocellulose paper (GE Healthcare and Life Sciences, Pittsburgh, PA, U.S.A). This type of paper was chosen because it is common among PBBs.20 The antibody solution was observed to distribute across the entire paper and dried overnight.

Before performing LIBS on antibody conjugates, lanthanide emission lines were located using a positive control. The positive controls consisted of ICP standards containing either Eu, Nd, Dy, Yb or Pr (VHG Labs Inc. PEUN-100, PNDN-100, PDYN-100, PYBN-100, PPRN-100, Teddington, Middlesex, UK). A total volume of 240 μl of each standard (1000 ug/ml suspended in 2% nitric acid) was dried onto ~25×25 mm sections of FF120HP in aliquots of 60 ul. Negative control samples consisted of FF120HP with no additives. LIBS was performed on each positive and negative control sample using 15 laser pulses per sample (1 pulse per location). The same method was applied to experimental samples.

The positive control, negative control, and experimental samples used for the LIBS experiments were then used for LA-ICP-OES to further evaluate the presence of lanthanides. Each sample was ablated in 4 rounds—each round consisting of 30 ablation pulses, one per location. Helium was used as the carrier gas. Lanthanide emission lines recommended by Agilent's ICP-OES software database were analyzed: Dy (340.8 nm and 353.2 nm), Eu (397.2 and 420.5 nm), Nd (401.2 and 406.1 nm), and Pr (390.8 and 417.9). Due to technical reasons, LA-ICP-OES analysis of samples containing Yb were omitted from this portion of the study.

Peak Identification

Peaks were identified by first acquiring a broad spectrum (250-550 nm) of the positive controls. For each element of interest, the region with the most intense and well-resolved spectral peaks was then selected for analysis. Using the NIST Atomic Spectra Database (Ralchenko et al., (20) Sciences, G. H., 2013, the content of which is incorporated by reference herein in its entirety) reported emission lines from the metal of interest were cross-checked with the observed peaks in the positive control. To be selected for analysis, peaks in the positive control needed to be of high relative intensity, match reported lanthanide or gold peaks in the NIST database, and be absent from the negative control.

Data Analysis

A common method for element detection among LIBS studies is to measure signal-to-noise ratio of a specific emission line. Noise calculations are often based on the area adjacent to the emission line. In the case of spectra with a low density of emission lines, this approach is practical. However, in the analysis of high density spectra, such as those produced by some lanthanides, this approach may yield inaccurate results. As an alternative, the presented data was analyzed using the following procedure.

LIBS spectra were analyzed in R statistical package. Data was first accumulated for each sampling event. The noise was calculated across the wavelength range using a sliding median, and then subtracted from the raw data. This function leveled the data. The mean of a second sliding median was then subtracted from the raw data, centering the data on the x-axis. The output was then divided by the noise, defined as the second median's standard deviation, providing a measure of signal-to-noise (abbreviated as S/N) for LIBS. For samples of gold nanoparticles on nitrocellulose, S/N represents an aggregation of 27 measurements. For each lanthanide on nitrocellulose, S/N represents an aggregation of 15 measurements.

LA-ICP-OES raw data was reported as intensity vs. time for select wavelengths. Shortly following each round of ablations, the signal for carbon (a common element in nitrocellulose paper) peaked. LA-ICP-OES intensities for metals of interest at the time-point where carbon peaked were converted to S/N. Noise was considered as emission intensity reported by the instrument before laser ablation. Standard deviation of the noise was then divided from the signal, yielding S/N. The S/N from the four ablation rounds were averaged, and log-transformed. This process was applied to positive control, negative control, and experimental samples.

LIBS and LA-ICP-OES Analysis of Gold-Nanoparticles in Nitrocellulose Paper

Figure 17:
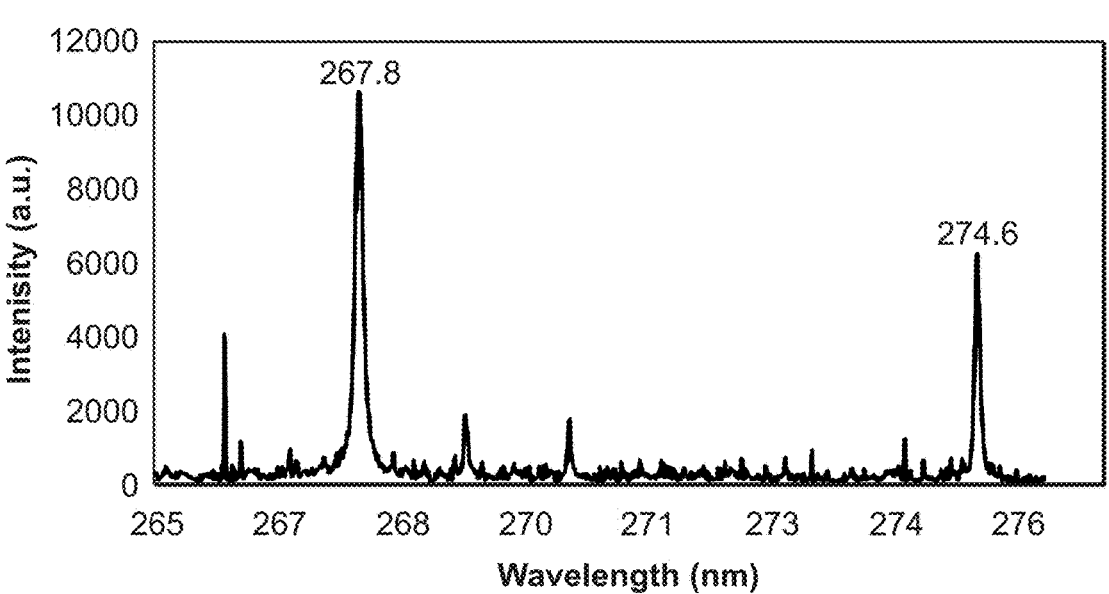
FIG. 17 is a spectrum of gold foil. Gold emission lines, as indicated by NIST, were identified at 267.8 nm and 274.6 nm.

Gold foil was utilized as the positive control for LIBS experiments on gold nanoparticle detection. Ablation of gold foil yielded strong emission peaks at 267.6 nm and 274.8 nm (532 and 315 S/N respectively) (FIG. 17). Peaks were identified as gold using the NIST database.

Figure 18:
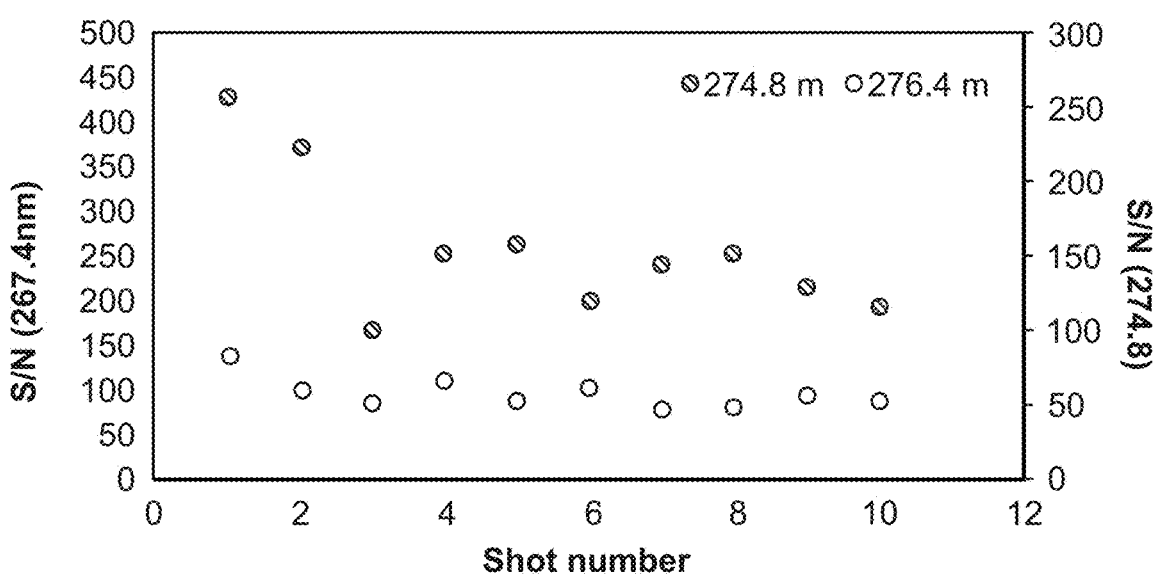
FIG. 18 shows degradation of gold emission lines 267.4 and 274.8 nm as the pink line of a pregnancy test strip was sampled 10 times in the same location. Each data point represents the average of 3 measurements. Standard deviation ranged from 7.7-38.8%.
Figure 19A:
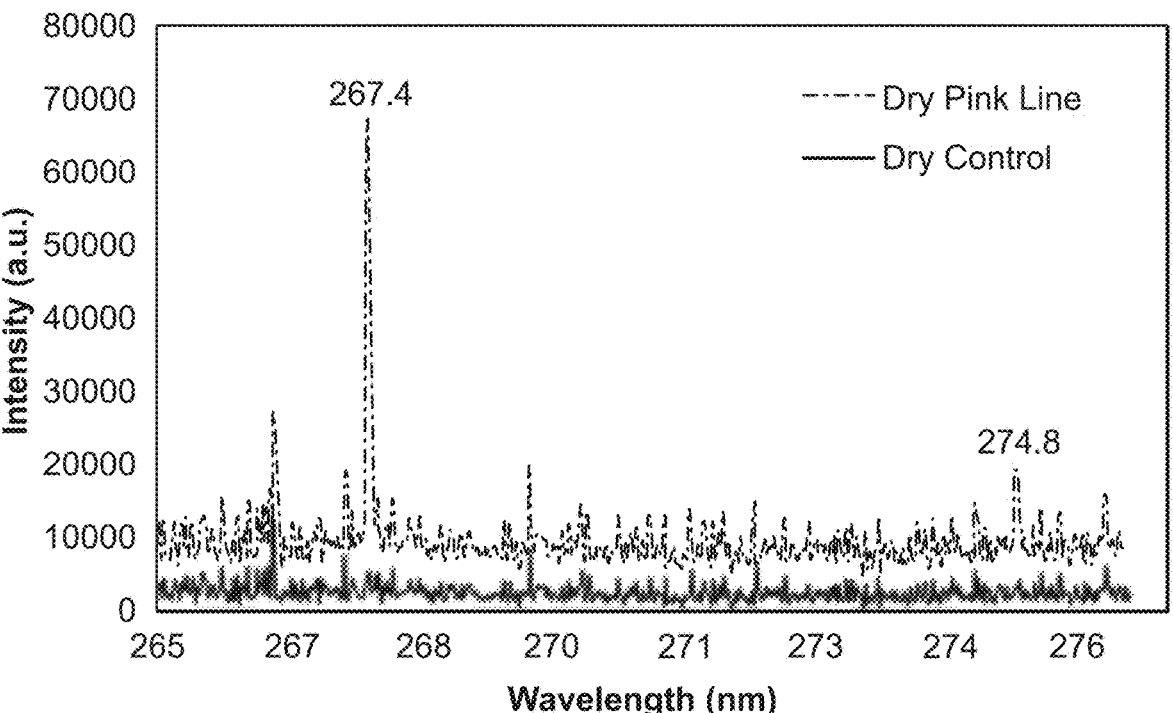
FIGS. 19A-B show water was added to eight pregnancy test strips. Four were immediately tested with LIBS (FIG. 19A) and the remaining were dried prior to sampling (FIG. 19B). For both wet and dry pregnancy test strips, gold emissions were observed where the pink line was sampled, and not observed in the area adjacent to the pink line (control). Each data point represents an aggregate of 27 measurements.
Figure 19B:
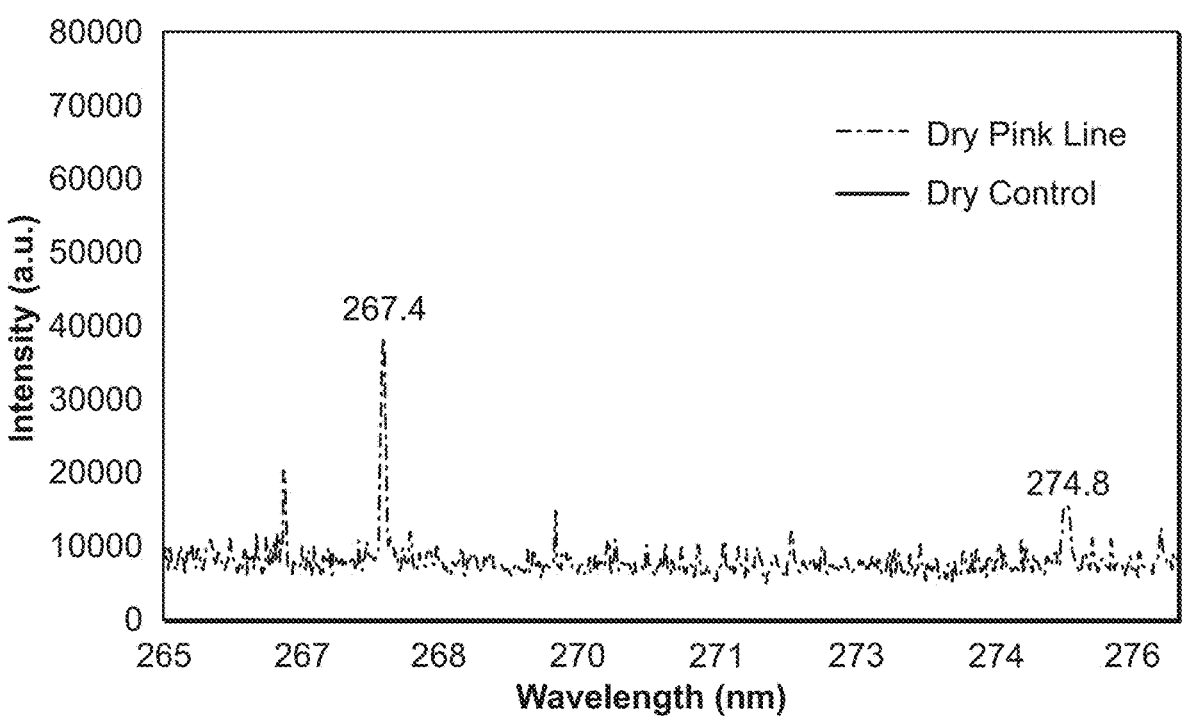
Figure 20A:
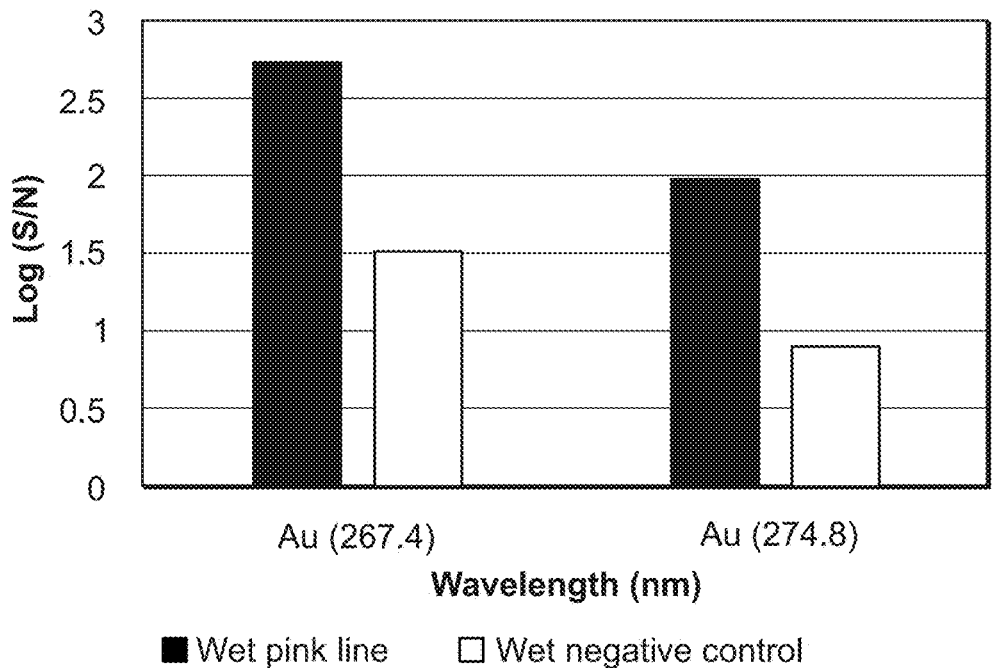
FIGS. 20A-B show water was added to pregnancy test strips. Three were immediately sampled with LIBS (FIG. 20A) and the three were dried prior to sampling (FIG. 20B). Two sections (the pink line and area adjacent to the pink line) of each pregnancy test strip were ablated 9 times each. Data on gold emission lines from the same sections of each pregnancy test were aggregated (27 measurements), converted to log of S/N, and plotted. Plot shows that the pink line produced a stronger gold emission line than the area adjacent to the pink line.
Figure 20B:
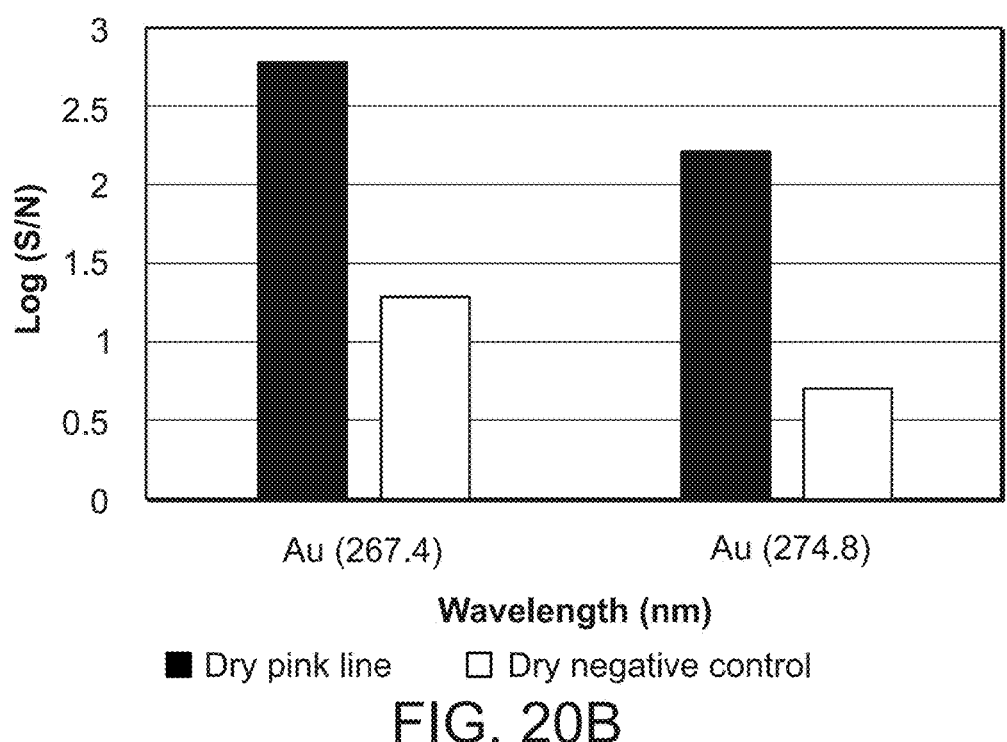

A study was conducted to determine the number of pulses required to obtain a detectable gold signal from paper without ablating through the material. When ablating the same location of a pink line on a pregnancy test with a series of 10 pulses, it was observed that average signal intensity at 267.6 nm and 274.8 nm degraded (FIG. 18) for each of the 3 tested areas. The plastic backing of the paper was visible after 5-10 laser pulses. Based on this information, all other samples composed of nitrocellulose in this study were ablated once per location. Differences between gold emission intensity were measured between wet and dry nitrocellulose paper. Wet and dry pregnancy tests were sampled in two locations: the pink line (area of high gold nanoparticle aggregation), and the area adjacent to the pink line (area of low nanoparticle aggregation, defined as the negative control). The raw LIBS spectra are presented in FIGS. 19A-B. The pink line on both the wet and dry pregnancy tests yielded comparable S/N at 267.6 nm (dry: 474 S/N; wet: 475 S/N) and 274.8 nm (dry: 127 S/N; wet: 84 S/N). The area adjacent to the pink line (negative control) on wet and dry samples yielded lower gold line S/N for each wavelength (267.6 nm—dry: 23 S/N; wet: 37 S/N) (274.8 nm—dry: 7 S/N; wet: 8 S/N). For both wet and dry samples, emission at 267.6 nm were stronger than those at 274.8 nm. Data is graphically presented in FIGS. 20A-B, and S/N values are provided in Table 1.

TABLE 1

Signal to noise ratio was measured for gold emissions lines 267.6 and 274.8 nm among three types of samples: gold foil, dry pregnancy test strips and wet pregnancy test strips. The gold foil positive control showed strong the highest S/N, followed by the pink line, and then the area adjacent to the pink line (negative control)

| | | Dry Pregnancy Test (S/N) | | Wet Pregnancy Test (S/N) | |
|---|---|---|---|---|---|
| Wavelength (nm) | Gold foil (S/N) | Pink Line | Adjacent to pink line | Pink Line | Adjacent to pink line |
| 267.6 | 532 | 574 | 20 | 520 | 34 |
| 274.8 | 315 | 160 | 5 | 93 | 8 |

Overall, the pink line yielded the strongest gold emission intensities, followed by the area adjacent to the pink line. Results are based on a limited sample size.

Figure 21:
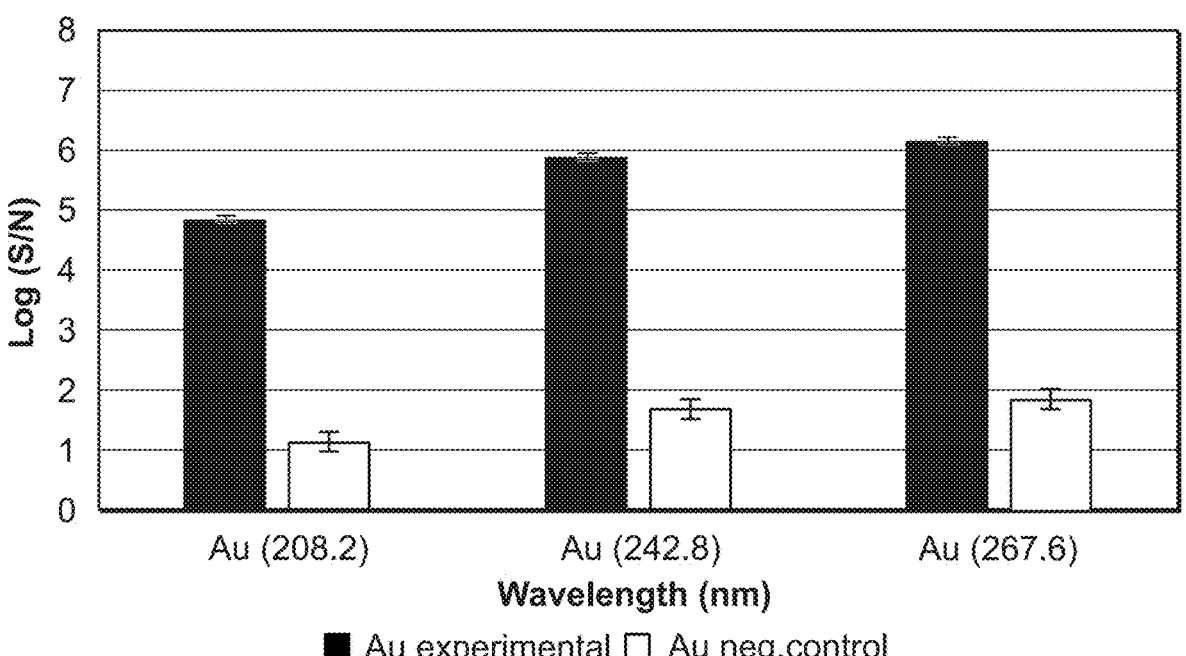
FIG. 21 shows LA-ICP-OES that was performed on dry pregnancy test strips. The pink line on the strip produced stronger gold emissions at 208.2, 242.7 and 267.5 nm compared to the area adjacent to the pink line.
Figures 22A, 22B:
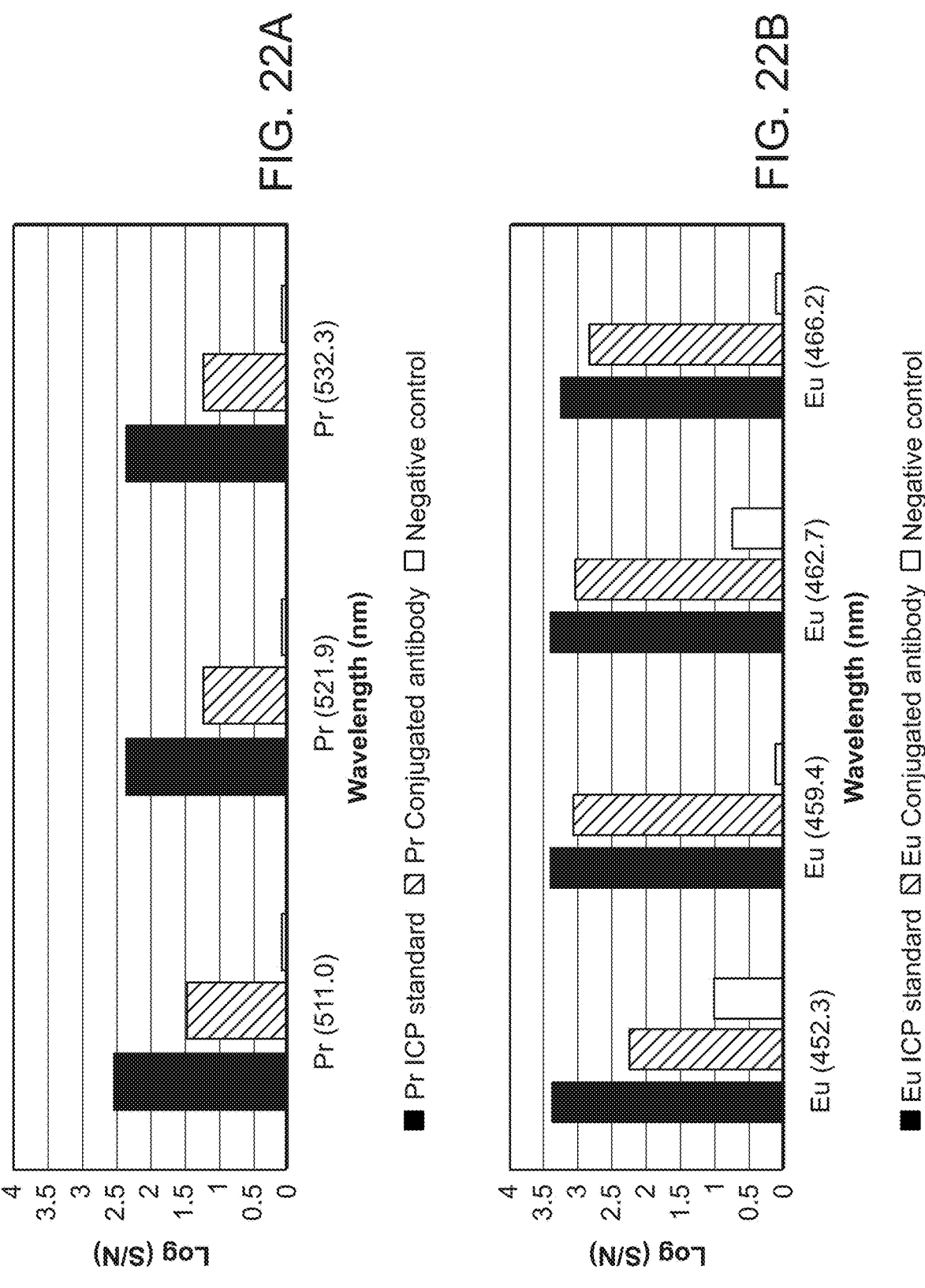
Figure 22E:
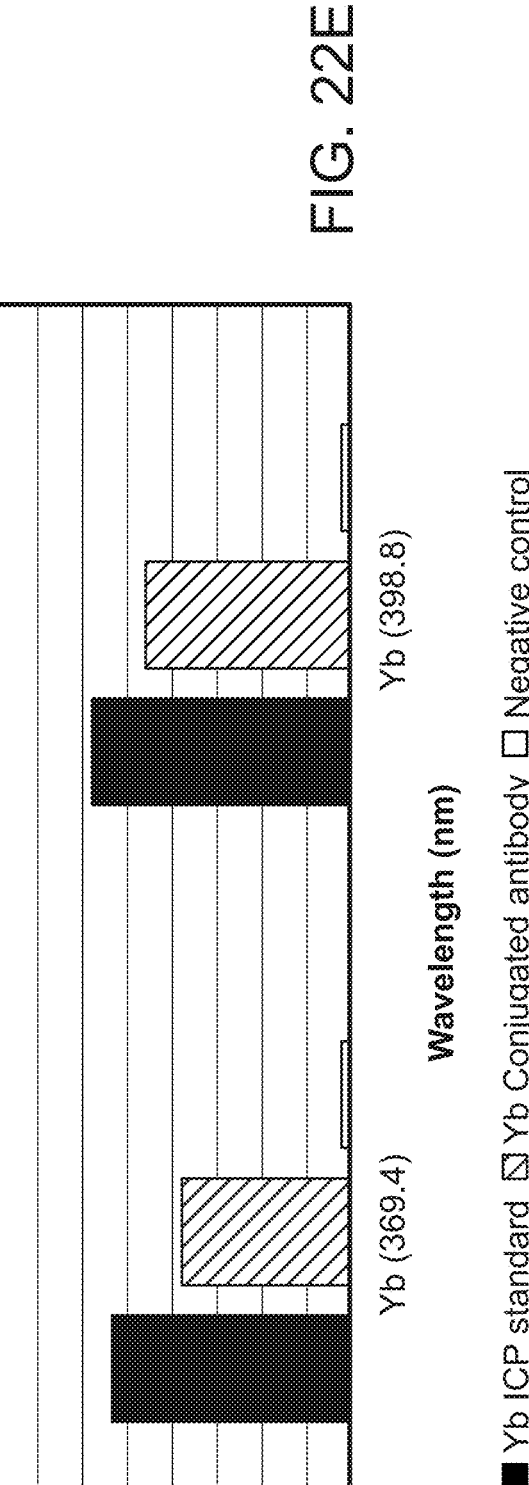
Figures 23A, 23B:
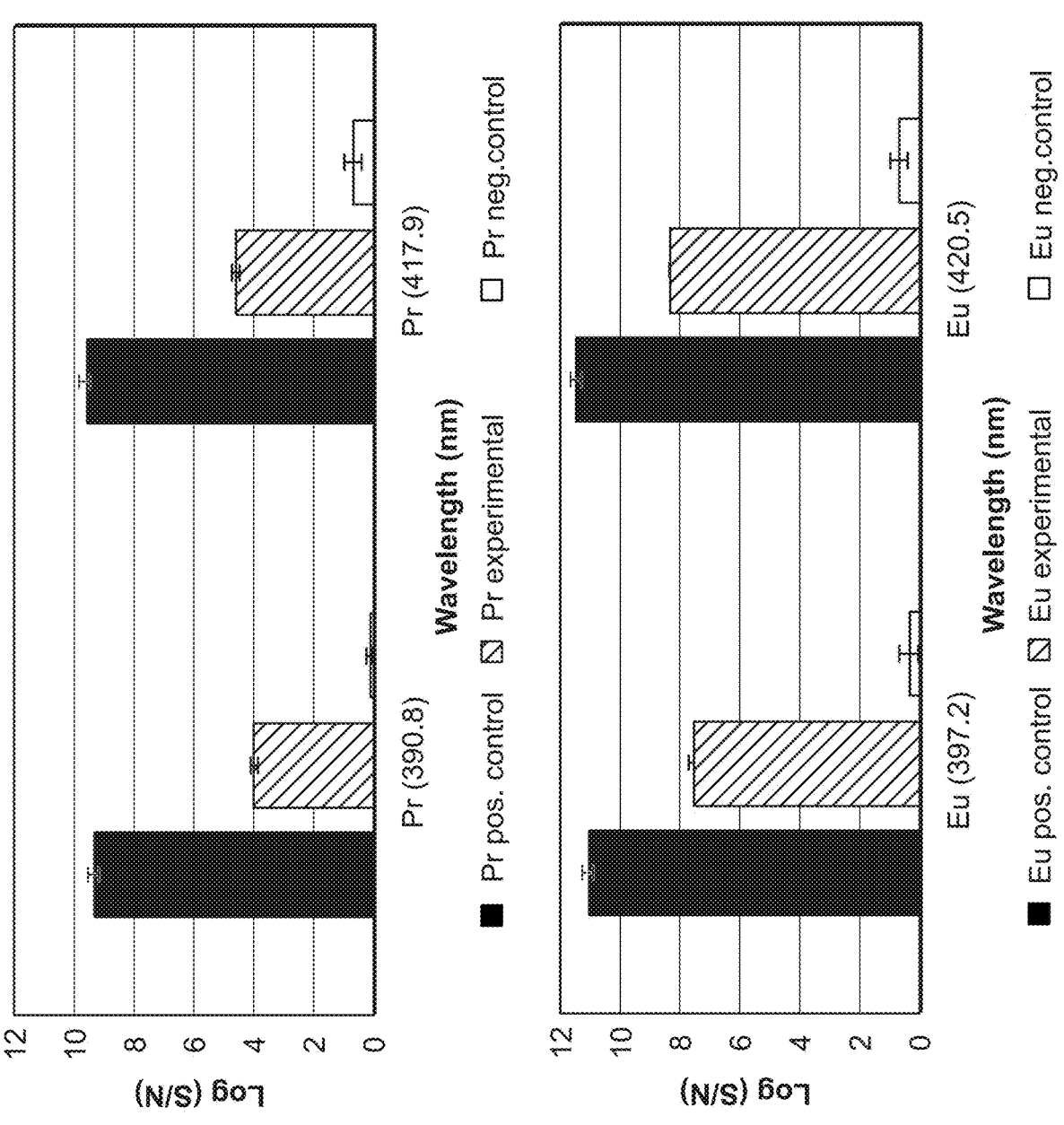

In addition to LIBS, LA-ICP-OES was used to measure gold emission on nitrocellulose paper. Similarly to LIBS results, The pink line on the dry GNP paper-based assay generated a stronger gold LA-ICP-OES signal than the area adjacent to the pink line (FIG. 21).

LIBS and LA-ICP-OES Analysis of Lanthanides in Nitrocellulose Paper

Lanthanide emission lines were first located along the spectrum using the ICP standard positive controls, and then measured for untreated paper, and paper treated with lanthanide-conjugated antibodies.

Ablation of ICP standards on nitrocellulose yielded a complex emission spectrum. Prominent emission lines were identified as belonging to lanthanides using the NIST database (Eu: 452.3, 459.4, 462.7 and 466.2 nm; Dy: 404.6, 407.8 and 409.4 nm; Pr: 511.0, 512.9, 532.3; Yb: 369.4 and 398.8 nm; Nd: 513.1, 525.0, 532.0 and 535.7 nm). For all samples except dysprosium line 404.6 nm, ICP standard positive controls generated stronger emission signals for the elements of interest than the experimental treatments (FIGS. 22A-E). Though the same quantity of each type of lanthanide ICP standard was added to nitrocellulose paper, some lanthanide ICP standards produced signals with higher S/N than others. The europium ICP standard produced the most distinct signal, followed by Yb, Pr, Nd and Dy. Metal-conjugated antibodies showed a slightly different trend, with Eu producing the most distinct signal, followed by Dy, Yb, Nd and Pr. Negative controls produced little or no signal at the wavelength locations of interest compared to the positive controls and experimental samples. S/N values for each element and treatment are provided in Table 2.

25

TABLE 2

Signal to noise ratio was measured for lanthanide emissions among
three types of samples: ICP standards on paper, lanthanide-conjugated
antibodies on paper, and untreated paper. Each value represents S/N
calculated from the aggregate of 15 ablations. Both the ICP
standards and lanthanide-conjugated antibodies had higher S/N
compared to untreated paper

| Wavelength (nm) | ICP Standard (S/N) | Negative Control (S/N) | Conjugated Antibody (S/N) |
|---|---|---|---|
| Europium | | | |
| 452.3 | 2211 | 10 | 167 |
| 459.4 | 2383 | 0 | 1106 |
| 462.7 | 2376 | 5 | 1030 |
| 466.2 | 1678 | 0 | 649 |
| Ytterbium | | | |
| 369.4 | 444 | 0 | 80 |
| 398.8 | 740 | 0 | 197 |
| Dysprosium | | | |
| 404.6 | 395 | 4 | 522 |
| 407.8 | 532 | 11 | 261 |
| 409.4 | 433 | 9 | 158 |
| Neodymium | | | |
| 513.1 | 203 | 8 | 34 |
| 525.0 | 179 | 2 | 22 |
| 532.0 | 175 | 2 | 27 |
| 535.7 | 120 | 9 | 23 |
| Praseodymium | | | |
| 511.0 | 338 | 0 | 31 |
| 521.9 | 248 | 0 | 18 |
| 532.3 | 245 | 0 | 18 |

Analysis with LA-ICP-OES yielded results for Nd, Eu, Dy and Pr detection that overall reflected the trends observed with LIBS. For all lanthanides, the ICP standard positive control produced the most intense signal, followed by lanthanide-conjugated antibodies, and then untreated nitrocellulose (FIGS. 23A-D)

Repeated Sampling of Nitrocellulose Paper

To determine the number of laser pulses that would be sufficient to generate a gold signal from GNP PBBs, 3 areas of a dry test strip's pink line were sampled 10 times. A single 18 mJ laser pulse focused to a spot of 100 µm was sufficient to form a visible crater on nitrocellulose and generate a gold emission signal without ablating through all the material. By observing the process of ablation with a camera, it was noted that the nitrocellulose is easily ablated.

Nitrocellulose paper is a highly flammable porous material composed of carbon, nitrogen, hydrogen and oxygen. Nitrocellulose paper used for bio-assays is delicate, where the pores easily collapse if pressure is applied to the structure. In many GNP PBBs dry gold nanoparticles are embedded in the porous nitrocellulose matrix upon completion of the bioassay. When gold nanoparticles are sufficiently concentrated, a distinct pink color can be visually detected. Both the nitrocellulose and nanoparticles are loosely bound materials, making them easy to ablate. Crater deepening upon repeated ablation may be the cause for signal degradation observed in FIG. 18. Crater walls and debris deposited at the edge of the crater can obstruct plasma emission from reaching the detector.

LIBS and LA-ICP-OES Analysis of Gold-Nanoparticles in Nitrocellulose Paper

When ablating the pink line on the nitrocellulose paper, gold line emission signals were detected. Gold emission signals were not detected when ablating the white section of nitrocellulose adjacent to the pink line. In this study, visual detection of gold nanoparticles on paper was supported by LIBS detection of gold nanoparticles. Interestingly, gold emission intensities were comparable between wet and dry nitrocellulose paper. This may imply that water does not have a significant impact on the plasma generation process in nitrocellulose paper, or the laser pulse rapidly evaporates the water before ablating the sample. Bioassay analysis tools capable of analyzing wet substrates is advantageous since most biological samples/bioassays contain water. The results show that LIBS is capable of detecting metal-conjugated antibodies in aqueous environments typical of biological systems, an important finding for future bioassay development.

LIBS and LA-ICP-OES Analysis of Lanthanides in Nitrocellulose Paper

Our results show that lanthanide-bearing polymers on nitrocellulose are detectable using LIBS. The positive and negative controls (ICP standards on nitrocellulose and untreated nitrocellulose) were initially used to localize prominent lanthanide emission peaks and determine the background spectrum produced by nitrocellulose. This information was then used to determine the presence of lanthanide-conjugated antibodies on nitrocellulose.

Figure 24:
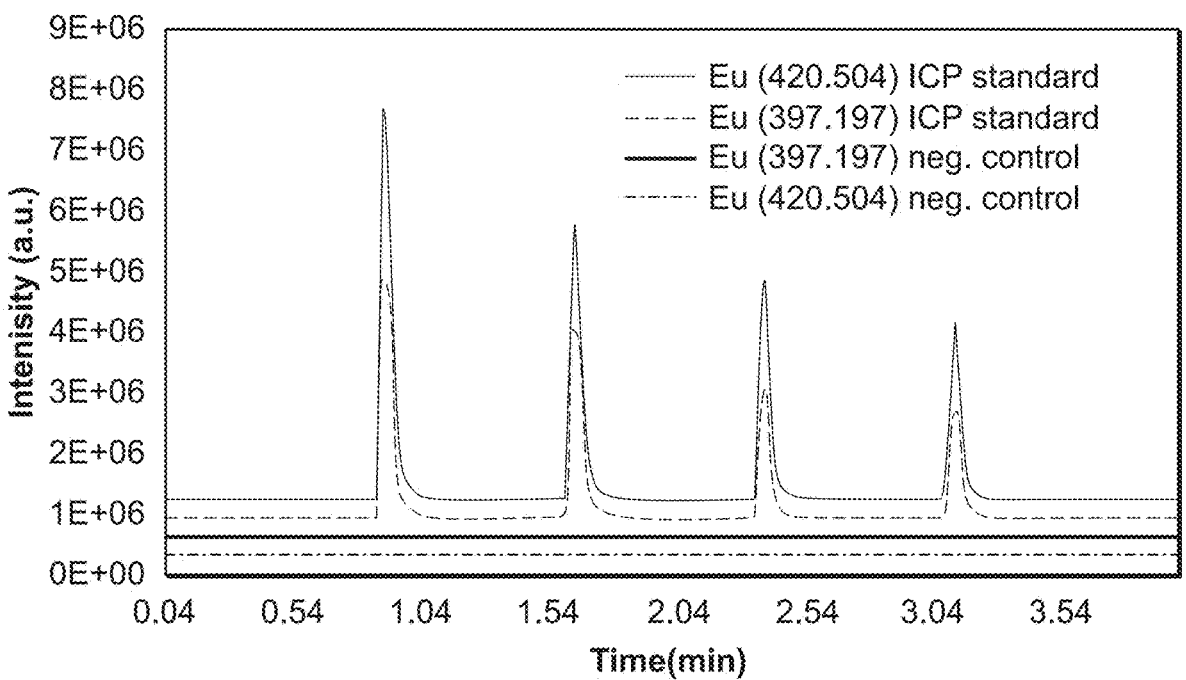
FIG. 24 shows that LA-ICP-OES was performed on Eu ICP standards on paper in an He carrier gas environments. The Eu signal in the positive control was observed to spike following each ablation series. Signal was also observed to degrade as the paper was sampled from the edge towards the center.

As observed in FIG. 24, the signal intensity of Eu decreases as different sections of the nitrocellulose paper were sampled. The first peak is associated with ablation along the edge of the paper, whereas subsequent peaks are associated with ablations increasingly close to the center of the paper. This pattern may be attributed to diffusion properties of liquids containing particulates and suggests that Eu distributed unevenly when dried onto the paper. The concept is supported by observing water with red dye also distributing unevenly on nitrocellulose paper—the dye concentrates to the edges of the paper. Since our data suggested that Eu was unevenly distributed across the surface of the paper, it can be assumed that all samples also have uneven distribution of material since they were treated similarly. To establish limits of detection of metals on nitrocellulose paper, a method needs to be established to evenly dry liquid solutions on paper. It is expected that the limit of detection will partially depend on the element.

Unlike gold nanoparticles, many other metal particles are not visually easy to detect on paper. Lanthanide luminescence is detectable on paper, however the panel of labels is limited and emission profiles often overlap. A large panel of metal bio-tags exist for visual (Au, Ag, Fe), luminescence (lanthanides), fluorescence (elements used for quantum dots such as Zn, Pb and Cd) and mass detection (lanthanides, and elements such as Pt, In). This study shows the use of LIBS to use laser-induced breakdown spectroscopy and paper-based bioassays to detect metals that are not easily visually detectable.

Laser-Ablation Inductively Coupled Optical Emission Spectroscopy as a Supporting Analytical Tool LA-ICP-OES was used as a secondary method of analyzing PBBs and nitrocellulose samples treated with lanthanides. Though this method is not directly comparable with LIBS, the results of the two analytical methods support the same conclusion. LA-ICP-OES can be considered as an acceptable supporting tool for LIBS analysis of PBBs, especially if the same emission lines are compared between both instruments.

Conclusion

Low-cost, rapid, and portable bioassays and analytical tools are of great interest, especially in applications concerning public and military health and safety. While many options exist that fit these specifications, they are often not sensitive enough or capable of detecting multiple analytes using a single test. To address the need for a bioassay and analytical tool that are cost effective, rapid, field deployable, sensitive and multiplexed, we explored the combination of three proven technologies: laser-induced breakdown spectroscopy, paper-based bioassays, and metal-conjugated antibodies. This study establishes the novel combination of these technologies for detecting analytes, such as biological analytes (bioassay capability). LIBS was effective in detecting metal-conjugated antibodies on nitrocellulose paper. The results were supported using LA-ICP-OES.

Example 3: How Pulse Number and Repetition Rate Affects Crater Size

Figure 25A:
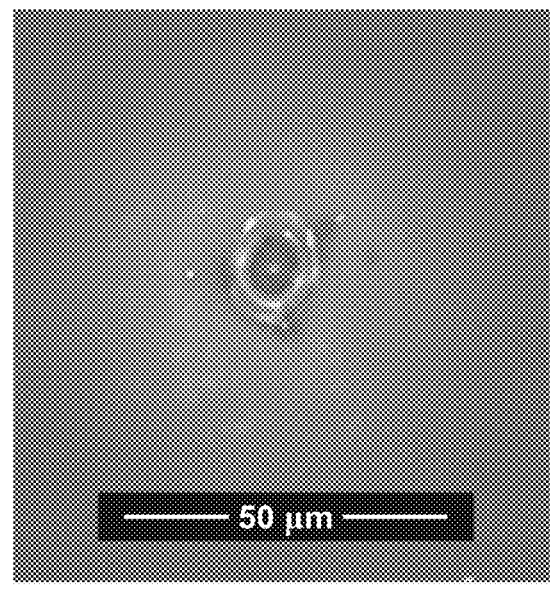
FIGS. 25A-E show how pulse number and repetition rate affects crater size.
Figure 25B:
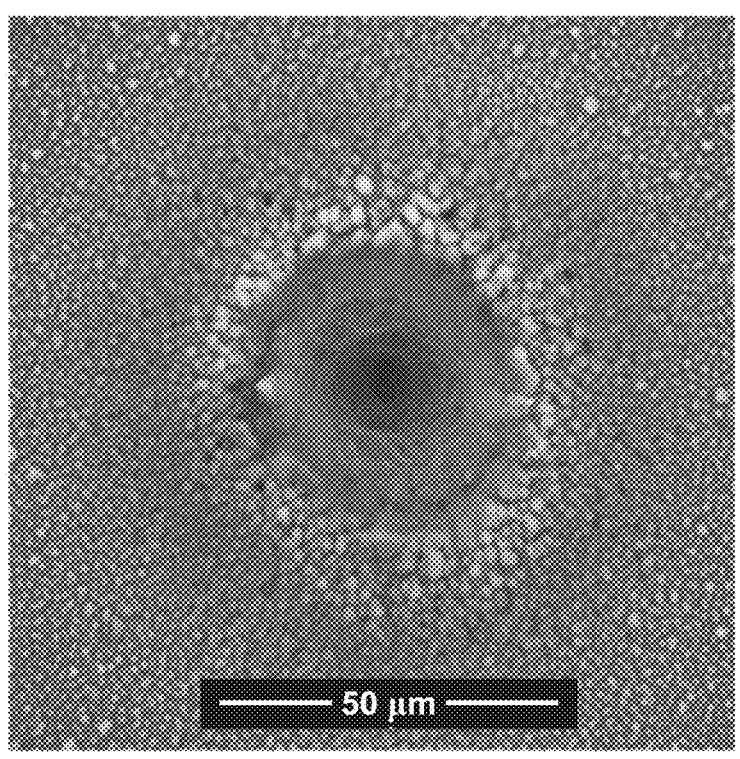
Figure 25C:
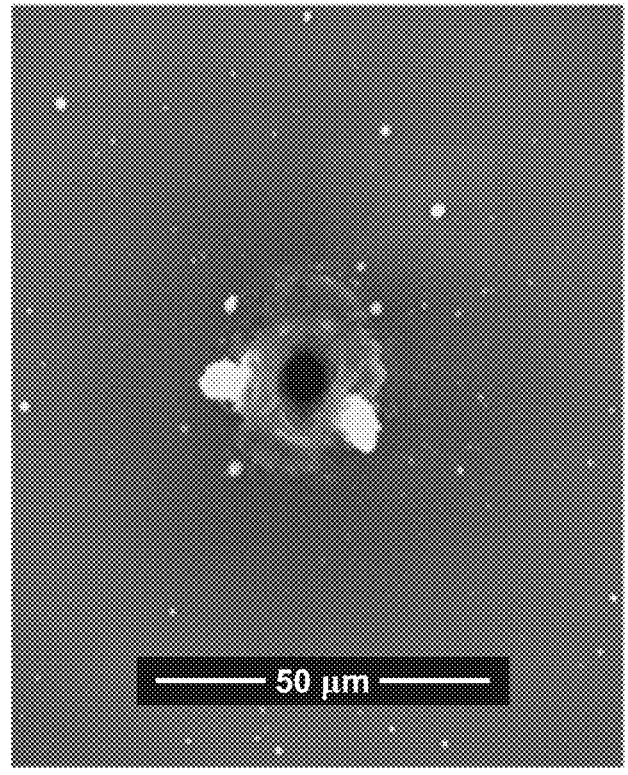
Figure 25D:
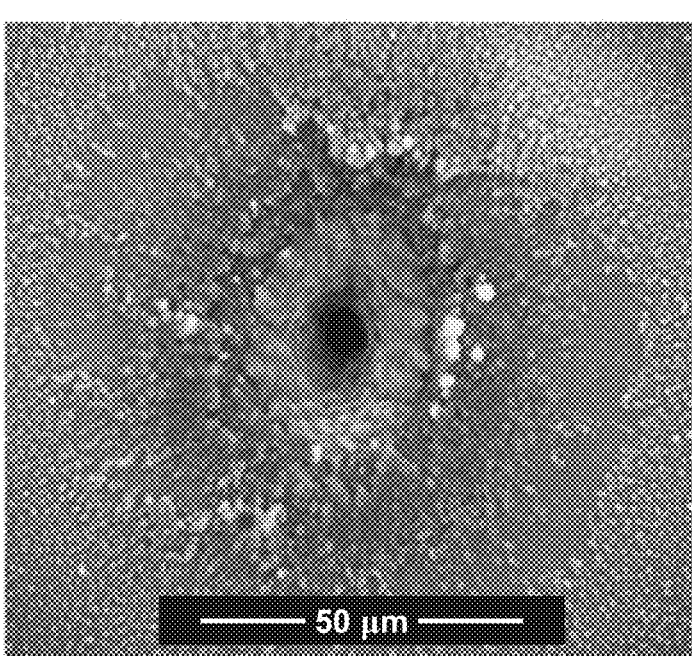
Figure 25E:
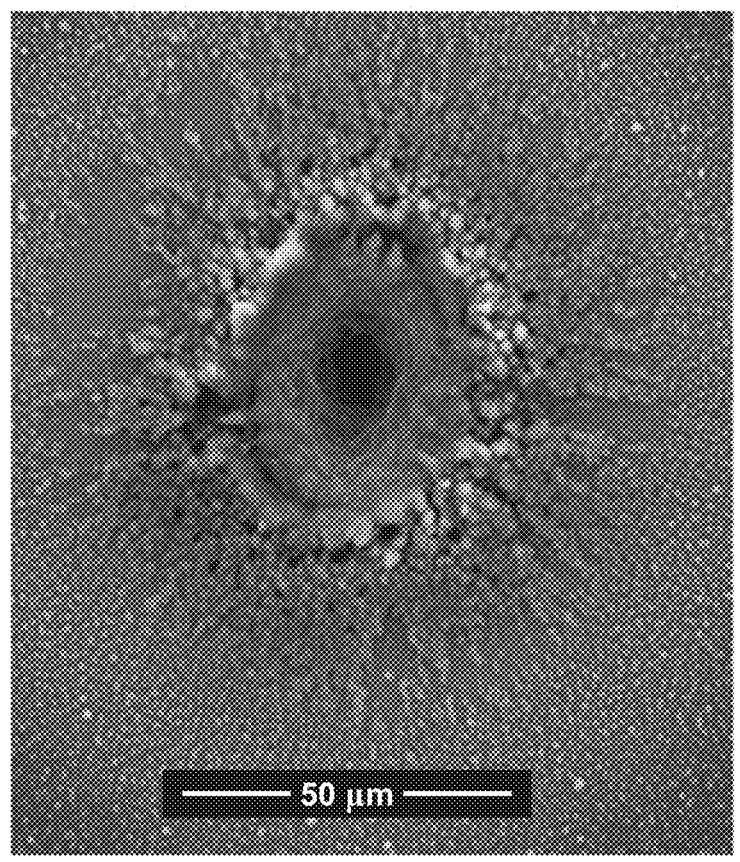

FIGS. 25A-E show how pulse number and repetition rate affects crater size. FIGS. 25A-B show 500 Hz varied pulse number: 10 pulses, 500 Hz (FIG. 25A) and 1000 pulses, 500 Hz (FIG. 25B). FIGS. 25C-E show 1000 Hz, varied pulse number: 200 pulses, 1000 Hz (FIG. 25C); 500 pulses, 1000 Hz (FIG. 25D); and 1000 pulses, 1000 Hz (FIG. 25E). Craters made with 1000 Hz pulses seem oval—this may be because the beam is not circular.

Figure 26A:
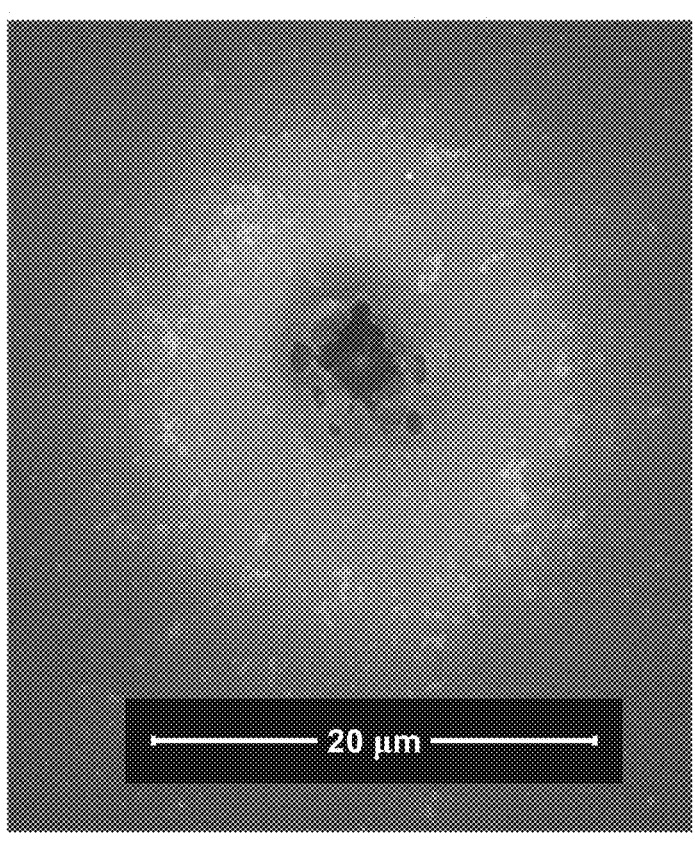
FIGS. 26A-G show images of low pulse number and varied repetition rate.
Figure 26B:
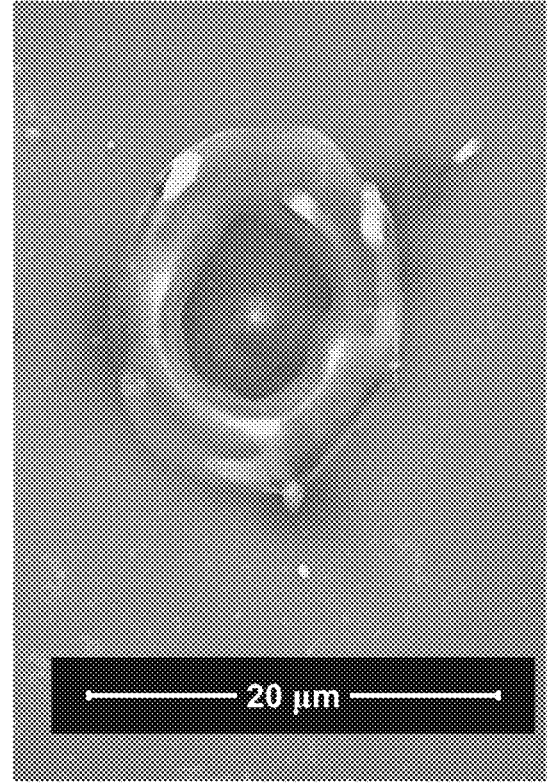
Figure 26C:
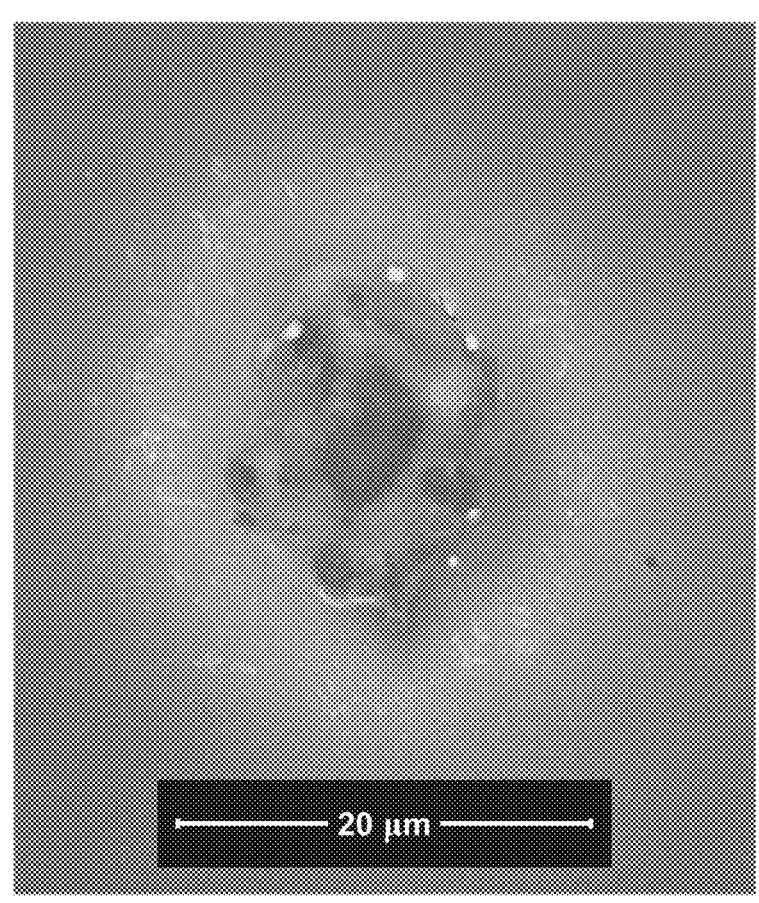
Figure 26D:
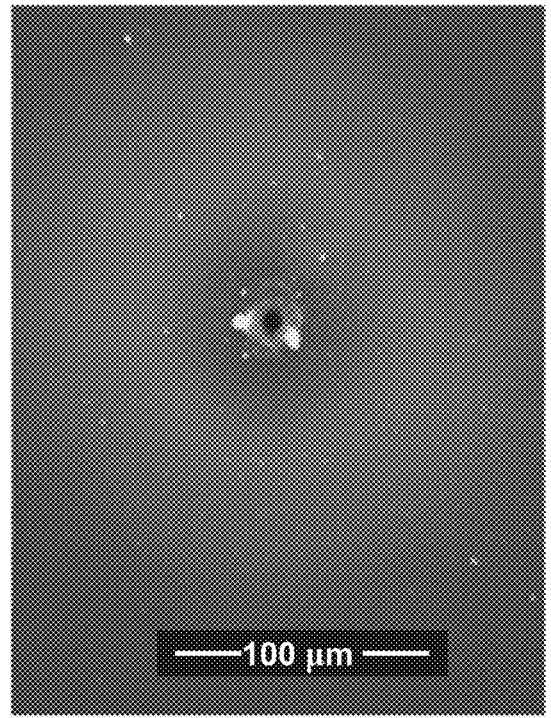
Figure 26E:
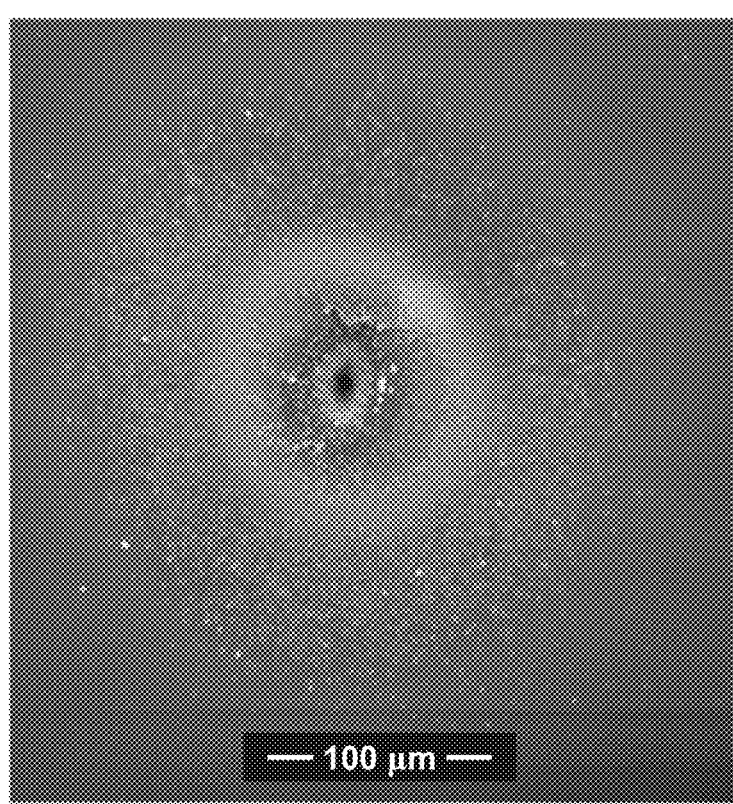
Figure 26F:
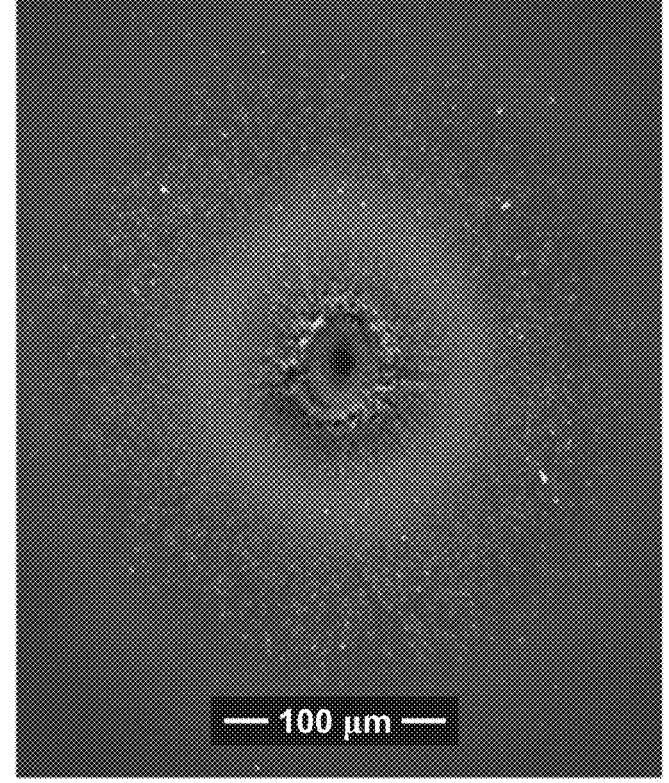
Figure 26G:
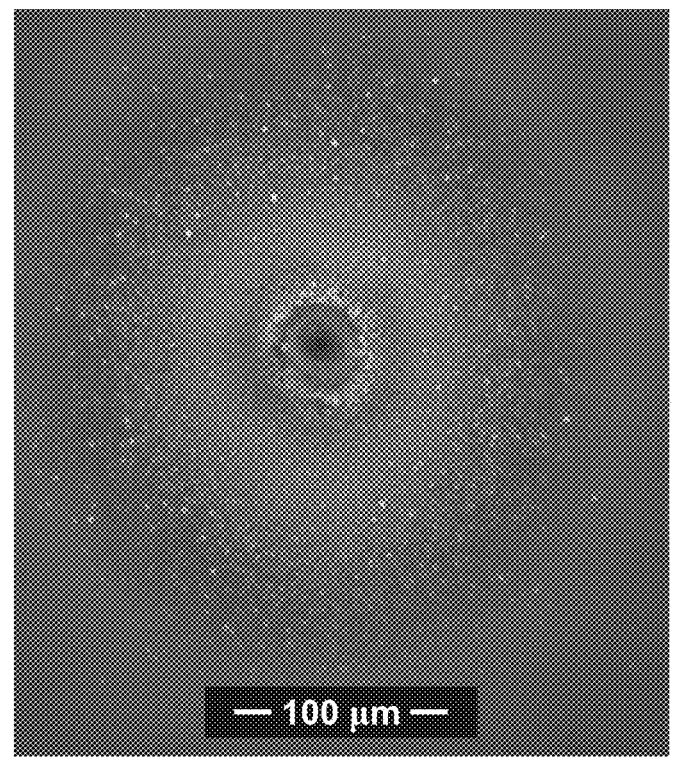

FIGS. 26A-G show images of low pulse number and varied repetition rate. FIGS. 26A-C show Varied repetition rate, 10 pulses: 10 pulses, 8 Hz (FIG. 26A); 10 pulses, 500 Hz (FIG. 26B); and 10 pulses, 1000 Hz (FIG. 26C). FIGS. 26D-G show: 200 pulses, 1000 Hz (FIG. 26D), 200 pulses, 1000 Hz (FIG. 26E), 1000 pulses, 1000 Hz (FIG. 26F), and 1000 pulses, 500 Hz (FIG. 26G). All craters shown were formed with 1000 Hz pulses (with the exception FIG. 26G). It seems like in the first 200 pulses, small particulate debris deposits around the crater. At 500 pulses, the size of the particulate debris is much larger, and a wall starts to form at the edge of the crater. At 1000 pulses, a wall of debris has formed at the edge of the crater. At 500 Hz, the debris seems to deposit more evenly around the crater.

Figure 27A:
FIGS. 27A-B show comparison of craters formed by different lasers.
Figure 27B:
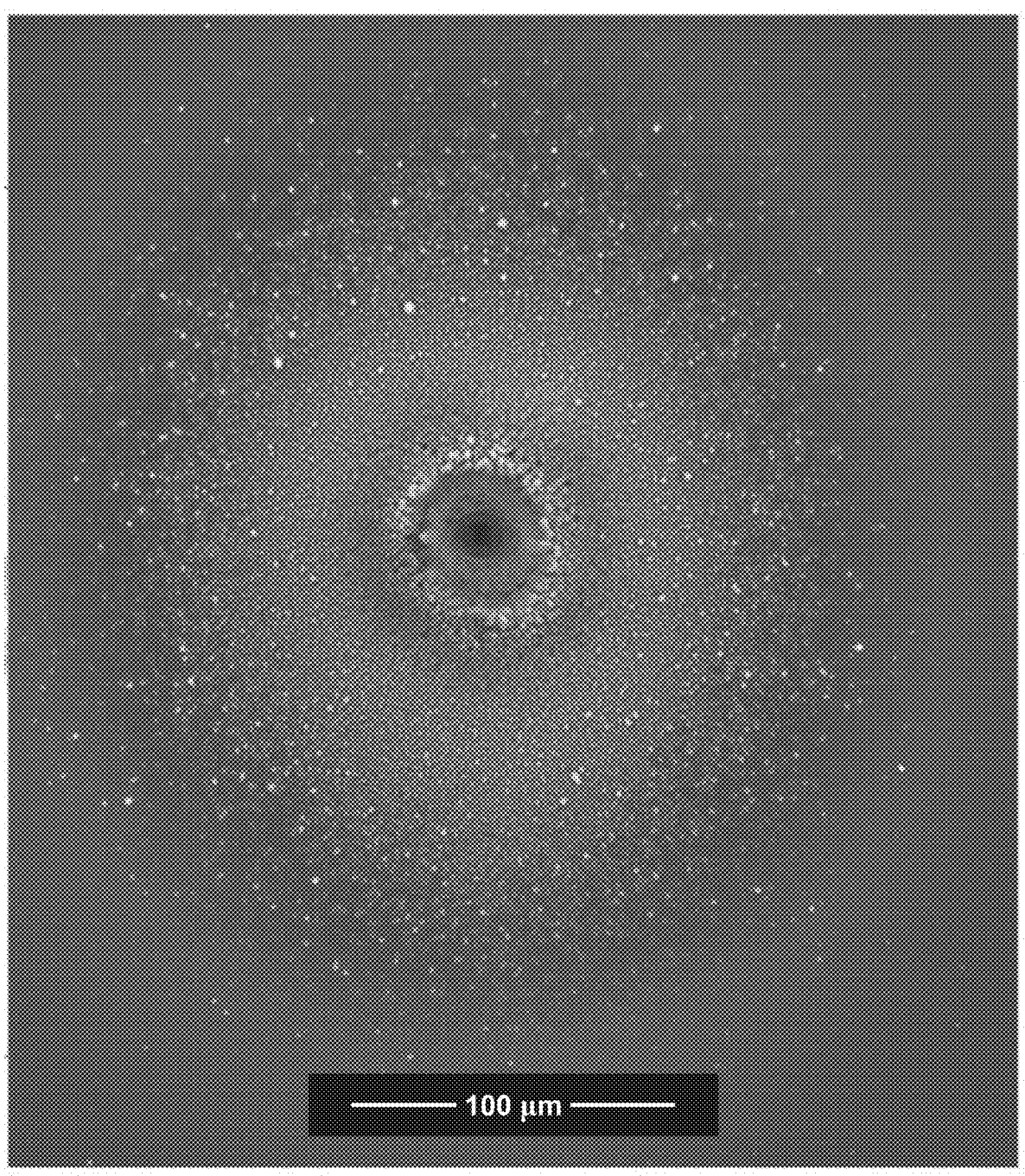

FIGS. 27A-B show comparison of different lasers. FIG. 27A shows crater formed by XLP-1064-1 Laser (used to acquire data on gold nanoparticles on the surface of a silicon wafer). FIG. 27B shows crater formed by COBOLT TOR XS laser (high performance Q-switched lasers).

The data in this example show that pulse rates and pulse number at 500-1000 Hz and 200-1000 pulses generated deep craters. While deep craters might (to some degree) be beneficial for characterizing solid samples like silicon wafers, it may not be beneficial for characterizing particulate material deposited onto the surface of the wafer. Pulse rate and pulse number such as 8 Hz 10 pulses may be more appropriate for surface sampling. The COBOLT TOR XS (high performance Q-switched lasers) yields a much more uniform crater than the laser previously used for LIBS experiments by our lab (LaserX).

Example 4: Single Layer Assay

FIG. 6 provides an exemplary embodiment of a single layer bioassay. This example illustrates a paper-based bioassay to concentrate the analyte, and label the analyte with metal bio-tags. Antibodies targeting multiple analytes are functionalized to a region of nitrocellulose paper. When the sample is added, the analyte will bind to the paper. Antibodies complexed to metals (a unique metal per antibody target) and conjugated to gold nanoparticles are then used to label the analyte on the paper (shown as the pink spot in the cartridge).

Analysis of the bioassay is performed using LIBS—a technique to characterize the elemental composition of a material. Detection of a metal-complexed antibody indicates the presence of the associated analyte in the sample. The unique and narrow signal produced by every antibody permits LIBS to detect each analyte in a single sampling event. Laser-ablation inductively coupled optical emission spectroscopy (LA-ICP-OES) may be used as a supporting analytical method.

FIG. 35 is another example for a single layer assay showing a reagent including metal-bearing polymers complexed to antibodies, which were conjugated to the surface of nanoparticles (visually observable by the naked eye). The data show that the reagents bound the substrate and produced spots visually detectable by the naked eye.

Example 5: Multi-Layer Assay

Portable sensors for chemical/biochemical analysis often consist of a chemical/biochemical capture device that immobilizes analytes onto a substrate, and a detection tool. Occasionally, these capture devices also use tags to label the chemical/biochemical analyte. Modern portable sensors typically detect a few analytes simultaneously. This is often due to limitations in the physical size of the detection instrumentation.

The invention recognizes that sensors for applications such as bio-terrorism defense, food contamination detection and forensics need to be portable, sensitive and highly multiplexed Many sensors have one or two of these qualities, but not all three. Through the use of the capture device being proposed in this invention, the sensors of the invention are capable of all three.

Figure 37A:
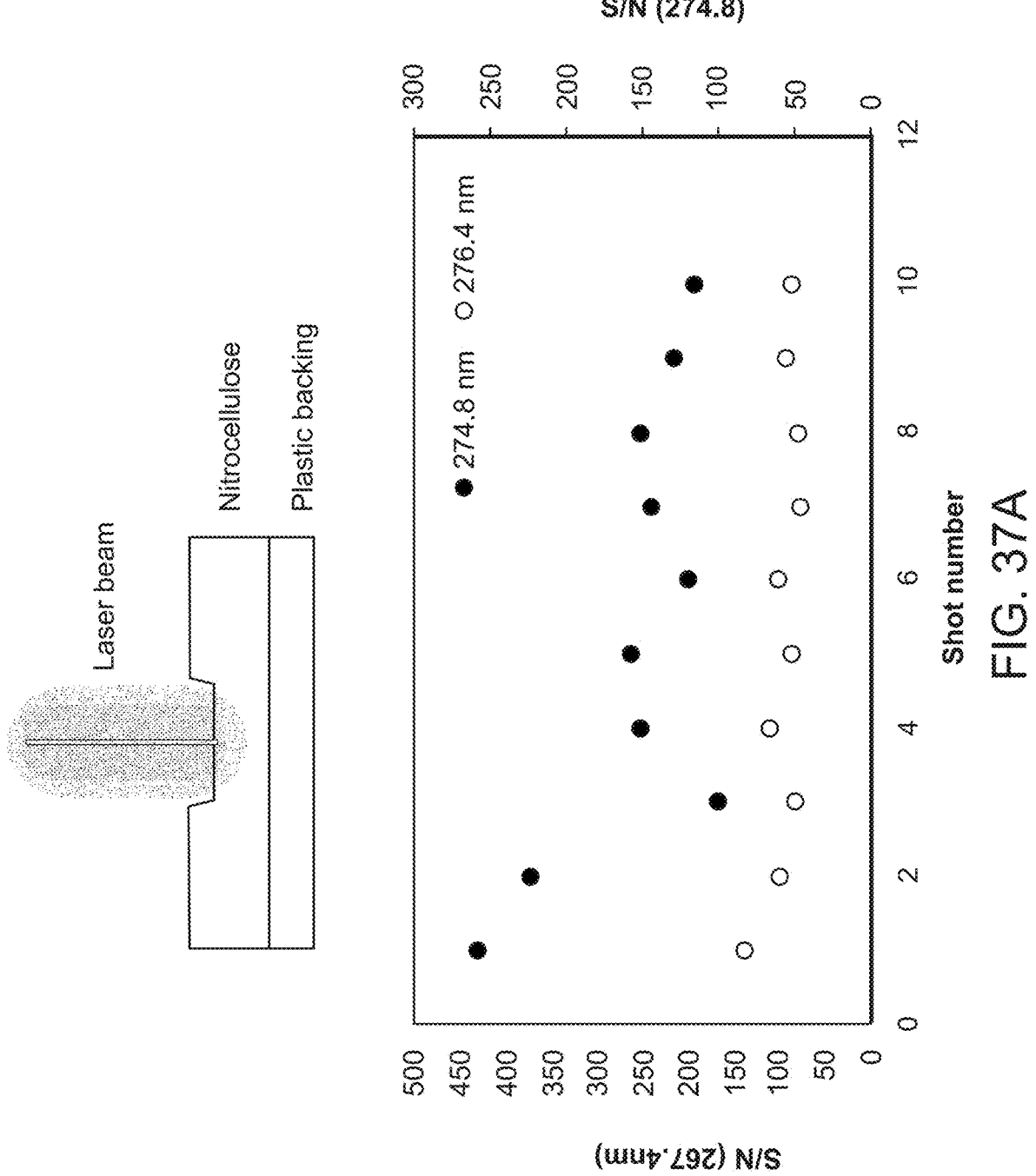
FIG. 37A shows LIBS signal produced by gold nanoparticles on nitrocellulose degrades over repetitive LIBS pulses (shots).
Figure 37B:
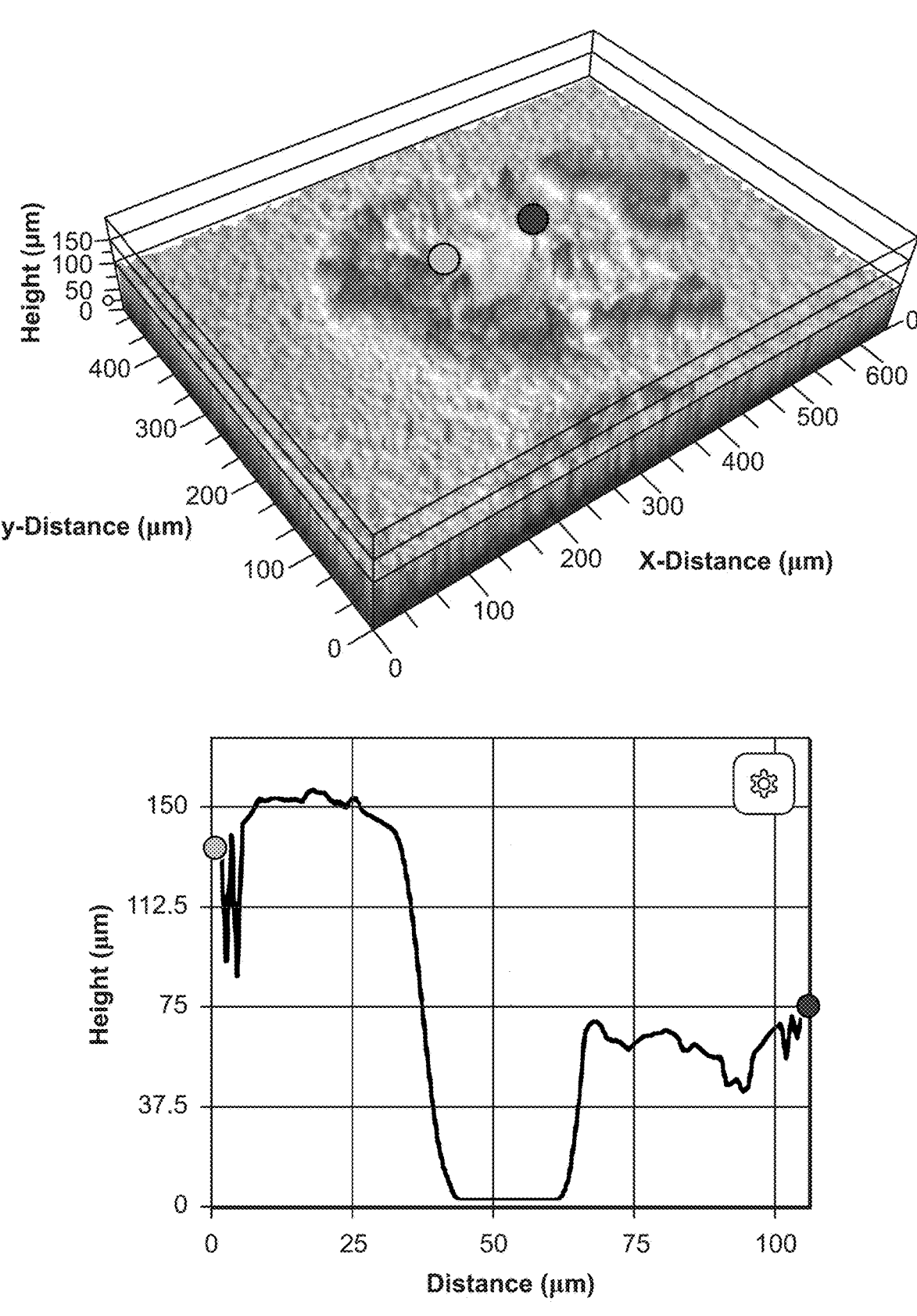
FIG. 37B shows an image (left side) and depth profile (right side) a crater formed by a single LIBS pulsed on nitrocellulose paper.

This example provides a unique method of sampling substrates using laser-induced breakdown spectroscopy. The methods described herein utilize multiple membrane layers to capture analytes (e.g., each layer is associated with the capture of specific analytes). In some versions of this invention, the captured analytes can also be labeled with detection molecules and tags. The methods then utilize LIBS/SIBS to sample stacks of membranes by "digging" through the membrane using LIBS/SIBS. By use of LIBS/SIBS, a laser can successively pulse through each membrane layer, exposing the analyte, detection molecule, and tag. FIGS. 37A-B illustrate that ability of LIBS. FIG. 37A shows LIBS signal produced by gold nanoparticles on nitrocellulose degrades over repetitive LIBS pulses (shots). After ~3-5 shots, the laser ablates through the nitrocellulose layer, hitting the plastic backing. FIG. 37B, on the left side, shows an image of a crater formed by a single LIBS pulsed on nitrocellulose paper. FIG. 37B, on the right side show a depth profile of the crater.

There is no cross reactivity, since the target analyte/s are unique for each layer. It is not necessary to separate the signals since a standard signal processing can be performed on the combined signal to determine the presence of any particular analyte.

In certain embodiments, the methods described herein leverage at least the three following concepts: LIBS/SIBS as a technique to "drill" holes through multiple layers of material, and extract information from each layer; for layers (such as paper) that are used for molecular conjugation and labeling, this method enables a high degree of multiplexing such that a single layer allows detection of n analytes, and multiple layers allows detection of n analytes multiplied by the number of layers; and for layer-by-layer analysis, this approach does not require movement of the laser or sample (i.e., the same spot can be analyzed in each layer, providing different information in each layer, without the substrate be moved). Stated another way, the methods herein permit the option of sampling along the z axis (vertical axis), therefore avoiding the need to move the laser and/or the sample.

The processes described herein generally provide certain advantages for making LIBS measurements on liquids relative to previously known methods. In particular, the multi-membrane processes described herein permit a user to obtain separate analysis for portions of a sample that are size specific (tailored to the size of the constituents of the sample). Depending on the interest of the user, certain users may search for ions, magnetized particles, large or small bio-macromolecules, bacteria, etc.

Figure 28:
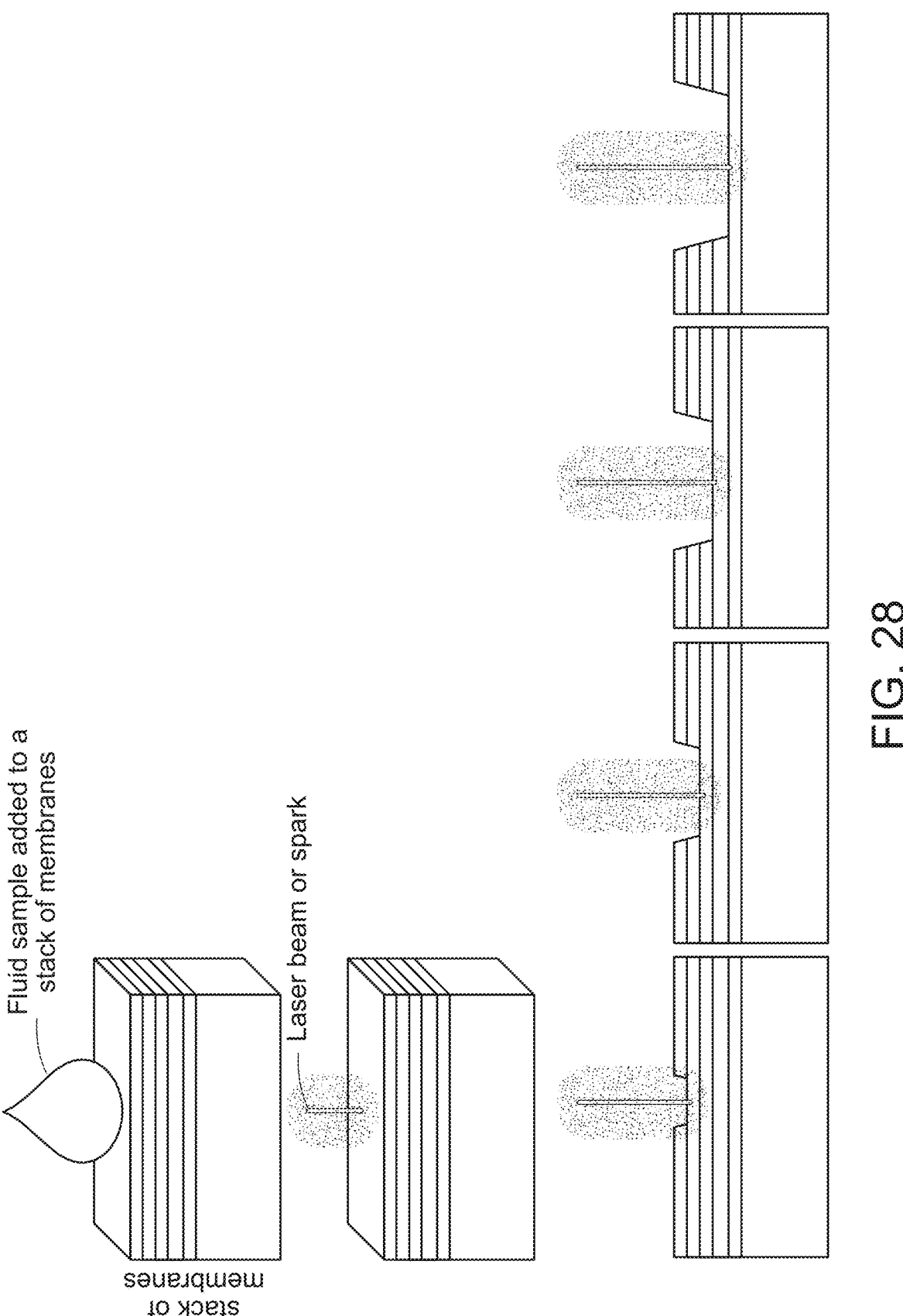
FIG. 28 is an illustration showing LIBS sampling of a multi-layer substrate.

FIG. 28 is an illustration showing LIBS sampling of a multi-layer substrate. Each layer in the diagram represents a substrate material (each layer may have the same or different characteristics). LIBS/SIBS forms craters during sampling. As the LIBS/SIBS forms craters, each layer is sampled. Depending on the thickness of the membranes, the sample or laser will not need to be moved for analysis of each layer.

Optionally, each layer of the membrane has unique properties that allows it to capture more than one analyte. In such embodiments, upon LIBS analysis, analytes on each layer can be distinguished based on their own chemical properties or based on the chemical properties of a unique tag that has been applied to each species of analyte.

Figures 29A, 29B:
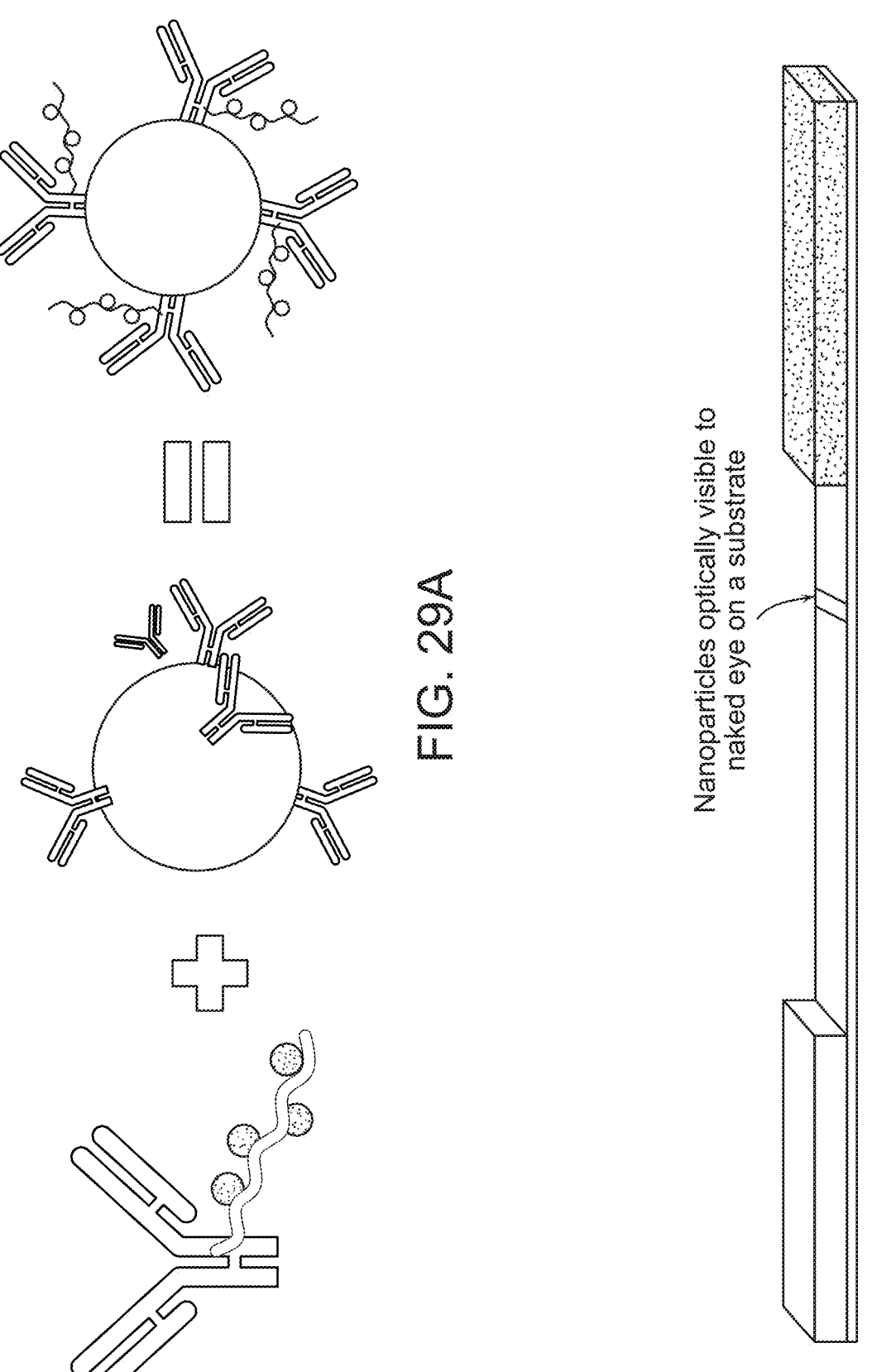
FIG. 29A shows an example of an antigen-identifying tag (detectable with LIBS).
FIG. 29B shows an example of a visual tag are gold nanoparticles that have a distinct pink appearance when they aggregate on a membrane (like paper).

The reagents for these methods combine two methods of conjugating bio-tags to metals. The first tag is a nanoparticle with distinct optical properties (e.g., can be seen visually by the naked eye on a substrate). The second tag is a metal ion complexed to a metal-chelating polymer. The nanoparticle tag permits visualization of the target immobilized to the membrane. The second tag permits the user to detect exactly which analytes are present in the sample. An example of an antigen-identifying tag (detectable with LIBS) is displayed in FIG. 29A. An example of a visual tag are gold nanoparticles that have a distinct pink appearance when they aggregate on a membrane (like paper), as shown in FIG. 29B.

Figure 30:
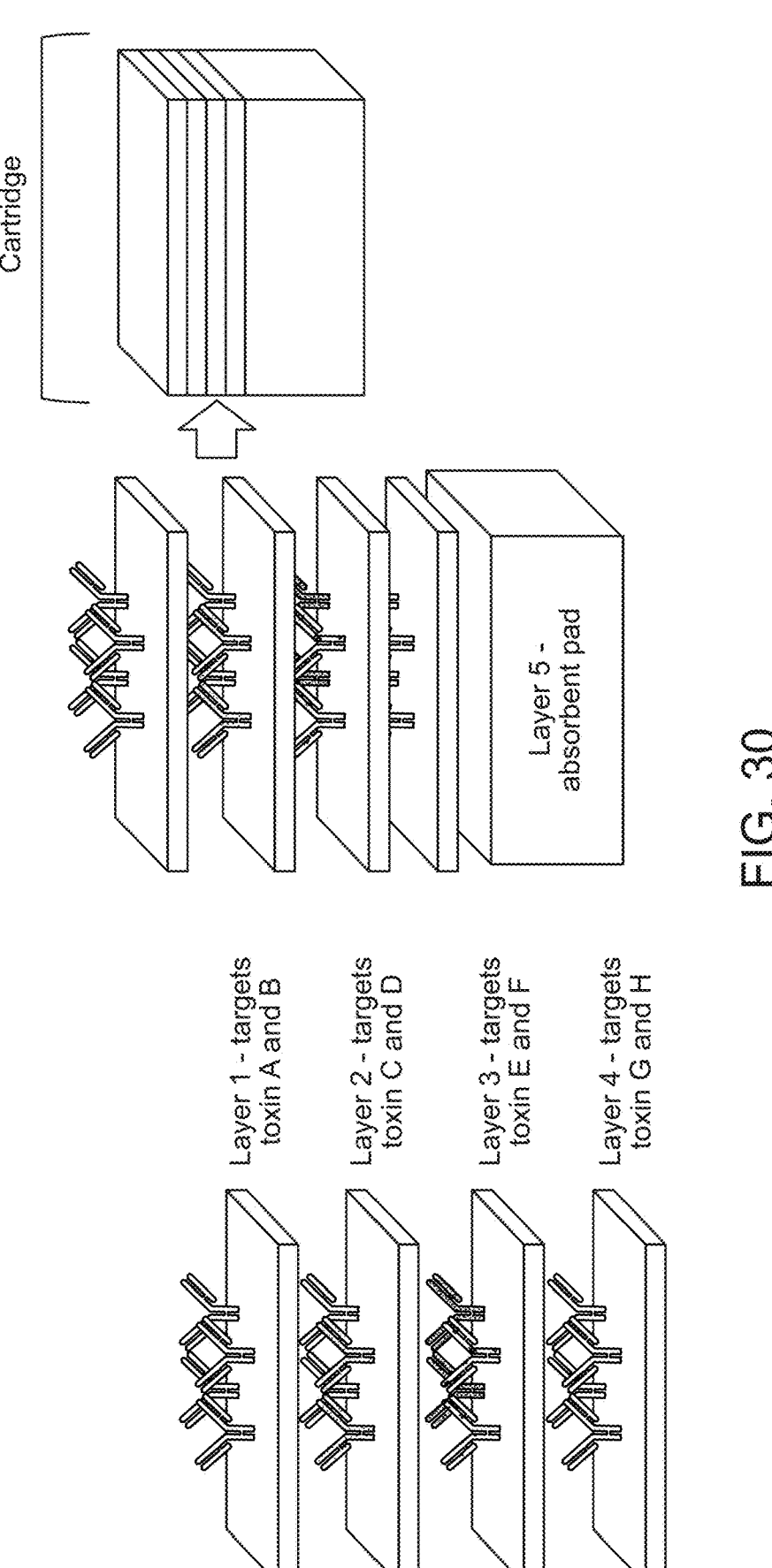
FIG. 30 shows an example of construction of a multi-layer bioassay cartridge.
Figure 31:
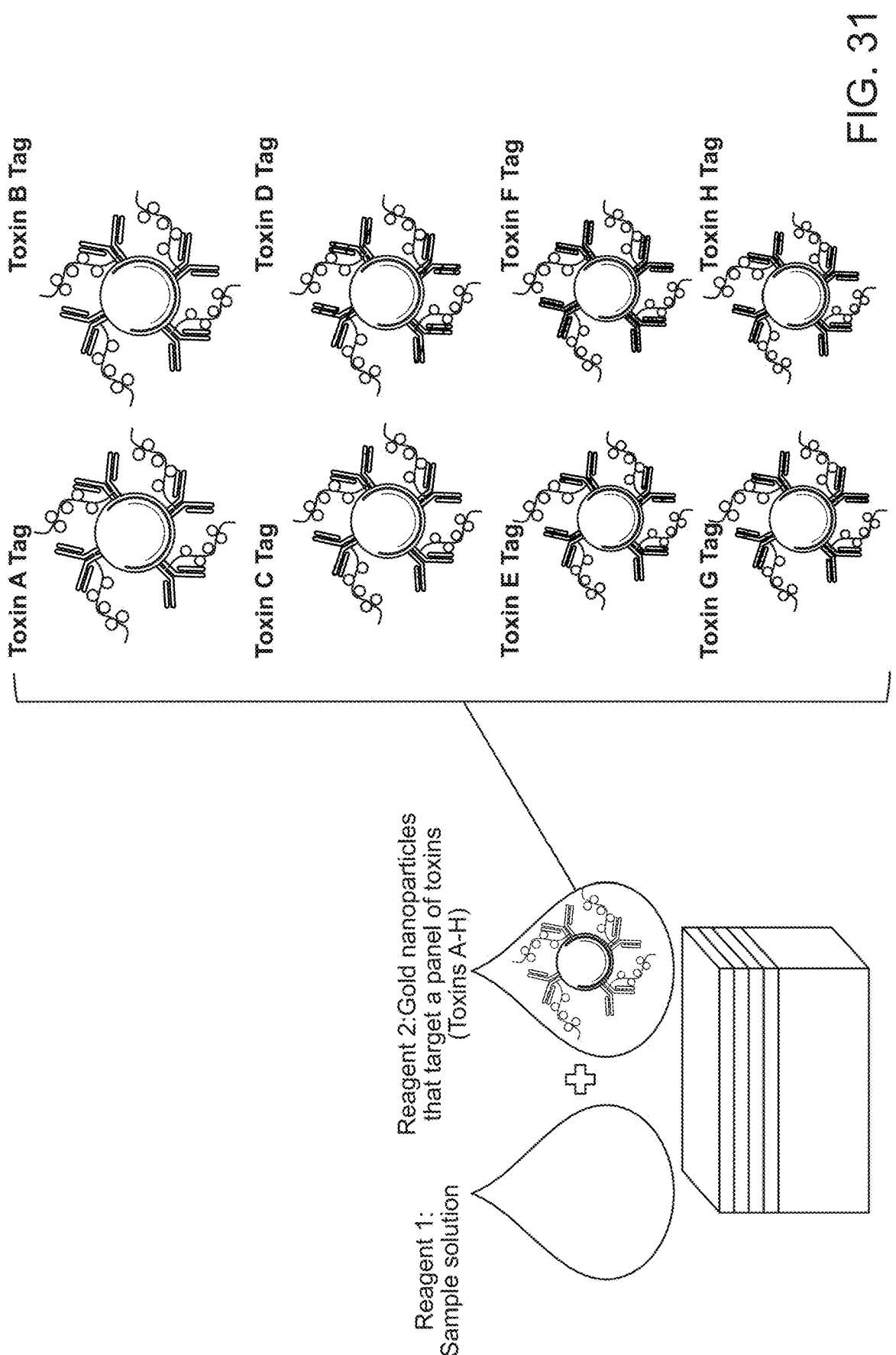
FIG. 31 shows exemplary different reagents for a multiplex assay and their application to a substrate such as described in FIG. 30.

FIG. 30 shows an example of construction of a multi-layer bioassay cartridge. Layers are prepared by applying anti-toxin antibodies to multiple sheets of nitrocellulose (each layer captures 2 types of toxins), and then stacking the nitrocellulose paper onto an absorbent pad. FIG. 31 shows exemplary different reagents for a multiplex assay and their application to a substrate such as described in FIG. 30.

Figure 32A:
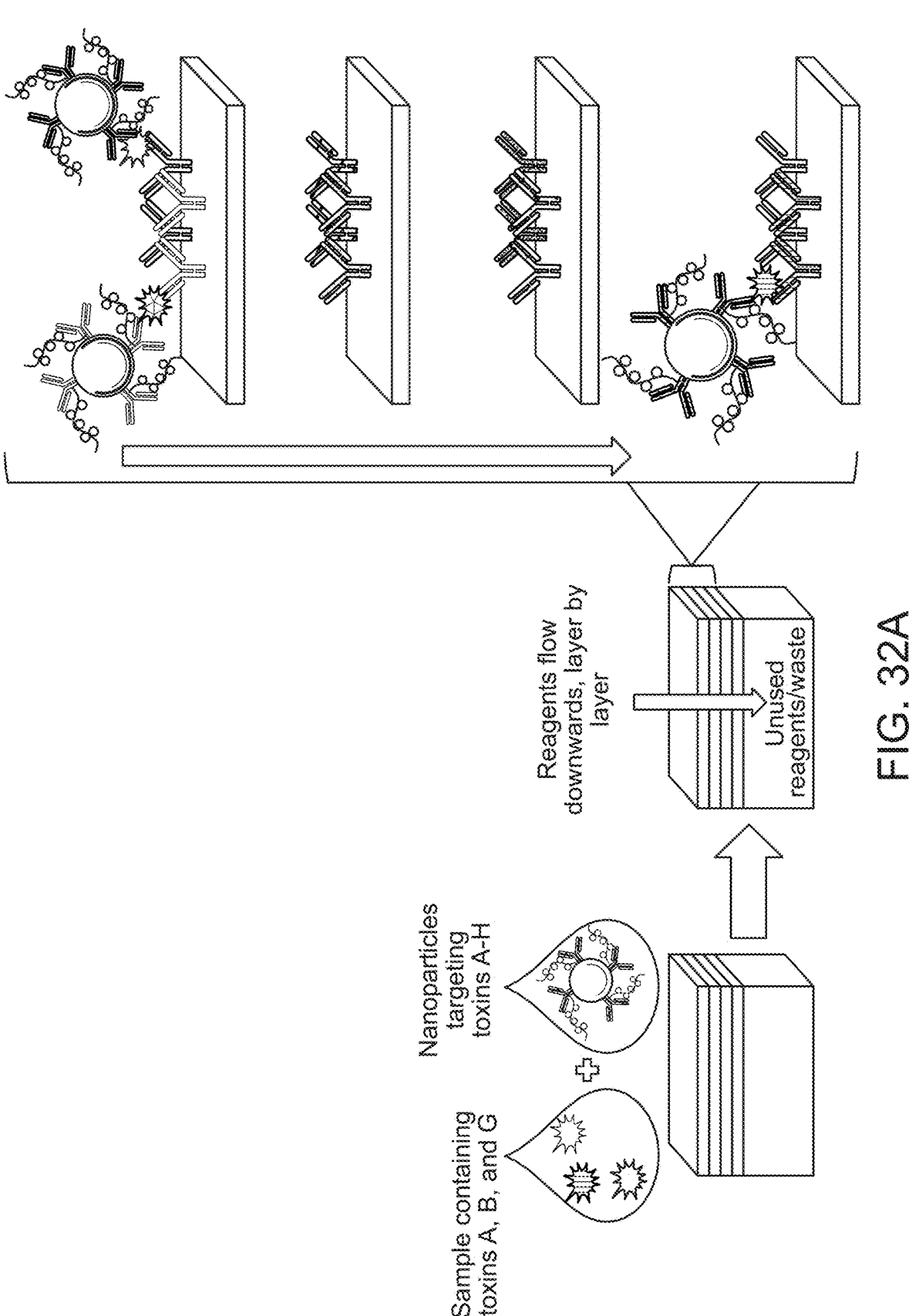
FIG. 32A illustrates use of a multi-layer bioassay to detect antigens (Reagents+Cartridge) in which the reagents include a nanoparticle core.

FIG. 32A illustrates use of a multi-layer bioassay to detect antigens (Reagents+Cartridge). A sample that is believed to be contaminated with toxins A-H is added to the paper bioassay (the sample actually contains toxins A, B and G). The antigens first bind to capture molecules in Layer 1. As the toxins and particles flow through the layers, they bind to specific layers. Note that flow is in a vertically direction (downward vertical flow) and this example describes vertical flow assays.

Figure 32B:
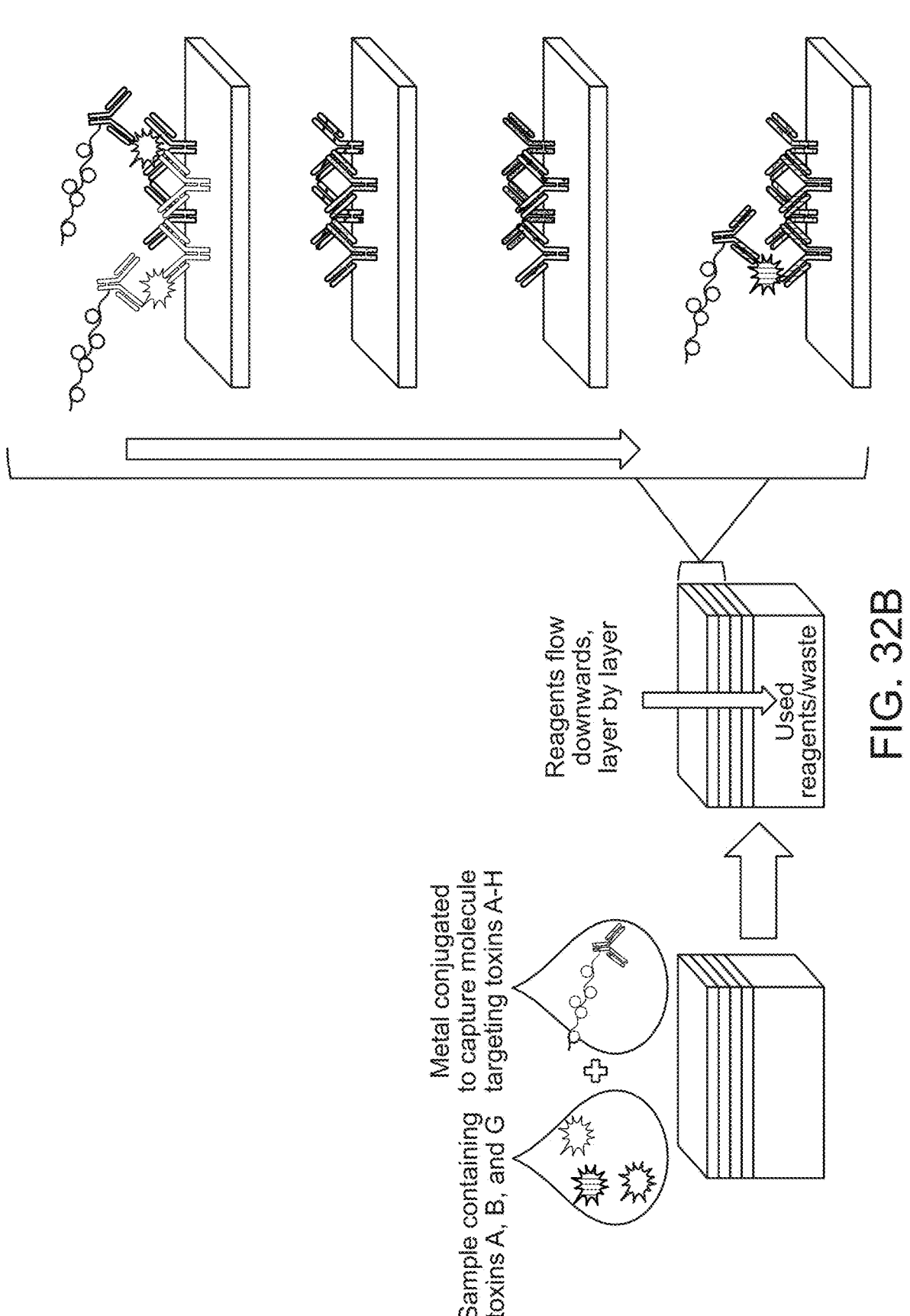
FIG. 32B illustrates use of a multi-layer bioassay to detect antigens (Reagents+Cartridge) in which the reagents do not include a nanoparticle core.
Figure 33:
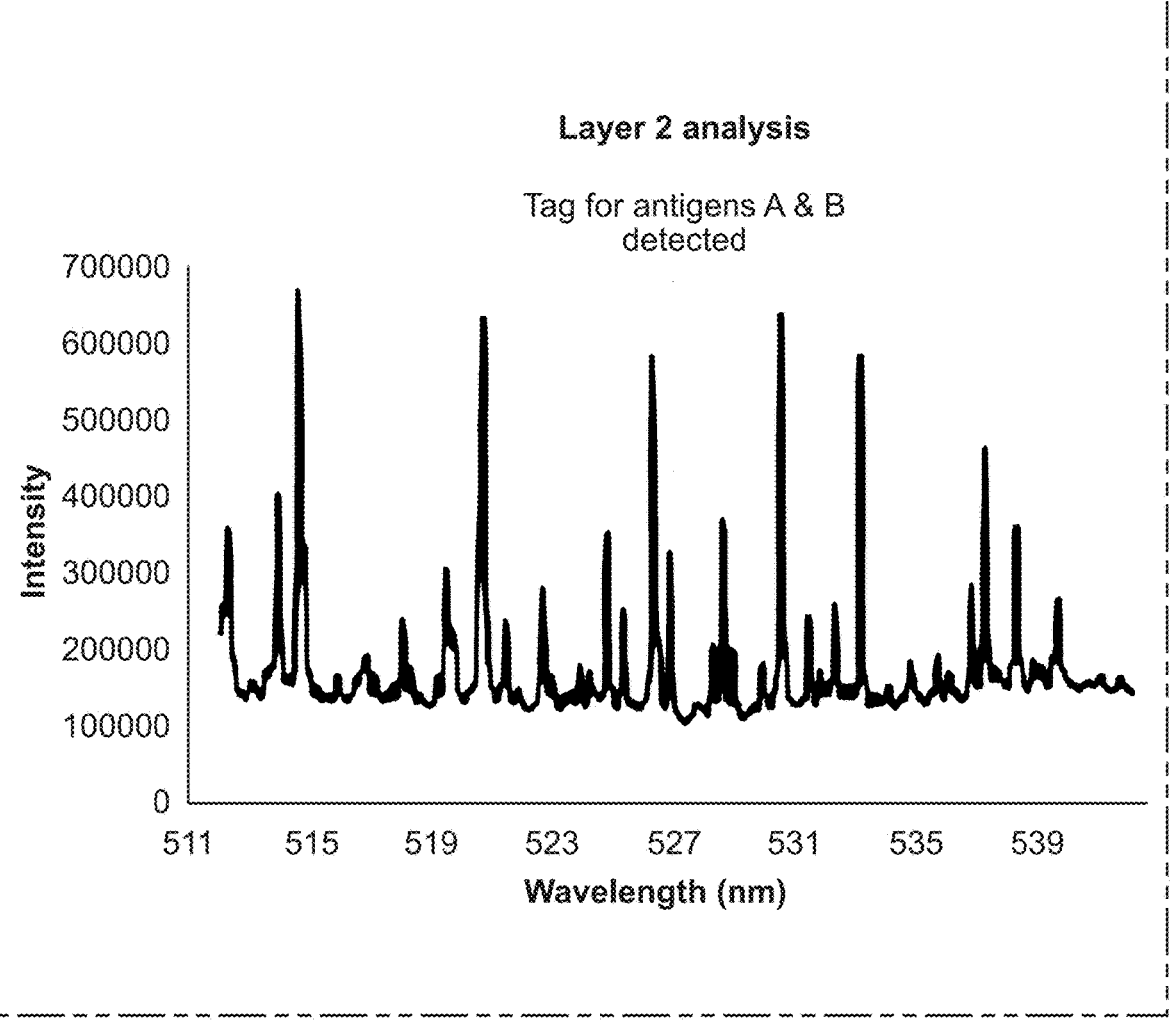
FIG. 33 shows assay detection results for the assay conducted in FIG. 32.
Figure 33:
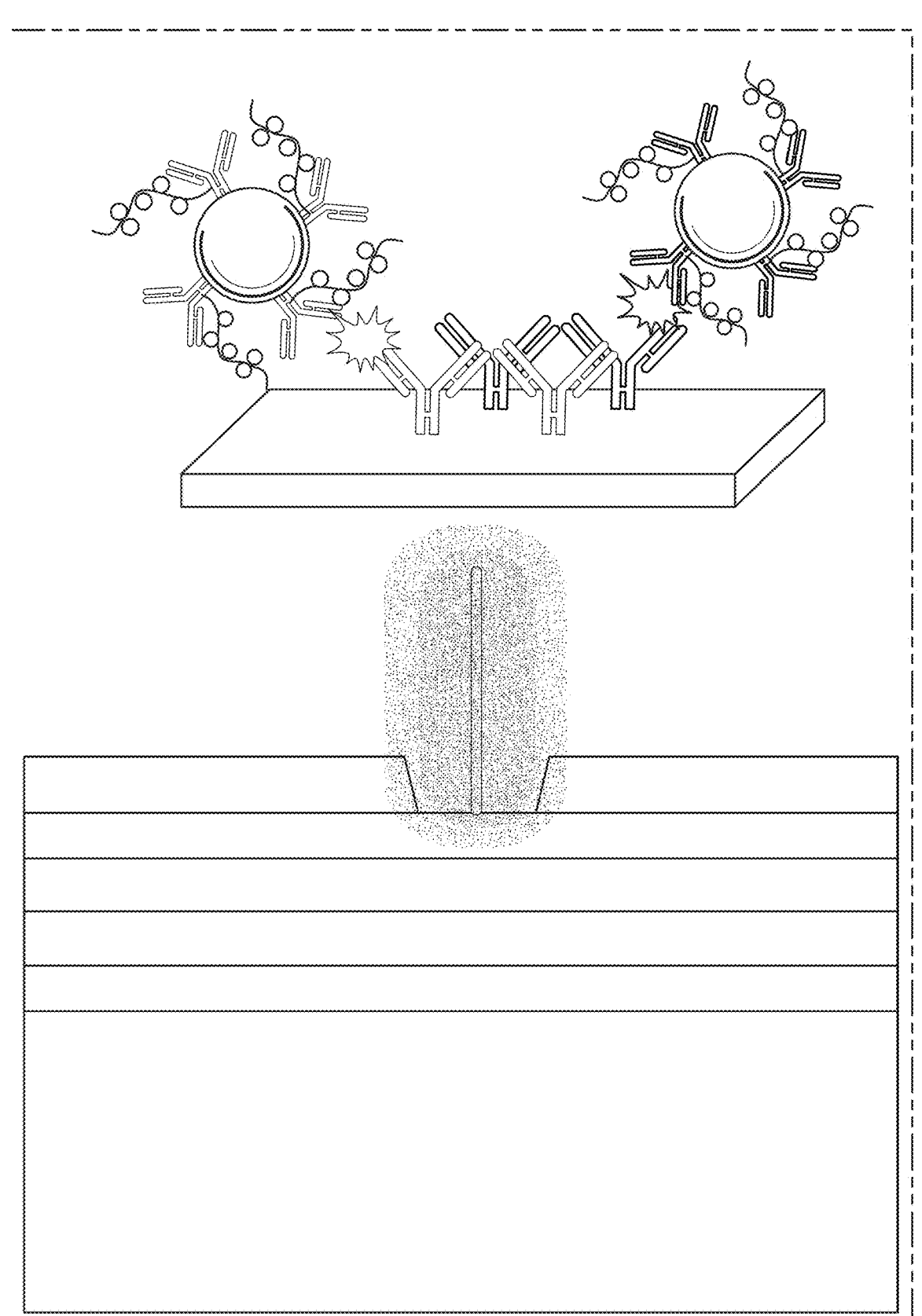
Figure 33:
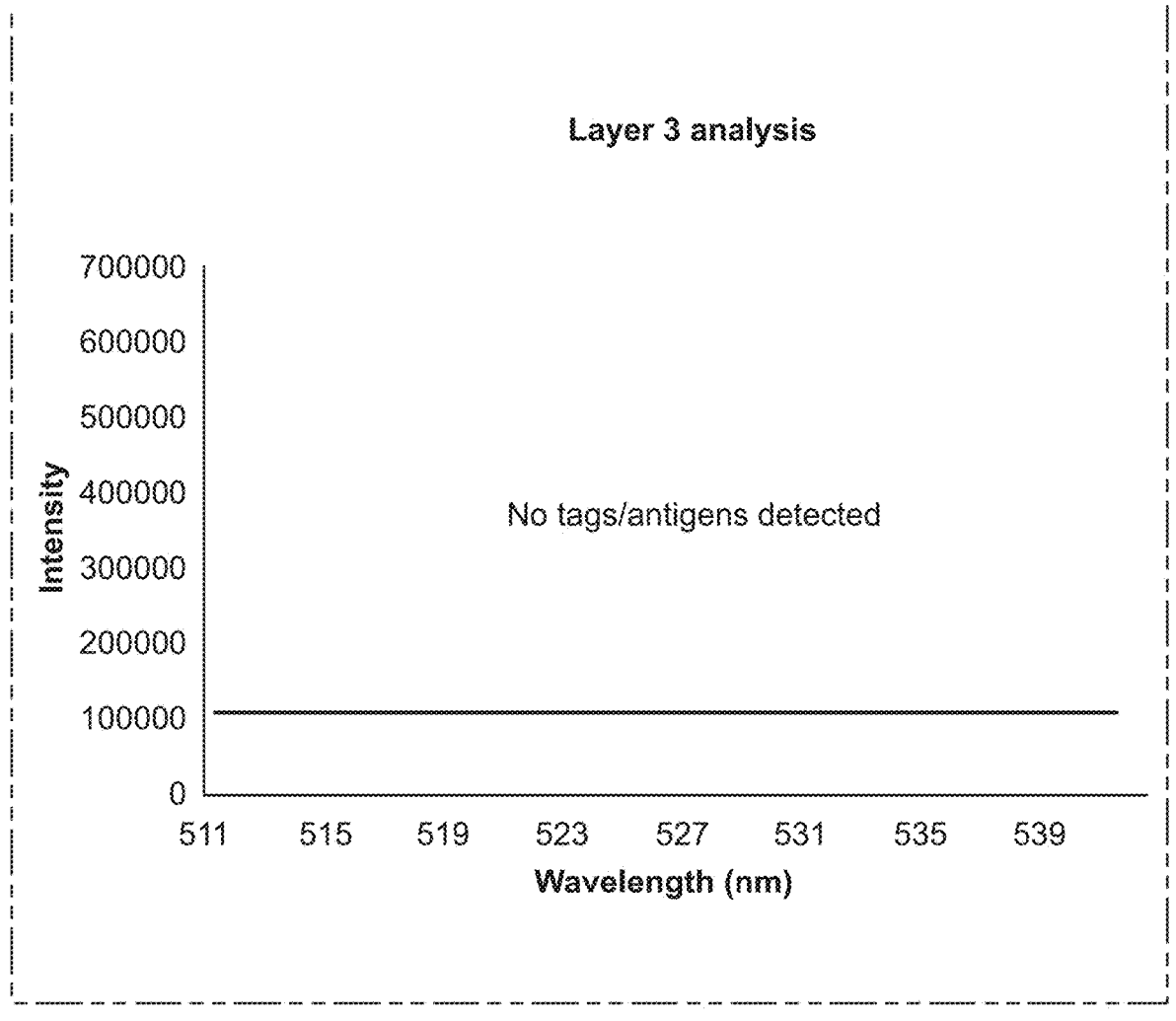
Figure 33:
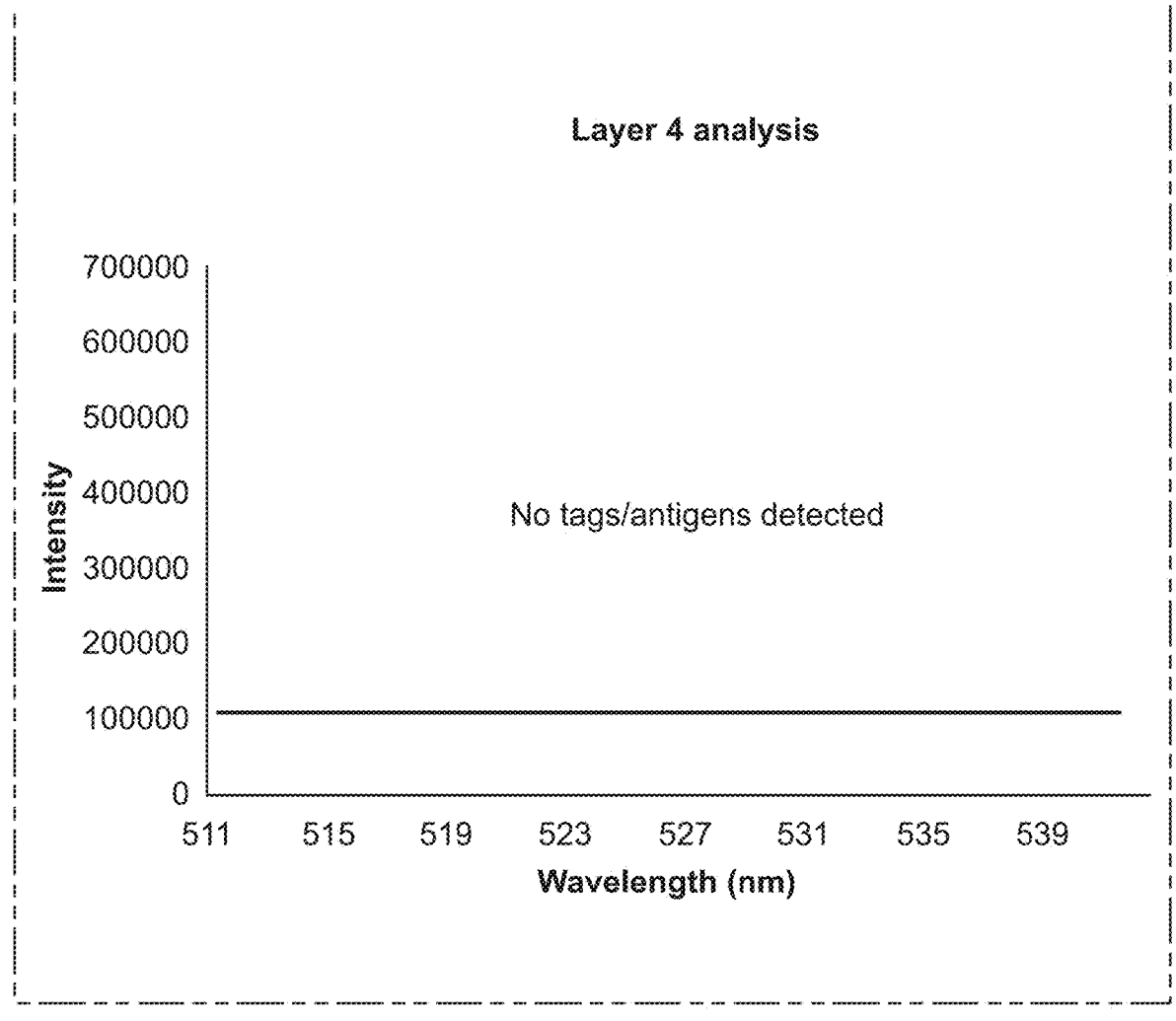
Figure 33:
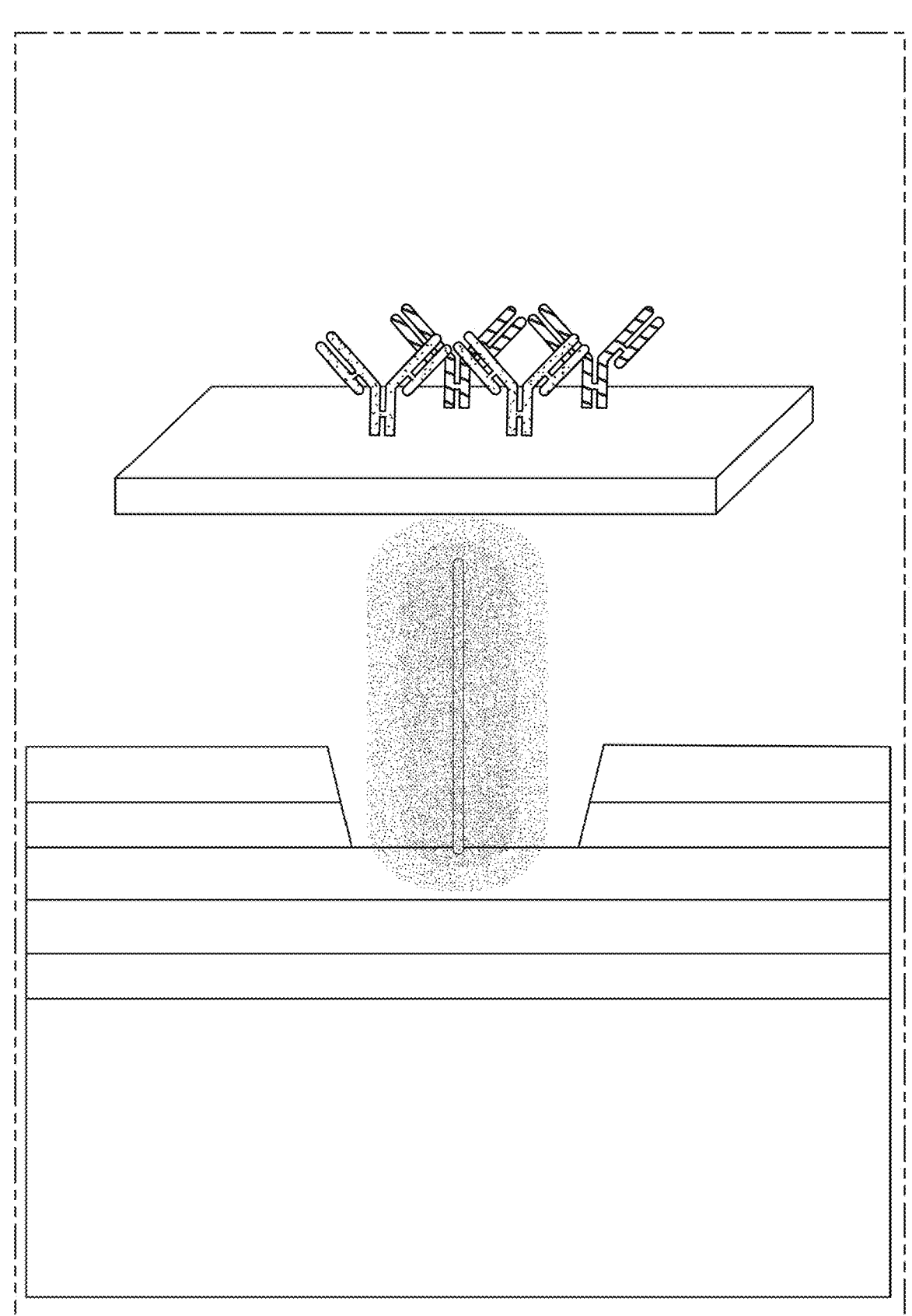
Figure 33:
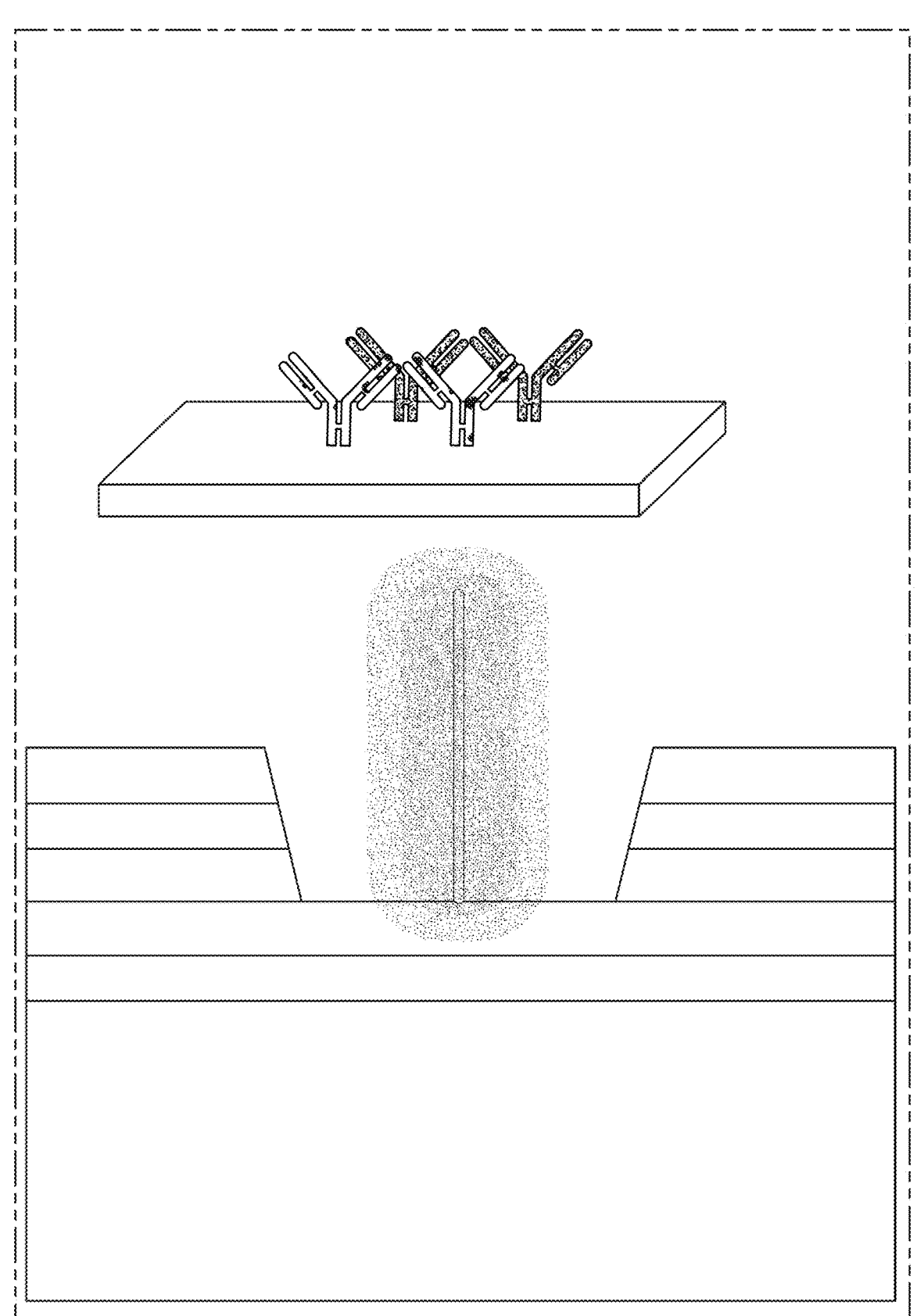
Figure 33:
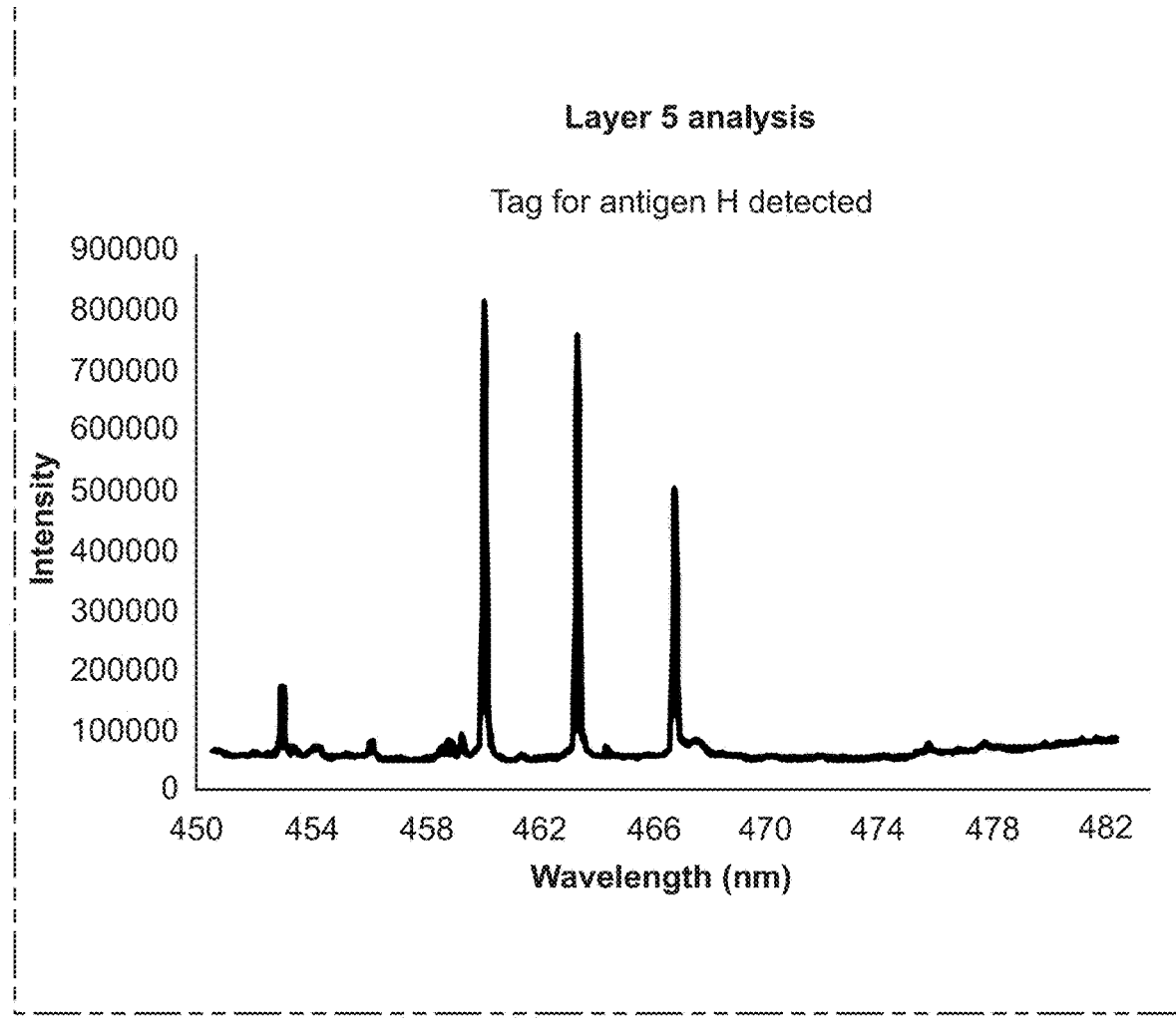
Figure 33:
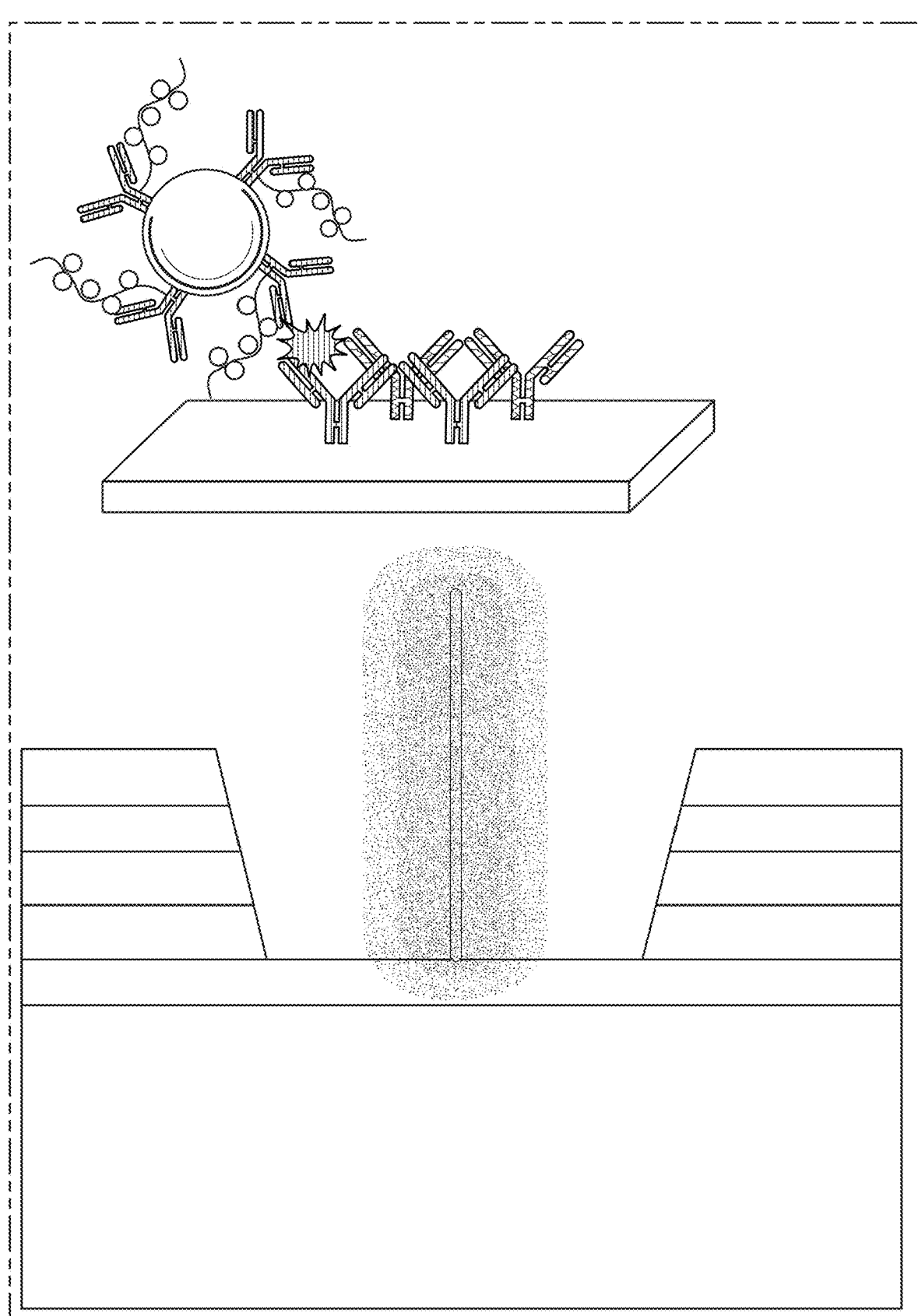

FIG. 33 shows assay detection results for the assay conducted in FIG. 32. As illustrated, toxins A-H were possible contaminants in the sample. Only Toxins A, B and G were found in the solution.

FIG. 32B illustrates use of a multi-layer bioassay to detect antigens (Reagents+Cartridge) in which the reagents do not include a nanoparticle core. A sample that is believed to be contaminated with toxins A-H is added to the paper bioassay (the sample actually contains toxins A, B and G). The antigens first bind to capture molecules in Layer 1. As the toxins and particles flow through the layers, they bind to specific layers. Note that flow is in a vertically direction (downward vertical flow) and this example describes vertical flow assays.

Figure 36:
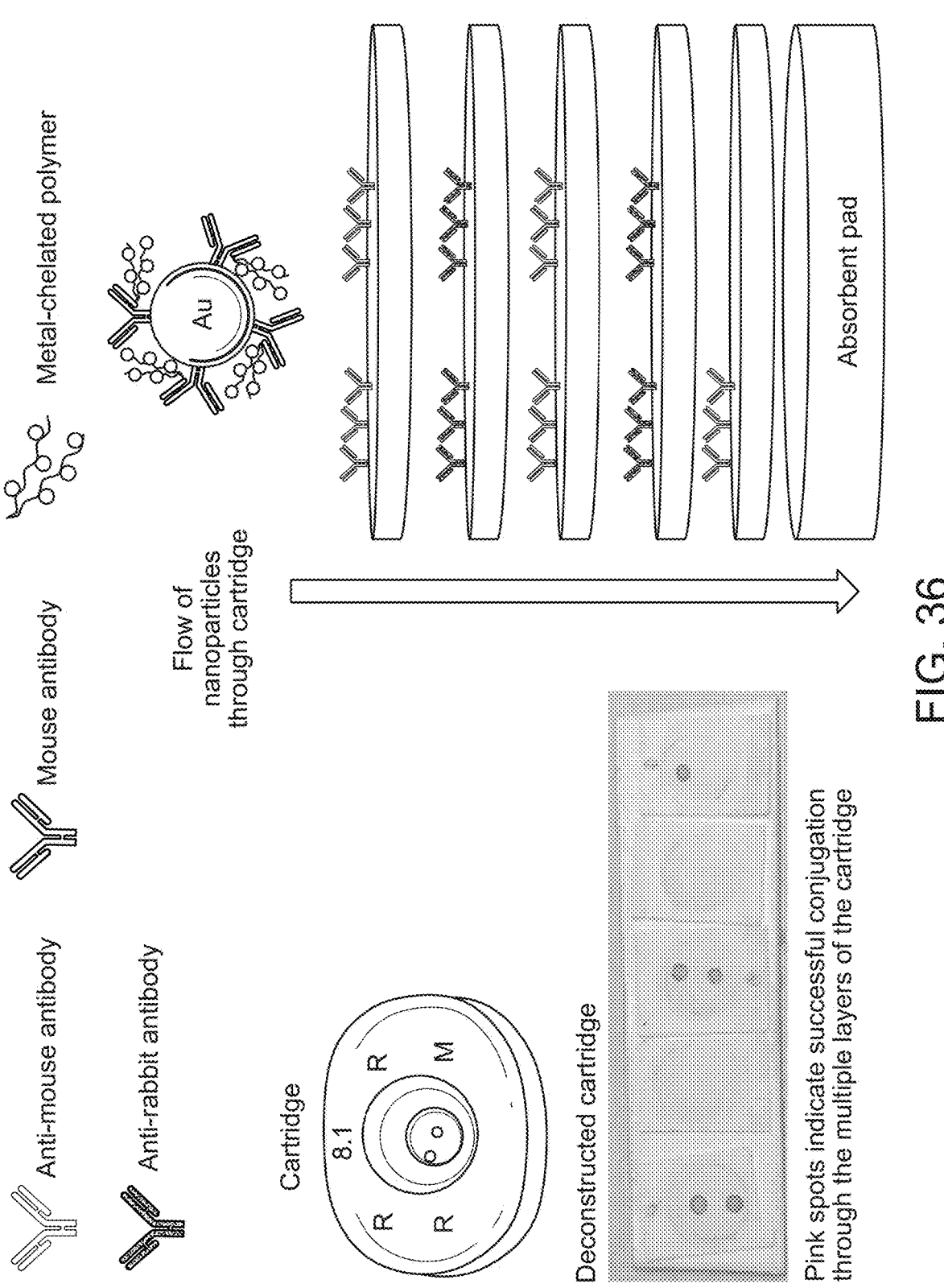
FIG. 36 shows a cartridge that was produced for a multiplex bioassay.

FIG. 36 shows a cartridge that was produced for a multiplex bioassay. The cartridge is designed for vertical flow, as shown on the right side of the figure. The pictures on the left of the cartridge show visually detectable pink spots that can be seen by the naked eye. The spots are produced by the nanoparticle core (composed of gold here but may be other visually detectable metals such as silver). Upon deconstruction of the cartridge to show the multiple layers, the pink spots on each layer indicate successful conjugation through the multiple layers of the cartridge.

What is claimed is:

1. A method for detecting a plurality of target analytes, the method comprising:

forming a first sandwich complex on a first paper substrate comprising a first target analyte from a sample and one or more first metal particles, and forming a second sandwich complex on a second paper substrate comprising a second target analyte from the sample and one or more second metal particles, wherein the first paper substrate is layered on top of the second paper substrate;

directing a laser emission from a laser source onto the first sandwich complex on the first paper substrate such that the laser emission causes the one or more first metal particles associated with the first sandwich complex to produce a first emission signal while also ablating at least a portion of the first paper substrate to expose at least a portion of the second paper substrate that comprises the second sandwich complex such that the laser emission also causes the one or more second metal particles associated with the second sandwich complex to produce a second emission signal; and detecting the first emission signal from the first sandwich complex on the first paper substrate, the first emission signal being indicative of presence of the first target analyte and detecting the second emission signal from the second sandwich complex on the second paper substrate, the second emission signal being indicative of presence of the second target analyte.

2. The method of claim 1, wherein forming the first sandwich complex comprises:

introducing the sample comprising the first target analyte to the first paper substrate comprising a first capture molecule that is specific to the first target analyte, wherein the first target analyte binds the first capture molecule; and introducing a first reagent to the first paper substrate, the first reagent comprising (i) a core metal nanoparticle having a second capture molecule coupled thereto or (ii) a second capture molecule without a core metal nanoparticle; and one or more first metal particles coupled to the second capture molecule, wherein the first reagent binds the first target analyte via the second capture molecule to thereby form the first sandwich complex on the first paper substrate; and forming the second sandwich complex comprises:

introducing the sample comprising the second target analyte to the second paper substrate comprising a third capture molecule that is specific to the second target analyte, wherein the second target analyte binds the third capture molecule; and introducing a second reagent to the second paper substrate, the second reagent comprising (i) a core metal nanoparticle having a fourth capture molecule coupled thereto or (ii) a fourth capture molecule without a core metal nanoparticle; and one or more first metal particles coupled to the fourth capture molecule, wherein the second reagent binds the second target analyte via the fourth capture molecule to thereby form the second sandwich complex on the second paper substrate.

3. The method of claim 2, wherein the sample comprises a third target analyte and the method further comprises:

forming a third sandwich complex on the first or second paper substrate, wherein the third sandwich complex comprises the third target analyte and one or more third metal particles;

directing a laser emission from the laser source onto the third sandwich complex such that the laser emission causes the one or more third metal particles associated with the third sandwich complex to produce a third emission signal; and detecting the third emission signal from the third sandwich complex, the third emission signal being indicative of presence of the third target analyte.

4. The method of claim 3, wherein forming the third sandwich complex comprises:

introducing the third target analyte in the sample to the first or second paper substrate comprising a fifth capture molecule that is specific to the third target analyte and different from the first, second, third, and fourth capture molecules, wherein the third target analyte binds the fifth capture molecule; and introducing a third reagent to the first or second paper substrate, the third reagent comprising (i) a core metal nanoparticle having a sixth capture molecule coupled thereto or (ii) a sixth capture molecule without a core metal nanoparticle; and one or more third metal particles coupled to the sixth capture molecule, wherein the one or more third metal particles are different from the one or more first or second metal particles and the third reagent binds the third target analyte via the sixth capture molecule to thereby form a third sandwich complex.

5. The method of claim 2, wherein the first and second reagents are introduced to the first and second paper substrates in a single liquid or separate liquids.

6. The method of claim 2, wherein the first capture molecule is an antibody.

7. The method of claim 1, wherein the first or second paper substrate is nitrocellulose paper.

* * * * *